United States Patent
Kim et al.

(10) Patent No.: US 11,747,261 B2
(45) Date of Patent: *Sep. 5, 2023

(54) HYDROGEL PARTICLES WITH TUNABLE OPTICAL PROPERTIES AND METHODS FOR USING THE SAME

(71) Applicant: Slingshot Biosciences, Inc., Emeryville, CA (US)

(72) Inventors: Jeffrey Kim, Berkeley, CA (US); Oliver Liu, San Francisco, CA (US); Jeremy Agresti, El Cerrito, CA (US); Anh Tuan Nguyen, San Jose, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 352 days.

This patent is subject to a terminal disclaimer.

(21) Appl. No.: 16/933,028

(22) Filed: Jul. 20, 2020

(65) Prior Publication Data

US 2020/0400546 A1 Dec. 24, 2020

Related U.S. Application Data

(63) Continuation of application No. 15/625,394, filed on Jun. 16, 2017, now Pat. No. 10,753,846, which is a
(Continued)

(51) Int. Cl.
*G01N 15/10* (2006.01)
*G01N 15/14* (2006.01)
(Continued)

(52) U.S. Cl.
CPC ........... *G01N 15/1012* (2013.01); *C12Q 1/04* (2013.01); *G01N 1/28* (2013.01); *G01N 15/1434* (2013.01);
(Continued)

(58) Field of Classification Search
None
See application file for complete search history.

(56) References Cited

U.S. PATENT DOCUMENTS 4,704,891 A 11/1987 Recktenwald et al.
4,774,189 A 9/1988 Schwartz
(Continued)

FOREIGN PATENT DOCUMENTS

CN 101245368 8/2008
CN 103744185 A 4/2014
(Continued)

OTHER PUBLICATIONS

International Search Report and Written Opinion for International Patent Application No. PCT/US2016/017029, dated May 19, 2016, 8 pages.
(Continued)

*Primary Examiner* — Xiaoyun R Xu
(74) *Attorney, Agent, or Firm* — COOLEY LLP

(57) ABSTRACT

Hydrogel particles and their use in cytometric applications are described. The hydrogel particles described herein are selectively tunable to have at least one optical property substantially similar to at least one optical property of a target cell. In this regard, the hydrogel particles provided herein, in one aspect, are used as a calibration reagent for the detection of a target cell in a sample.

41 Claims, 13 Drawing Sheets

A)

B)

Related U.S. Application Data continuation of application No. 15/018,769, filed on Feb. 8, 2016, now Pat. No. 9,714,897.

(60) Provisional application No. 62/184,192, filed on Jun. 24, 2015, provisional application No. 62/114,004, filed on Feb. 9, 2015.

(51) Int. Cl.
*C12Q 1/04* (2006.01)
*G01N 1/28* (2006.01)
*G01N 15/00* (2006.01)

(52) U.S. Cl.
CPC . *G01N 15/1459* (2013.01); *G01N 2001/2893* (2013.01); *G01N 2015/0065* (2013.01); *G01N 2015/1006* (2013.01); *G01N 2015/1018* (2013.01); *G01N 2015/149* (2013.01)

(56) References Cited

U.S. PATENT DOCUMENTS

| | | |
|---|---|---|
| 4,857,451 A | 8/1989 | Schwartz |
| 5,093,234 A | 3/1992 | Schwartz |
| 5,283,079 A | 2/1994 | Wang et al. |
| 5,395,688 A | 3/1995 | Wang et al. |
| 5,820,879 A | 10/1998 | Fernandez et al. |
| 5,888,823 A | 3/1999 | Matsumoto et al. |
| 6,372,813 B1 | 4/2002 | Johnson et al. |
| 6,586,176 B1 | 7/2003 | Trnovsky et al. |
| 6,806,058 B2 | 10/2004 | Jesperson et al. |
| RE39,542 E | 4/2007 | Jain et al. |
| 7,294,503 B2 | 11/2007 | Quake et al. |
| 7,314,584 B2 | 1/2008 | Tsutsui et al. |
| 7,482,167 B2 | 1/2009 | Sammak et al. |
| 7,601,539 B2 | 10/2009 | Kawate |
| 8,030,095 B2 | 10/2011 | Harriman |
| 8,187,885 B2 | 5/2012 | Purvis, Jr. |
| 8,415,161 B2 | 4/2013 | Yan et al. |
| 8,415,173 B2 | 4/2013 | Harriman |
| 8,704,158 B2 | 4/2014 | Haberstroh et al. |
| 8,748,183 B2 | 6/2014 | Durack et al. |
| 9,476,101 B2 | 10/2016 | Pregibon et al. |
| 9,714,897 B2 | 7/2017 | Kim et al. |
| 9,915,598 B2 | 3/2018 | Kim et al. |
| 10,344,100 B1 | 7/2019 | Vashist et al. |
| 10,392,557 B2 | 8/2019 | Chan |
| 10,481,068 B2 | 11/2019 | Kim et al. |
| 10,753,846 B2 | 8/2020 | Kim et al. |
| 10,942,109 B2 | 3/2021 | Kim et al. |
| 11,085,036 B2 | 8/2021 | Norberg et al. |
| 11,180,752 B2 | 11/2021 | Wu et al. |
| 11,213,490 B2 | 1/2022 | Shoichet et al. |
| 11,313,782 B2 | 4/2022 | Kim et al. |
| 11,598,768 B2 | 3/2023 | Kim |
| 2003/0132538 A1 | 7/2003 | Chandler |
| 2005/0118230 A1 | 6/2005 | Hill et al. |
| 2005/0172476 A1 | 8/2005 | Stone et al. |
| 2005/0176056 A1 | 8/2005 | Sammak et al. |
| 2005/0208573 A1 | 9/2005 | Bell et al. |
| 2006/0163385 A1 | 7/2006 | Link et al. |
| 2006/0240560 A1 | 10/2006 | Bakker et al. |
| 2007/0003442 A1 | 1/2007 | Link et al. |
| 2007/0054119 A1 | 3/2007 | Garstecki et al. |
| 2007/0259415 A1 | 11/2007 | Zigova et al. |
| 2008/0019921 A1 | 1/2008 | Zhang |
| 2008/0044472 A1 | 2/2008 | Garcia et al. |
| 2009/0148961 A1 | 6/2009 | Luchini et al. |
| 2010/0234252 A1 | 9/2010 | Moradi-Araghi et al. |
| 2010/0285594 A1 | 11/2010 | Purvis, Jr. |
| 2011/0218123 A1 | 9/2011 | Weitz et al. |
| 2011/0318820 A1 | 12/2011 | Hinz et al. |
| 2012/0309651 A1 | 12/2012 | Pregibon et al. |
| 2013/0177973 A1 | 7/2013 | Kondo |
| 2015/0177115 A1 | 6/2015 | Kim et al. |
| 2015/0267196 A1 | 9/2015 | Alsberg et al. |
| 2016/0258856 A1 | 9/2016 | Kim et al. |
| 2018/0275040 A1 | 9/2018 | Kim et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0399428 A1 | 12/2020 | Kleine-Brüggeney et al. |
| 2021/0231552 A1 | 7/2021 | Kim et al. |
| 2021/0341469 A1 | 11/2021 | Kim |
| 2022/0178810 A1 | 6/2022 | Kim |
| 2022/0260476 A1 | 8/2022 | Kim |
| 2022/0364976 A1 | 11/2022 | Kim et al. |
| 2023/0067460 A1 | 3/2023 | Nguyen et al. |

FOREIGN PATENT DOCUMENTS

| | | |
|---|---|---|
| CN | 104641217 A | 5/2015 |
| EP | 3585364 A1 | 1/2020 |
| JP | 07-196916 A | 8/1995 |
| JP | 2002-510541 | 4/2002 |
| JP | 2007-114026 A | 5/2007 |
| JP | 2012-11269 A | 1/2012 |
| JP | 2013-520530 | 6/2013 |
| JP | 2013-155358 A | 8/2013 |
| JP | 2014-508516 A | 4/2014 |
| WO | WO-1989/10566 A1 | 11/1989 |
| WO | WO-2000/08212 A1 | 2/2000 |
| WO | WO-2001/32829 A2 | 5/2001 |
| WO | WO-2003/000014 A2 | 1/2003 |
| WO | WO-2005013896 A2 | 2/2005 |
| WO | WO-2006/078841 A1 | 7/2006 |
| WO | WO-2006/096571 A2 | 9/2006 |
| WO | WO-2008/115653 A2 | 9/2008 |
| WO | WO-2008121342 A2 | 10/2008 |
| WO | WO-2010/025988 A1 | 3/2010 |
| WO | WO-2011/098407 A1 | 8/2011 |
| WO | WO-2012/033811 A1 | 3/2012 |
| WO | WO-2020037214 A1 | 2/2020 |
| WO | WO-2021154900 A1 | 8/2021 |

OTHER PUBLICATIONS

Non-Final Office Action issued by The United States Patent and Trademark Office for U.S. Appl. No. 13/858,912, dated Jun. 6, 2016, 27 pages.

Final Office Action issued by The United States Patent A67and Trademark Office for U.S. Appl. No. 13/858,912, dated Jan. 11, 2017, 15 pages.

Non-Final Office Action issued by The United States Patent and Trademark Office for U.S. Appl. No. 15/145,856, dated Apr. 6, 2017, 13 pages.

Non-Final Office Action issued by The United States Patent and Trademark Office for U.S. Appl. No. 15/018,769, dated Mar. 9, 2017, 11 pages.

Non-Final Office Action issued by The United States Patent and Trademark Office for U.S. Appl. No. 15/895,307, dated Jul. 18, 2018, 13 pages.

Extended European Search Report issued by the European Patent Office for Application No. 16749674.4, dated Sep. 6, 2018, 12 pages.

Non-Final Office Action issued by The United States Patent and Trademark Office for U.S. Appl. No. 15/625,394, dated Feb. 8, 2019, 16 pages.

Final Office Action issued by The United States Patent and Trademark Office for U.S. Appl. No. 15/625,394, dated Jun. 12, 2019, 10 pages.

Office Action issued by the Japanese Patent Office for Application No. 2017-559788, dated Oct. 17, 2019, 12 pages including English translation.

Non-Final Office Action issued by The United States Patent and Trademark Office for U.S. Appl. No. 15/625,394, dated Dec. 13, 2019, 9 pages.

(56) References Cited

OTHER PUBLICATIONS

Office Action issued by the Taiwanese Patent Office for Application No. 105104380, dated Dec. 6, 2019, 9 pages (including English translation).
Second Office Action issued by the Chinese Patent Office for Application No. 201680019908.4, dated Mar. 30, 2020, 27 pages including English translation.
Patanarut, Alexis, el al. "Synthesis and characterization of hydrogel particles containing Cibacron Blue F3G-A." Colloids and Surfaces A: Physicochemical and Engineering Aspects 362(1):8-19 (2010).
Luchini, Alessandra, et al. "Smart hydrogel particles: biomarker harvesting: one-step affinity purification, size exclusion, and protection against degradation." Nano letters 8(1): 350-361 (2008).
Bele, Marjan, Olavi Siiman, and Egon Matijevic. "Preparation and flow cytomelry of uniform silica-fluorescent dye rnicrospheres." Journal of colloid and interface science 254(2):274-282 (2002).
Proll, Guenther, et al. "Potential of label-free detection in high-content-screening applications." Journal of Chromatography A 1116(1):2-8 (2007).
Hasegawa, Urara, el al. "Nanogel-quanlum dot hybrid nanoparticles for live cell imaging." Biochemical and biophysical esearch communications 331(4):917-921 (2005).
Tomczak, Nikodem, el al. "Designer polymer-quantum dot architectures." Progress in Polymer Science 34:393-430 (2009).
Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).
Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).
Kim, Jin-Woong, Andrew S. Utada, Alberto Fernandez-Nieves, Zhibing Hu, and David A. Weitz, "Fabrication of Monodisperse Gel Shells and Functional Microgels in Microfluidic Devices," Angew. Chern. Int. Ed. 46:819-1822 (2007).
Non-Final Office Action issued by The United States Patent and Trademark Office for U.S. Appl. No. 16/684,694, dated Sep. 29, 2020, 17 pages.
Office Action issued by the Canadian Patent Office for Application No. 2,975,301, dated Jul. 19, 2022, 4 pages.
Non-Final Office Action issued by The United States Patent and Trademark Office for U.S. Appl. No. 16/933,028, dated Oct. 14, 2022, 7 pages.
Non-Final Office Action for U.S. Appl. No. 17/727,879, dated Dec. 15, 2022, and received Dec. 15, 2022, 7 pages.
Office Action issued by the Canadian Patent Office for Application No. 2,975,301, dated Dec. 28, 2022, 5 pages.
Advisory Action issued by The United States Patent and Trademark Office for U.S. Appl. No. 15/625,394, dated Sep. 20, 2019, 5 pages.
Advisory Action issued by The United States Patent and Trademark Office for U.S. Appl. No. 17/155,294, dated Nov. 29, 2021,, 5 pages.
Final Office Action issued by The United States Patent and Trademark Office for U.S. Appl. No. 15/895,307, dated Mar. 25, 2019, 17 pages.
Final Office Action issued by The United States Patent and Trademark Office for U.S. Appl. No. 17/155,294, dated Jul. 1, 2021, 15 pages.
First Examination Report Issued by the Indian Patent Office for Application No. 201737028044, dated Feb. 26, 2021, 6 pages.
International Search Report and Written Opinion for International Patent Application No. PCT/US21/014538, dated Apr. 8, 2021, 19 pages.
International Search Report and Written Opinion for International Patent Application No. PCT/US21/030590, dated Jul. 26, 2021, 13 pages.
Non-Final Office Action issued by The United States Patent and Trademark Office for U.S. Appl. No. 17/155,294, dated Mar. 22, 2021, 8 pages.
Non-Final Office Action dated Nov. 18, 2021 for U.S. Appl. No. 17/307,127, 9 pages.
Non-Final Office Action iused by The United States Patent and Trademark Office for U.S. Appl. No. 17/307,127, dated Jun. 17, 2022, 7 pages.
Office Action issued by the Australian Patent Office for Application No. AU2020201783, dated Sep. 14, 2020, 3 pages.
Office Action issued by the Chinese Patent Office for Application No. 201680019908.4, dated Jul. 25, 2019 (rec'd Sep. 4, 19), 7 pages including English translation.
Office Action issued by the Japanese Patent Office for Application No. 2020-72811, dated May 25, 2021, 7 pages including English translation.
Office Action issued by the Canadian Patent Office for Application No. 2,975,301, dated Feb. 10, 2022, 3 pages.
Office Action issued by the Chinese Patent Office for Application No. 201680019908.4, dated Mar. 25, 2021, 24 pages including English translation.
Office Action issued by the European Patent Office for Application No. 16749674.4, dated Apr. 20, 2021, 10 pages.
Office Action issued by the Korean Patent Office for Application No. 10-2022-7028984, dated Oct. 6, 2022, 3 pages including English translation.
Taiwanese Office Action for Application No. TW201 30008837 dated Nov. 4, 2021, 6 pages, including English translation.
Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374, XP028865323.
International Search Report and Written Opinion for International Application No. PCT/US2022/048283 dated Feb. 14, 2023, 14 pages.
Liu, A.L., et al., "Methods for Generating Hydrogel Particles for Protein Delivery," Annals of Biomedical Engineering, Jun. 2016, vol. 44 (6), pp. 1946-1958, XP035897969.
Non-Final Office Action for U.S. Appl. No. 17/990,360, dated Mar. 16, 2023, 9 pages.
Office Action for European Application No. EP20160749674 dated Mar. 30, 2023, 11 pages.
Pérez-Luna, V.H., et al., "Encapsulation of Biological Agents in Hydrogels for Therapeutic Applications," Gels, Jul. 11, 2018, vol. 4 (3), pp. 61, XP093020197.

A)

B)

A

B

C

A

B

C

D

HYDROGEL PARTICLES WITH TUNABLE OPTICAL PROPERTIES AND METHODS FOR USING THE SAME

CROSS REFERENCE TO RELATED APPLICATIONS

This application is a continuation of U.S. patent application Ser. No. 15/625,394, filed Jun. 16, 2017, which in turn is a continuation of U.S. patent application Ser. No. 15/018,769, filed Feb. 8, 2016, now U.S. Pat. No. 9,714,897, which in turn claims priority to and benefit of U.S. Provisional Application No. 62/114,004, filed Feb. 9, 2015 and U.S. Provisional Application No. 62/184,192, filed Jun. 24, 2015; this application is also a continuation of PCT/US16/17029, filed Feb. 8, 2016, which in turn also claims priority to and benefit of U.S. Provisional Application Nos. 62/114,004 and No. 62/184,192; each of the aforementioned applications is incorporated by reference herein in their entireties.

BACKGROUND

Flow cytometry is a technique that allows for the rapid separation, counting, and characterization of individual cells and is routinely used in clinical and laboratory settings for a variety of applications. The technology relies on directing a beam of light onto a hydrodynamically-focused stream of liquid. A number of detectors are then aimed at the point where the stream passes through the light beam: one in line with the light beam (Forward Scatter or FSC) and several perpendicular to it (Side Scatter or SSC). FSC correlates with the cell volume and SSC depends on the inner complexity of the particle (e.g., shape of the nucleus, the amount and type of cytoplasmic granules or the membrane roughness). As a result of these correlations, different specific cell types exhibit different FSC and SSC, allowing cell types to be distinguished in flow cytometry.

The ability to identify specific cell types, however, relies on proper calibration of the instrument, a process that has relied on the use of purified cells of the cell type of interest. Obtaining these purified cells can require costly, laborious procedures that are prone to batch-to-batch variation. Therefore, there is a need in the art for synthetic compositions with tunable optical properties that can mimic specific cell types in devices such as flow cytometers.

SUMMARY

In one aspect of the invention, a hydrogel particle comprising a polymerized monomer and having at least one surface is provided. The hydrogel particle has at least one optical property that is substantially similar to the at least one optical property of a target cell. The optical property in one embodiment, is a side scatter profile (SSC), forward scatter profile (FSC), a fluorescence emission profile, or a combination thereof. The target cell can be any target cell that the user specifies. For example, in one embodiment, the target cell is an immune cell, stem cell or cancer cell.

In another aspect, a method for calibrating a cytometric device for analysis of a target cell, is provided. In one embodiment, the method comprises inserting into the device a hydrogel particle having at least one optical property substantially similar to a target cell, wherein the hydrogel particle comprises a polymerized monomer and has at least one surface. The method further comprises measuring the at least one optical property of the hydrogel particle using the cytometric device. The at least one optical property in one embodiment, is used as a reference to detect a target cell in a sample.

In yet another aspect, a method for detecting a target cell in a sample is provided. The method comprises inserting into the device a hydrogel particle having at least one optical property substantially similar to a target cell, wherein the hydrogel particle comprises a polymerized monomer. The method further comprises measuring the at least one optical property of the hydrogel particle using the cytometric device. A sample comprising a plurality of cells is inserted into the cytometric device, and the at least one optical property of individual cells of the plurality are measured. Finally, a determination is made, based on the optical property measurement, whether the target cell or plurality thereof is present in the sample.

In one embodiment of the methods provided herein, the hydrogel particle comprises a biodegradable monomer. In some embodiments, biodegradable monomers and/or biocompatible particles are configured such that they can be used with and in sorting cells that are re-introduced into a biological system without presenting a risk if a particle also goes into the biological system. In a further embodiment, the biodegradable monomer is a monosaccharide, disaccharide, polysaccharide, peptide, protein, or protein domain. In even a further embodiment, the biodegradable monomer is functionalized with acrylamide or acrylate.

DETAILED DESCRIPTION OF THE INVENTION

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

Several critical calibration measurements for flow cytometers require precise time resolution, such as setting the offset time between lasers, and calculating the delay time between detection and sorting of an object. Due to the fluidic conditions within the instrument, precise setting of these timing parameters requires the use of calibration particles that are the same size as the cells to be analyzed. Timing calibrations are typically performed using polystyrene beads with variable fluorescent intensities to calibrate the response of an excitation source and to set the inter-laser timing delay and sorting delay. Flow cytometers can also be calibrated using forward and side scatter signals which are general measures of size and granularity or complexity of the target sample. These calibrations are crucial for the accurate performance of the cytometer and for any downstream analysis or sorting of cell populations. The disclosed hydrogel particles exhibit tuned scatter properties and are suitable for use as calibration reagents for a range of mammalian or bacterial cell types. Scattering is a standard metric for distinguishing cell types in heterogeneous mixtures for clinical, food safety, and research purposes.

Figure 1:
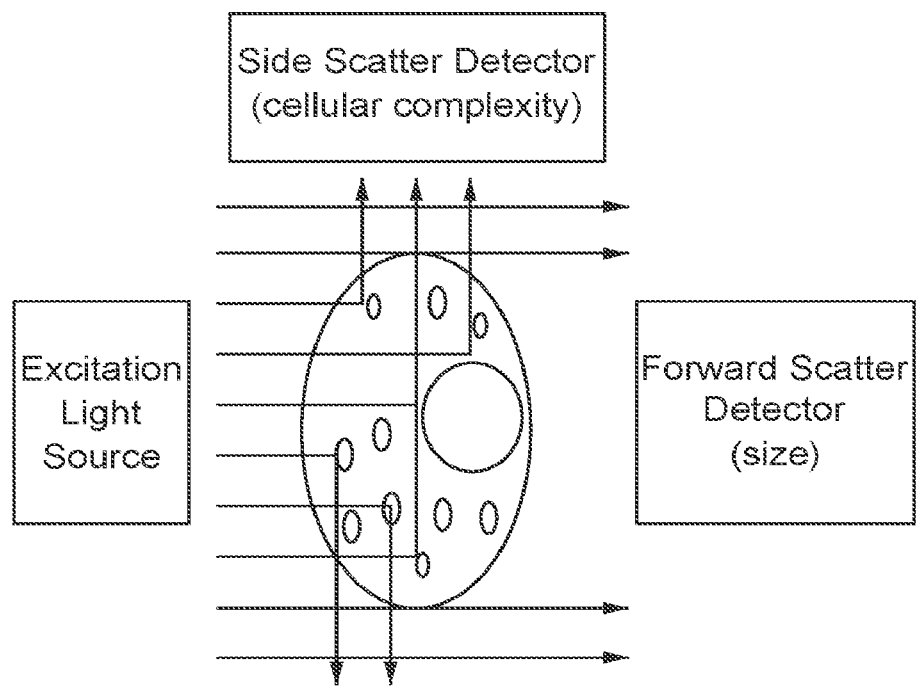
FIG. 1 illustrates the optical properties of disclosed hydrogel particles compared to polystyrene beads.
Figure 1:
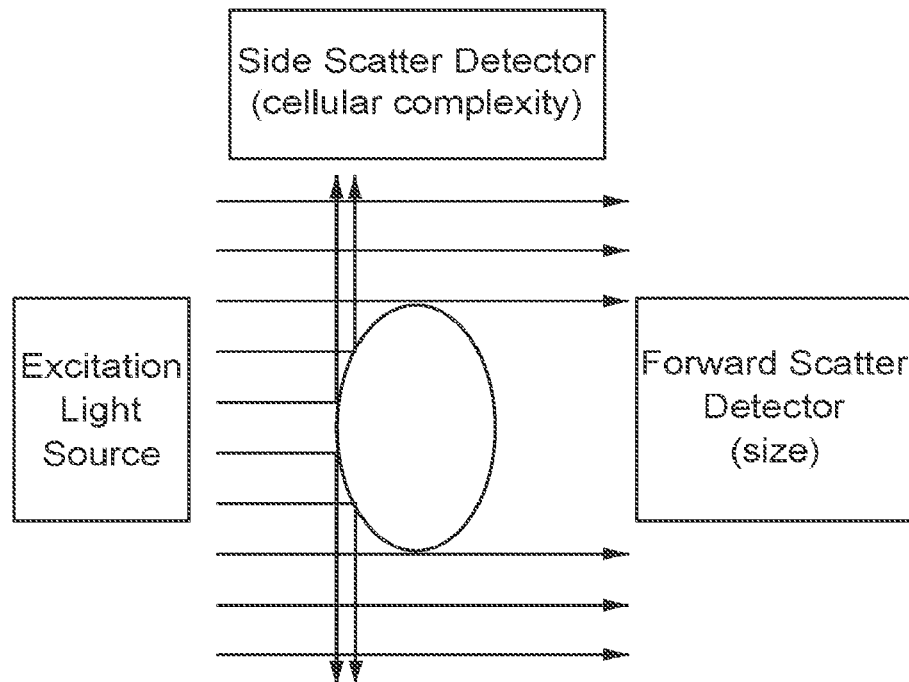

Although polystyrene particles can be used to set inter-laser and sorting delays for some applications, many eukaryotic cell types fall outside of the size range of commercially available polystyrene particles (1-20 µm) making it nearly impossible to accurately calibrate a flow cytometer for these targets. Also, as shown in FIG. 1, polystyrene particles are fundamentally limited in the optical properties that can possess such as side scattering, which is a general measure of cellular complexity. Polystyrene particles are therefore limited in the two most important passive optical measurements used in flow cytometry: FSC (forward scattering), and SSC (side scattering) which measure the size and complexity of the target respectively. Due to these limitations of polystyrene, users must rely on purified cell lines to calibrate fluorescent intensity, inter-laser delay, sort delays, size and cellular complexity for experiments. This is a lengthy and labor-intensive process that increases the cost of flow cytometry validation and research pipelines significantly. More importantly, these calibration cell lines introduce biological variation, causing disparities in the interpretation of data.

Moreover, quality control (QC) for calibration of flow cytometers is also a crucial consideration when these instruments are used for clinical applications, for example, to isolate human T-regulatory cells or stem cells for downstream cellular therapies. The FDA mandates that the sterility, identity, purity, and potency of a cell therapy product be demonstrated before administration to patients (Riley et al. (2009). Immunity 30, pp. 656-665). Contamination of a cellular population with polystyrene QC particles could therefore be problematic, as polystyrene has been implicated in certain cancers. Additionally, a cellular population that is contaminated with a QC standard that is enzymatically degraded or digested internally after administration to a patient potentially overcomes contamination issues, should they arise.

The present invention addresses these and other needs, as discussed below.

Figure 10:
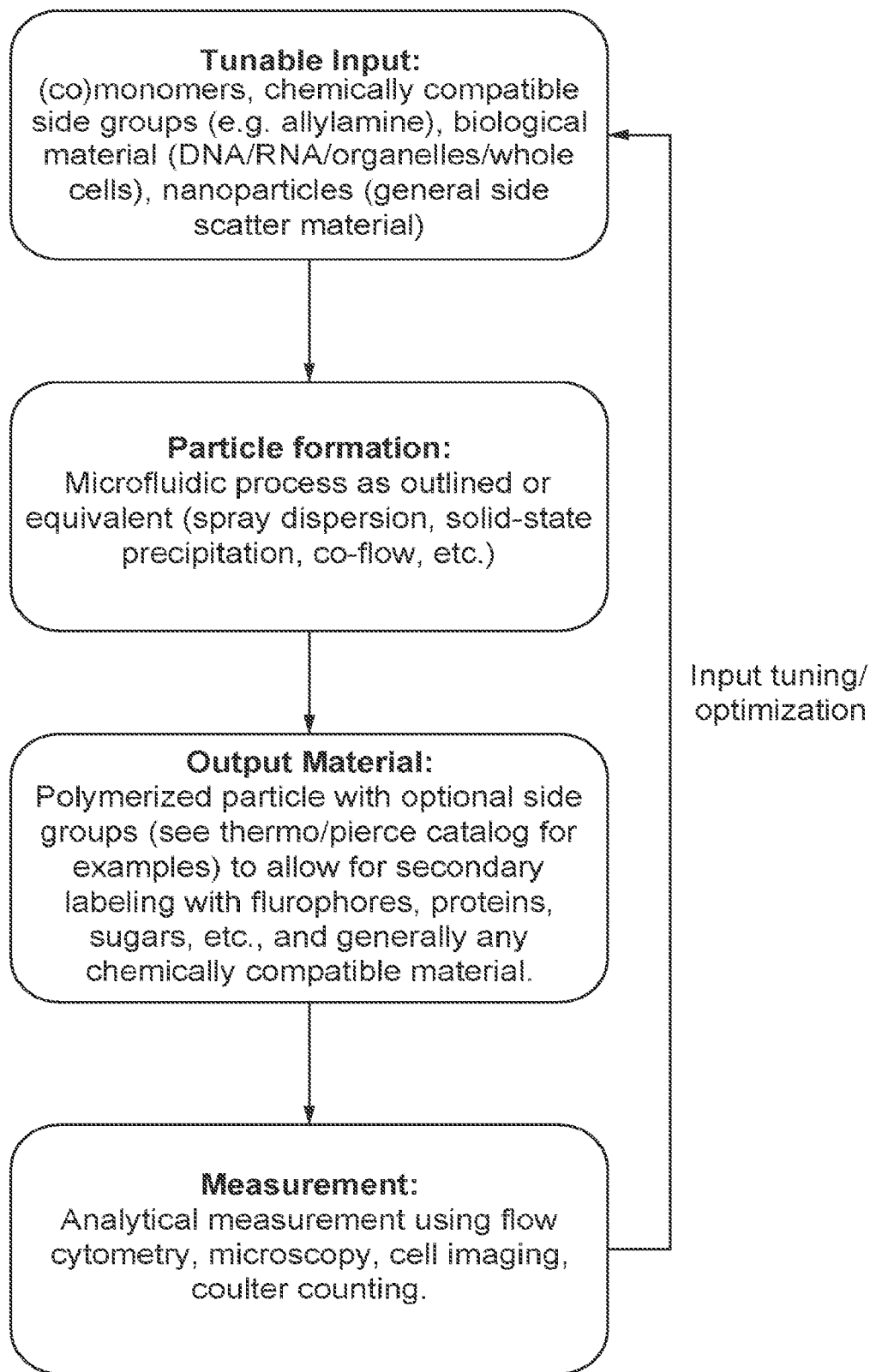
FIG. 10 shows one embodiment of hydrogel parameter tuning to match and/or mimic desired cell population metrics.

In one aspect, a composition comprising a plurality of hydrogel particles is provided, wherein the individual hydrogel particles of the plurality each has one or more optical properties substantially similar to one or more optical properties of a target cell. Each of the individual hydrogel particles of the plurality independently comprises a hydrogel which is synthesized by polymerizing one or more monomers, i.e., to form a homopolymer or copolymer. As discussed further below, the use of bifunctional monomers allows for the further derivatization of hydrogels, e.g., with fluorescent dyes, cell surface markers or epitope binding fragments thereof, or a combination thereof. An example of hydrogel parameter tuning to meet/match desired cell subpopulation metrics is provided at FIG. 10. Methods for tuning the properties of a hydrogel are described herein. The ability to adjust a range of parameters including hydrogel components and concentration of the same allows for the ability to tune a particle to mimic a wide range of cells, for example one of the cell types described herein.

As provided above, in one aspect, the present invention provides individual hydrogel particles each having one or more optical properties substantially similar to one or more optical properties of a target cell. In one embodiment, the one or more optical properties, is a side scatter profile, a forward scatter profile or a secondary marker profile, such as a fluorescence marker profile, for example a fluorescence marker profile of a fluorescently-labeled antibody that binds to the surface of the hydrogel particle. "Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

The present invention is based in part on the unexpected discovery that one or more optical properties of a hydrogel particle can be independently modulated by altering the composition of the hydrogel particle, for example, by altering the amount of initial monomer (or co-monomer) in the composition, by altering the surface functionalization, by altering the amount of a polymerization initiator or by altering the amount of crosslinker. For example, side scattering (SSC) can be modulated without substantially affecting forward scattering (FSC), and vice versa. Furthermore, the optical properties (e.g. refractive index) of hydrogel particles can be tuned without having a substantial effect on density of the particle. This is a surprising and useful feature, as hydrogel particles that serve as surrogates for cells in cytometric methods such as flow cytometry or (fluorescence-activated cell sorting) FACS require a minimal density in order to function in those assays.

In another aspect, a method for producing a hydrogel particle is provided, wherein the hydrogel particle has one or more optical properties substantially similar to the optical properties of one or more target cells. In one embodiment, the hydrogel particle has pre-determined optical properties. The optical property, in one embodiment, is SSC, FSC, fluorescence emission, or a combination thereof.

In yet another aspect, a method of calibrating a cytometric device for analysis of a target cell is provided. In one embodiment, the method comprises (a) inserting into the device a hydrogel particle having optical properties substantially similar to the optical properties of the target cell; b) measuring the optical properties of the hydrogel particle using the cytometric device, thereby calibrating the cytometric device for analysis of the target cell. Cytometric devices are known in the art, and include commercially available devices for performing flow cytometry and FACS.

As provided above, in one aspect of the invention, compositions comprising a plurality of hydrogel particles are provided. A hydrogel is a material comprising a macromolecular three-dimensional network that allows it to swell when in the presence of water, to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. Synthetically prepared hydrogels can be prepared by polymerizing a monomeric material to form a backbone and cross-linking the backbone with a crosslinking agent. As referred to herein, the term "hydrogel" refers to the macromolecular material whether dehydrated or in a hydrated state. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

In one embodiment, a hydrogel particle disclosed herein comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water. In another embodiment, a hydrogel particle has a water content of about 10 percent by weight to about 95 percent by weight, or about 20 percent by weight to about 95 percent by weight, or about 30 percent by weight to about 95 percent by weight, or about 40 percent by weight to about 95 percent by weight, or about 50 percent by weight to about 95 percent by weight, or about 60 percent by weight to about 95 percent by weight, or about 70 percent by weight to about 95 percent by weight, or about 80 percent by weight to about 95 percent by weight.

The hydrogels provided herein, in the form of particles, are synthesized by polymerizing one or more of the monomers provided herein. The synthesis is carried out to form individual hydrogel particles. The monomeric material (monomer) in one embodiment is polymerized to form a homopolymer. However, in another embodiment copolymers of different monomeric units (i.e., co-monomers) are synthesized and used in the methods provided herein. The monomer or co-monomers used in the methods and compositions described herein, in one embodiment, is a bifunctional monomer or includes a bifunctional monomer (where co-monomers are employed). In one embodiment, the hydrogel is synthesized in the presence of a crosslinker. In a further embodiment, embodiment, the hydrogel is synthesized in the presence of a polymerization initiator.

The amount of monomer can be varied by the user of the invention, for example to obtain a particular optical property that is substantially similar to that of a target cell. In one embodiment, the monomeric component(s) (i.e., monomer, co-monomer, bifunctional monomer, or a combination thereof, for example, bis/acrylamide in various crosslinking ratios, allyl amine or other co-monomers which provide chemical functionality for secondary labeling/conjugation or alginate is present at about 10 percent by weight to about 95 percent weight of the hydrogel. In a further embodiment, the monomeric component(s) is present at about 15 percent by weight to about 90 percent weight of the hydrogel, or about 20 percent by weight to about 90 percent by weight of the hydrogel.

Examples of various monomers and cross-linking chemistries available for use with the present invention are provided in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes. For example, hydrazine (e.g., with an NHS ester compound) or EDC coupling reactions (e.g., with a maleimide compound) can be used to construct the hydrogels of the invention.

In one embodiment, a monomer for use with the hydrogels provided herein is lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof.

In one embodiment, one or more of the following monomers is used herein to form a hydrogel of the present invention: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate or a combination thereof.

In another embodiment, one or more of the following monomers is used herein to form a tunable hydrogel: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl)methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, as described in U.S. Pat. No. 6,657,030, which is incorporated by reference in its entirety herein for all purposes.

Both synthetic monomers and bio-monomers can be used in the hydrogels provided herein, to form synthetic hydrogels, bio-hydrogels, or hybrid hydrogels that comprise a synthetic component and a bio-component (e.g., peptide, protein, monosaccharide, disaccharide, polysaccharide, primary amines sulfhydryls, carbonyls, carbohydrates, carboxylic acids present on a biolmolecule). For example, proteins, peptides or carbohydrates can be used as individual monomers to form a hydrogel that includes or does not include a synthetic monomer (or polymer) and in combination with chemically compatible co-monomers and crosslinking chemistries (see for example, the Thermo Scientific Crosslinking Technical Handbook entitled "Easy molecular bonding crosslinking technology," available at tools.lifetechnologies.com/content/sfs/brochures/1602163-Crosslinking-Reagents-Handbook.pdf, the disclosure of which is incorporated by reference in its entirety for all purposes). Compatible crosslinking chemistries include, but are not limited to, amines, carboxyls, and other reactive chemical side groups. Representative reactive groups amenable for use in the hydrogels and monomers described herein are provided in Table 1, below.

TABLE 1

Crosslinker reactive groups amenable for bio-monomer conjugation

| Reactivity class | Target functional group | Reactive chemical group |
| --- | --- | --- |
| Amine reactive | —$NH_2$ | NHS ester |
| | | Imidoester |
| | | Penafluorophenyl ester |
| | | Hydroxymethyl phosphine |
| Carboxyl-to-amine reactive | —COOH | Carbodiimide (e.g., EDC) |
| Sulfhydryl-reactive | —SH | Maeleimide |
| | | Haloacetyl |
| | | (bromo- or iodo-) |
| | | Pyridylisulfide |
| | | Thiosulfonate |
| | | Vinylsulfonate |
| Aldehyde-reactive (oxidized sugars, carbonyls) | —CHO | Hydrazine |
| | | Alkoxyamine |
| Photo-reactive, i.e., nonselective, random insertion | Random | Diazirine |
| | | Aryl azide |
| Hydroxyl (nonaqueous)-reactive | —OH | Isocyanate |
| Azide-reactive | —$N3$ | phosphine |

In general, any form of polymerization chemistry/methods commonly known by those skilled in the art, can be employed to form polymers. In some embodiments, polymerization can be catalyzed by ultraviolet light-induced radical formation and reaction progression. In other embodiments, a hydrogel particle of the disclosure is produced by the polymerization of acrylamide or the polymerization of acrylate. For example, the acrylamide in one embodiment is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In one embodiment, an acrylate-functionalized poly(ethylene) glycol monomer is used as a hydrogel monomer. For example, the PEG in one embodiment is an acrylate or acrylamide functionalized PEG.

In some embodiments, a hydrogel particle comprises a monofunctional monomer polymerized with at least one bifunctional monomer. One example includes, but is not limited to, the formation of poly-acrylamide polymers using acrylamide and bis-acrylamide (a bifunctional monomer). In another embodiment, a hydrogel particle provided herein comprises a bifunctional monomer polymerized with a second bifunctional monomer. One example include, but is not limited to, the formation of polymers with mixed composition containing compatible chemistries such as acrylamide, bis-acrylamide, and bis-acrylamide structural congeners containing a wide range of additional chemistries. The range of chemically compatible monomers, bifunctional monomers, and mixed compositions is obvious to those skilled in the art and follows chemical reactivity principles know to those skilled in the art. (reference Thermo handbook and acrylamide polymerization handbook). See, for example, the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf) and the Polyacrylamide Emulsions Handbook (SNF Floerger, available at snf.com.au/downloads/Emulsion_Handbook_E.pdf), the disclosure of each of which is incorporated by reference in its entirety for all purposes.

In one embodiment, a hydrogel particle provided herein comprises a polymerizable monofunctional monomer and is a monofunctional acrylic monomer. Non-limiting examples of monofunctional acrylic monomers for use herein are acrylamide; methaciylamide; N-alkylacrylamides such as N-ethylacrylamide, N-isopropylacrylamide or N-tertbutylacrylamide; N-alkylmethaciylamides such as N-ethylmethacrylamide or Nisopropylmethacrylamide; N,N-dialkylacrylamides such as N,N-dimethylacrylamide and N,N-diethylacrylamide; N-[(dialkylamino)alkyl]acrylamides such as N-[3dimethylamino) propyl]acrylamide or N-[3-(diethylamino)propyl]acrylamide; N-[(dialkylamino) alkyl]methacrylamides such as N-[3-dimethylamino)propyl]methacrylamide or N-[3-(diethylamino) propyl]methacrylamide; (dialkylamino)alkyl acrylates such as 2-(dimethylamino) ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore or cell surface receptor (or domain thereof).

In some embodiments, a bifunctional monomer is selected from the group consisting of: allyl amine, allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'methylene bismethacrylamide, N,N'-ethylene bisacrylamide, N,N'-ethylene bismethacrylamide, N,N'propylene bisacrylamide and N,N'-(1,2-dihydroxyethylene) bisacrylamide.

Higher-order branched chain and linear co-monomers can be substituted in the polymer mix to adjust the refractive index while maintaining polymer density, as described in U.S. Pat. No. 6,657,030, incorporated herein by reference in its entirety for all purposes.

In some embodiments, a hydrogel comprises a molecule that modulates the optical properties of the hydrogel. Molecules capable of altering optical properties of a hydrogel are discussed further below.

In one embodiment, an individual hydrogel particle or a plurality thereof comprises a biodegradable polymer as a hydrogel monomer. In one embodiment, the biodegradable polymer is a poly(esters) based on polylactide (PLA), polyglycolide (PGA), polycaprolactone (PCL), and their copolymers. In one embodiment, the biodegradable polymer is a carbohydrate or a protein, or a combination thereof. For example, in one embodiment, a monosaccharide, disaccharide or polysaccharide, (e.g., glucose, sucrose, or maltodextrin) peptide, protein (or domain thereof) is used as a hydrogel monomer. Other biodegradable polymers include poly(hydroxyalkanoate)s of the PHB-PHV class, additional poly(ester)s, and natural polymers, for example, modified poly(saccharide)s, e.g., starch, cellulose, and chitosan. In another embodiment, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma. Aldrich (St. Louis, Mo.).

The protein in one embodiment comprises only natural amino acids. However, the invention is not limited thereto. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). The biodegradable polymer in one embodiment, is used as a co-monomer, i.e., in a mixture of monomers. The biodegradable polymer in one embodiment is a bifunctional monomer.

The biomonomer, in one embodiment, is functionalized with acrylamide or acrylate. For example, in one embodiment, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In one embodiment, an acrylamide or acrylate functionalized monosaccharide, disaccharide or polysaccharide is used as a polymerizable hydrogel monomer. In one embodiment, a structural polysaccharide is used as a polymerizable hydrogel monomer. In a further embodiment, the structural polysaccharide is an arabinoxylan, cellulose, chitin or a pectin. In another embodiment, alginic acid (alginate) is used as a polymerizable hydrogel monomer. In yet another embodiment, a glycosaminoglycan (GAG) is used as a polymerizable monomer in the hydrogels provided herein. In a further embodiment, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

Biocompatible monomers for use with the hydrogels described herein include in one embodiment, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in this invention include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan in one embodiment is used as a hydrogel monomer (either as a single monomer or as a co-monomer). Hyaluronan in one embodiment, is functionalized, for example with acrylate or acrylamide. Hyaluronan is a high molecular weight GAG composed of disaccharide repeating units of N-acetylglucosamine and glucuronic acid linked together through alternating $\beta$-1,4 and $\beta$-1,3 glycosidic bonds. In the human body, hyaluronate is found in several soft connective tissues, including skin, umbilical cord, synovial fluid, and vitreous humor. Accordingly, in one embodiment, where one or more optical properties of a skin cell, umbilical cord cell or vitreous humor cell is desired to be mimicked, in one embodiment, hyaluronan is used as a hydrogel monomer. Methods for fabricating hydrogel particles are described in Xu et al. (2012). Soft Matter. 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed $\beta$-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein in one embodiment is functionalized with acrylate or acrylamide.

In one embodiment, an individual hydrogel particle or a plurality thereof comprises a peptide, protein, a protein domain, or a combination thereof as a hydrogel monomer or plurality thereof. In a further embodiment, the protein is a structural protein, or a domain thereof, for example, such as silk, elastin, titin or collagen, or a domain thereof. In one embodiment, the protein is an extracellular matrix (ECM) component (e.g., collagen, elastin, proteoglycan). In even a further embodiment, the structural protein is collagen. In yet a further embodiment, the collagen is collagen type I, collagen type II or collagen type III or a combination thereof. In another embodiment, the hydrogel monomer comprises a proteoglycan. In a further embodiment, the proteoglycan is decorin, biglycan, testican, bikunin, fibromodulin, lumican, or a domain thereof.

In another embodiment, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In a further embodiment, the acrylate functionalized structural protein hydrogel monomer comprises a proteoglycan, e.g., decorin, biglycan, testican, bikunin, fibromodulin, lumican, or a domain thereof.

In one embodiment PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). *Proc. Natl. Acad. Sci. U.S.A.* 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). *Biomaterials* 30, 1089; Martino et al. (2011). *Sci. Trans. Med.* 3, 100ra89; Hu and Messersmith (2003). *J. Am. Chem. Soc.* 125, 14298, each of which is incorporated by reference in its entirety for all purposes.

In one embodiment, recombinant DNA methods are used to create proteins, designed to gel in response to changes in pH or temperature, for example, by the methods described by Petka et al. (1998). *Science* 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

Common cross linking agents that can be used to crosslink the hydrogels provided herein include but are not limited to ethylene glycol dimethacrylate (EGDMA), tetraethylene glycol dimethacrylate, and N,N'-15 methylenebisacrylamide. The range of additional crosslinking chemistries which can be used are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

In one embodiment, polymerization of a hydrogel is initiated by a persulfate or an equivalent initiator that catalyzes radical formation. The range of compatible initiators are known to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The persulfate can be any water-soluble persulfate. Non-limiting examples of water soluble persulfates are ammonium persulfate and alkali metal persulfates. Alkali metals include lithium, sodium and potassium. In some embodiments, the persulfate is ammonium persulfate or potassium persulfate. In a further embodiment, polymerization of the hydrogel provided herein is initiated by ammonium persulfate.

Polymerization of a hydrogel can be accelerated by an accelerant which can catalyze the formation of polymerization-labile chemical side groups. The range of possible accelerants is known to those skilled in the art and follow general chemical reactivity principles see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The accelerant in one embodiment, is a tertiary amine. The tertiary amine can be any water-soluble tertiary amine. In one embodiment, an accelerant is used in the polymerization reaction and is N,N,N',N'tetramethylethylenediamine, 3-dimethylamino) propionitrile, or N,N,N',N'tetramethylethylenediamine (TEMED). In another embodiment, an accelerant is used in the polymerization reaction and isazobis (isobutyronitrile) (AIBN).

Figure 2:
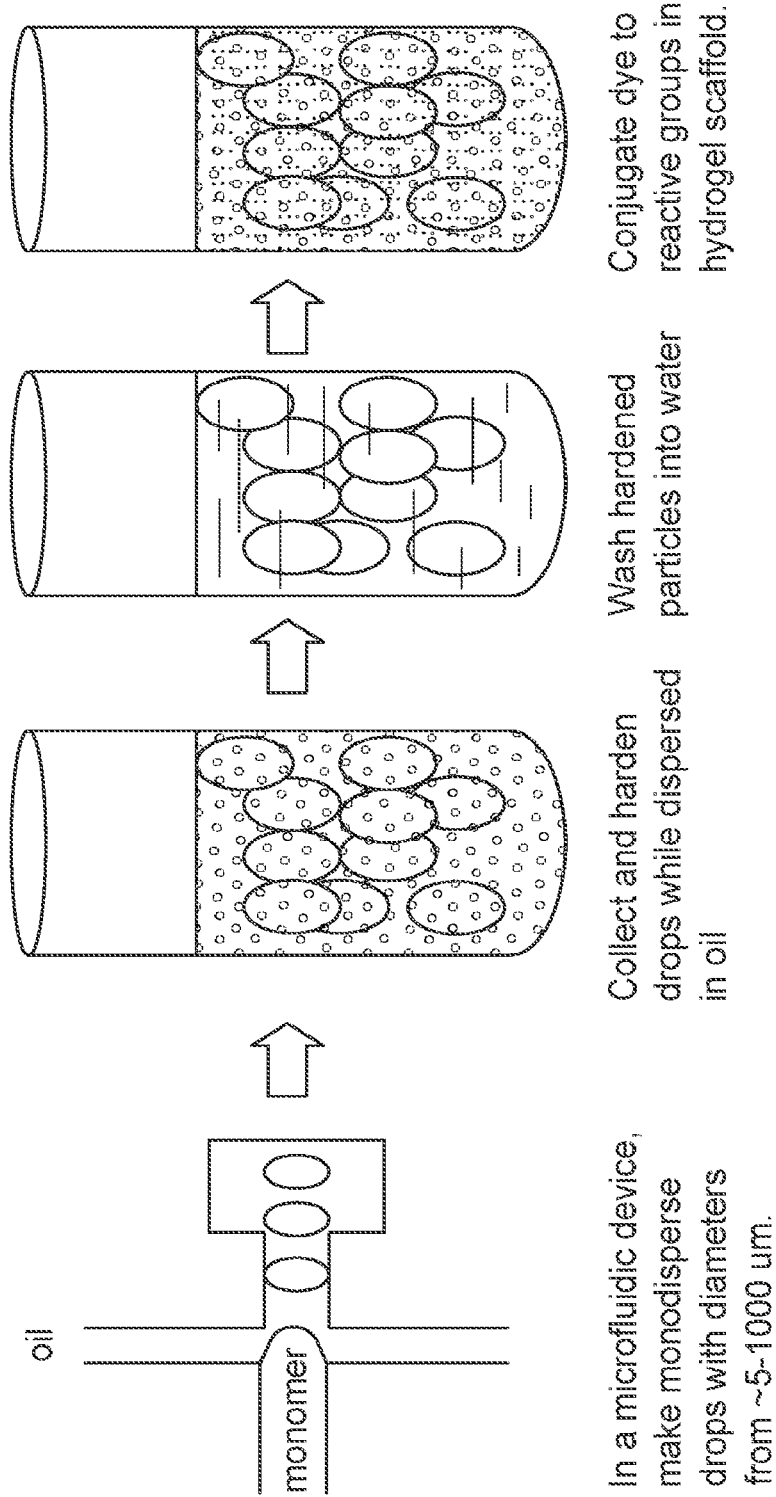
FIG. 2 depicts the process of producing labeled hydrogel particles of the disclosure.

As discussed above, the hydrogel for use in the compositions and methods described herein can include any of the monomeric units and crosslinkers as described herein, and in one aspect, are produced as hydrogel particles by polymerizing droplets (see, e.g., FIG. 2). Microfluidic methods of producing a plurality of droplets, including fluidic and rigidified droplets, are known to those of ordinary skill in the art, and described in US Patent Publication No. 2011/0218123 and U.S. Pat. No. 7,294,503, each incorporated herein by reference in their entireties for all purposes. Such methods provide for a plurality of droplets containing a first fluid and being substantially surrounded by a second fluid, where the first fluid and the second fluid are substantially immiscible (e.g., droplets containing an aqueous-based liquid being substantially surrounded by an oil based liquid).

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets. Average diameters of the particles can be measured, for example, by light scattering techniques. Average diameters of hydrogel particles in one embodiment, are tailored, for example by varying flow rates of the fluid streams of the first and second fluids within the channel(s) of a microfluidic device, or by varying the volume of the channel(s) of the microfluidic device.

Accordingly, the disclosure provides population of hydrogel particles comprising a plurality of hydrogel particles, wherein the population of hydrogel particles is substantially monodisperse.

The term microfluidic refers to a device, apparatus or system including at least one fluid channel having a cross-sectional dimension of less than 1 mm, and a ratio of length to largest cross-sectional dimension perpendicular to the channel of at least about 3:1. A micro fluidic device comprising a micro fluidic channel is especially well suited to preparing a plurality of mono disperse droplets.

Non-limiting examples of microfluidic systems that may be used with the present invention are disclosed in U.S. Patent Application Publication No. 2006/0163385; U.S. Patent Application Publication No. 2005/0172476; U.S. Patent Application Publication No. 2007/000342; International Patent Application Publication No. WO 2006/096571; U.S. Patent Application Publication No. 2007/0054119; U.S. Pat. No. 7,776,927; and International Patent Application Publication No. WO 2006/078841, each incorporated herein by reference in their entireties for all purposes.

Droplet size is related to microfluidic channel size. The micro fluidic channel may be of any size, for example, having a largest dimension perpendicular to fluid flow of less than about 5 mm or 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in some embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In some embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in diameter. In one embodiment, a hydrogel particle has a diameter in the range of 5 µm to 100 µm.

In some embodiments, a hydrogel particle of the disclosure is spherical in shape.

In some embodiments, a hydrogel particle of the disclosure does not comprise agarose.

Hydrogel particles in one embodiment, is carried by suspension polymerization, which is also referred to in the art as pearl, bead or granular polymerization (see Elbert (2011). Acta Biomater. 7, pp. 31-56, incorporated by reference herein in its entirety for all purposes). In suspension polymerization, the monomer is insoluble in the continuous phase, for example an aqueous monomer solution in a continuous oil phase. In suspension polymerization, polymerization initiation occurs within the monomer-rich droplets and with greater than one radical per droplet at any time. The monomer phase in one embodiment includes a monomer which can be a bifunctional monomer or a plurality of monomer species (co-monomers, which can be a plurality of bifunctional monomers. The monomer phase in one embodiment, includes an initiator and/or a crosslinking agent.

Emulsion polymerization can also be used to form the hydrogel particles described herein. In emulsion polymerization, the monomer has poor solubility in the continuous phase, similar to suspension polymerization, however, polymerization initiation occurs outside the monomer droplets (see Elbert (2011). Acta Biomater. 7, pp. 31-56, incorporated by reference herein in its entirety for all purposes). In emulsion polymerization embodiments, the initiator causes chain growth of the monomer (or co-monomers) dissolved in the continuous phase or monomer contained in micelles if surfactants are present.

In another embodiment, hydrogel particles are formed by precipitation polymerization, for example as described in Elbert (2011). Acta Biomater. 7, pp. 31-56, incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in one embodiment, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in one embodiment, results in a narrow size distribution of particles. Additional methods include but are not limited to lithographic particle formation (Helgeson et al. (2011). Curr. Opin. Colloid. Interface Sci. 16, pp. 106-117, incorporated by reference herein in its entirety for all puposes) membrane emulsification (e.g., by the micosieve emulsification technology techniques described by Nanomi B. V. (Netherlands)) and microchannel emulsification (Sugiura et al. (2002). Languimir 18, pp. 5708-5712, incorporated by reference herein in its entirety) and bulk emulsification (SNF Floerger, available at snf.com.au/downloads/Emulsion_Handbook_E.pdf, incorporated by reference herein in its entirety).

In one embodiment, hydrogel particles are formed within a microfluidic device having two oil channels that focus on a central stream of aqueous monomer solution. In this embodiment, droplets form at the interface of the two channels and central stream to break off droplets in water-in-oil emulsion. Once droplets are formed, in one embodiment, they are stabilized prior to polymerization, for example, by adding a surfactant to the oil phase. However, in another embodiment, droplets are not stabilized prior to polymerization. Polymerization of the monomer in one embodiment is triggered by adding an accelerator (e.g., N,N,N',N'tetramethylethylenediamine) to one or both of the oil channels after initial droplets are formed.

The aqueous monomer solution as provided above can include a single monomer species or a plurality of monomer species. The aqueous monomer solution can include co-monomers, a bifunctional monomer or a combination thereof. In one embodiment, the monomer or plurality of monomers can includes a bifunctional monomer, for example, one of the monomers described above. As described below, co-monomers can be used to modulate forward scatter or side scatter, for example, by adjusting the refractive index of the hydrogel particle.

In one embodiment, the central stream of aqueous monomer solution comprises a cross-linker, for example, N,N'-bisacrylamide. In a further embodiment, the central stream of aqueous monomer solution comprises a cross-linker and an accelerator, in addition to the monomer. In yet a further embodiment, the aqueous monomer solution comprises an initiator, for example an oxidizing agent such as ammonium persulfate.

Figure 11:
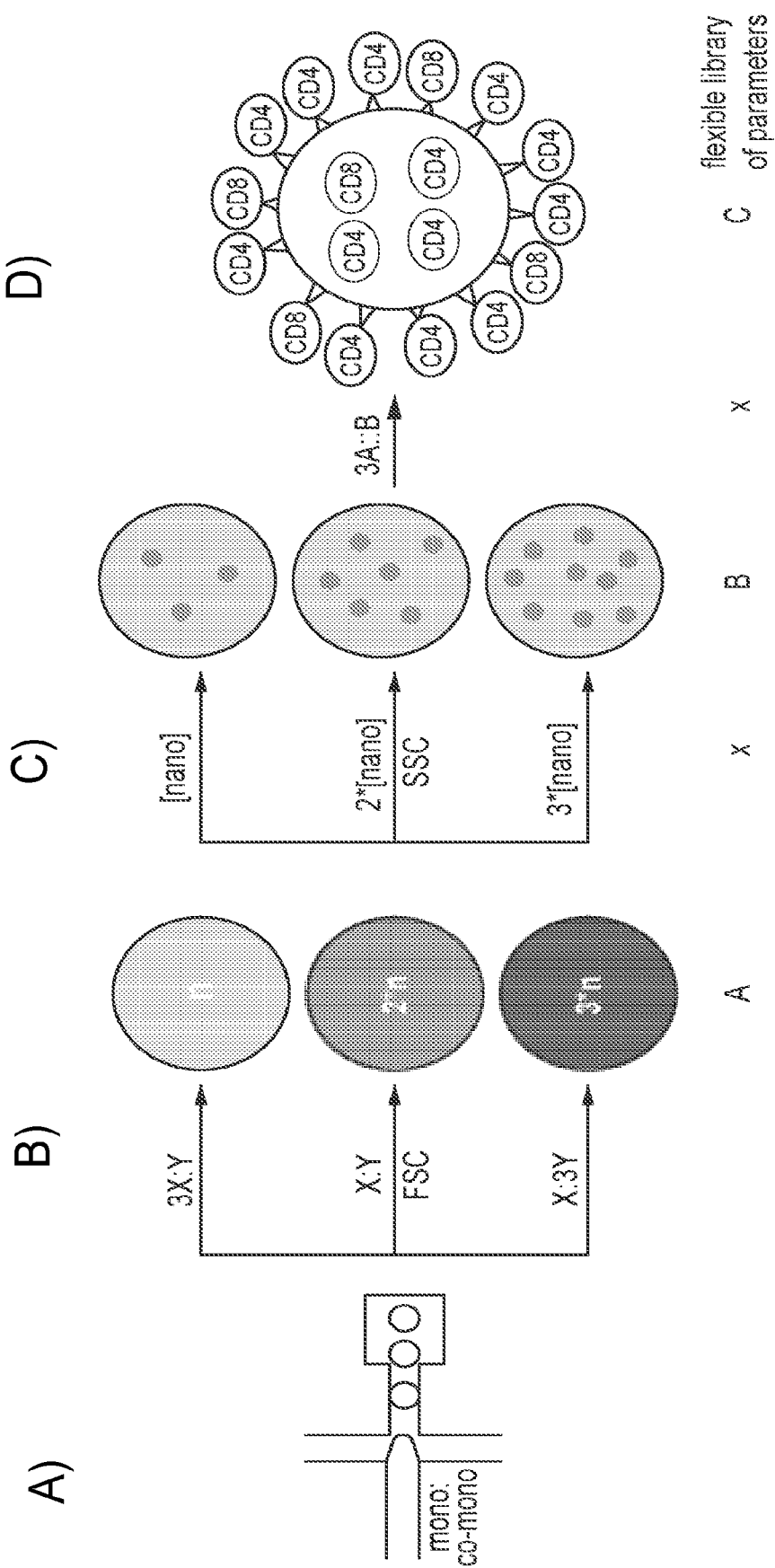
FIGS. 11 and 12 are diagrams showing embodiments of how to adjust the forward scatter, side scatter and surface properties of a hydrogel particle.
Figure 12:
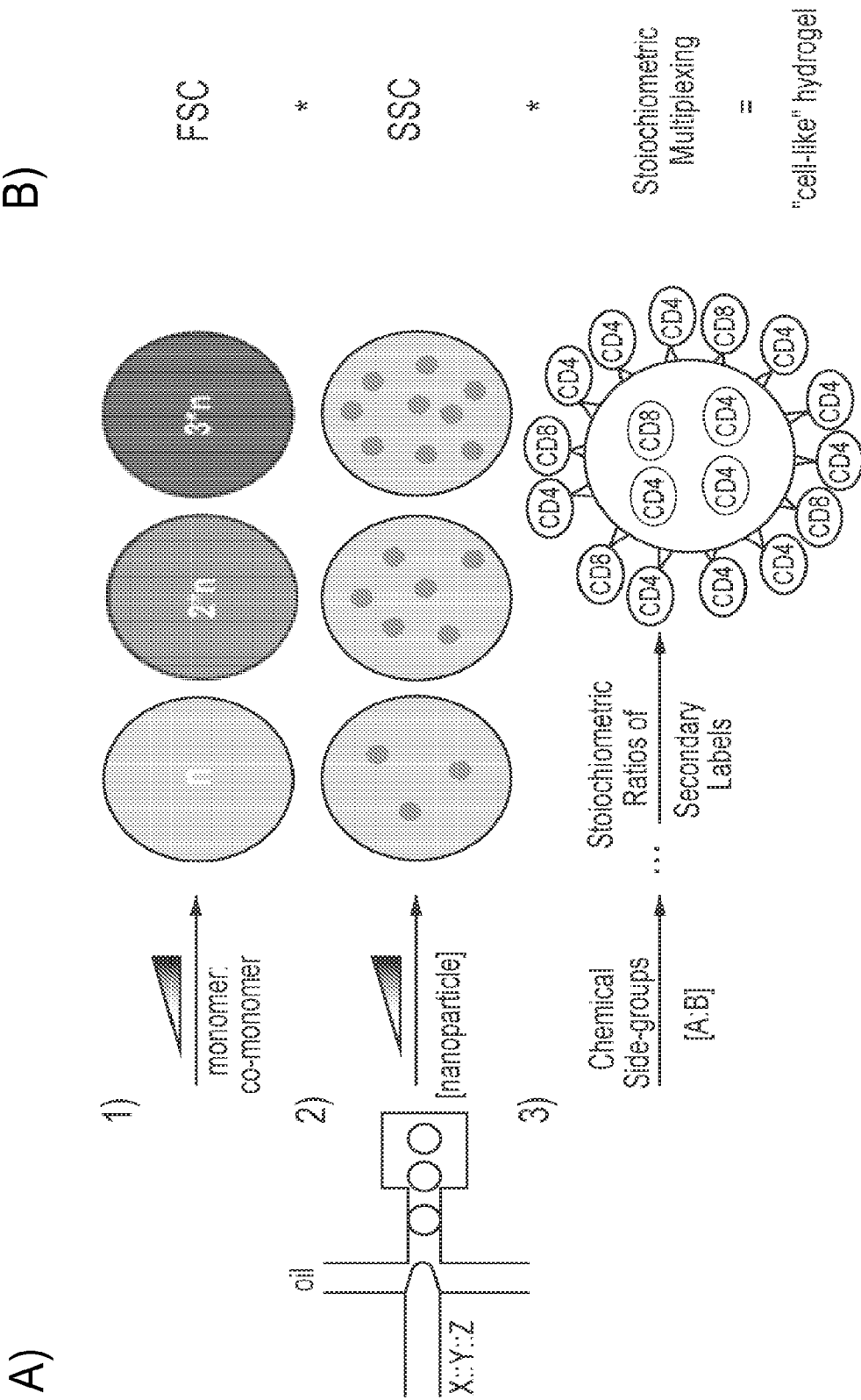

Forward scatter was modulated by adjusting the refractive index of the gel by adding co-monomers allyl acrylate and allyl methacrylate (see also FIGS. 11 and 12). Forward scatter can also be modulated with side scattering nanoparticles containing sufficient optical resolution/size/density including, but not limited to, higher density colloidal suspensions of silica and/or PMMA particles. Side scattering of the droplets was tuned by adding a colloidal suspension of silica nanoparticles and/or PMMA (poly(methyl methacrylate)) particles (~100 nm) to the central aqueous phase prior to polymerization (FIGS. 11 and 12).

In one embodiment, a bead, plurality of beads, biomolecule, or plurality of biomolecules is embedded (encapsulated) within the hydrogel particle. An encapsulated bead or biomolecule, in one embodiment, is employed to mimic one or more intracellular organelles of a target cell, or a cell after it engulfs a particle. In one embodiment, encapsulating or embedding a bead or biomolecule is accomplished at the time of hydrogel particle formation. For example, beads can be suspended in the appropriate concentration to allow for an average of one bead to be embedded/encapsulated in a single hydrogel particle. The bead suspension can be included, for example, within the aqueous solution of monomer. Similarly, a biomolecule or mixture of biomolecules can be incorporated into the aqueous solution of monomer to encapsulate the biomolecule or biomolecules.

Alternatively, once a hydrogel particle is formed, for example by the methods described above, in one embodiment, it can be further manipulated, for example, by embedding a bead, plurality of beads, biomolecule or plurality of biomolecules within the hydrogel particle.

Accordingly, in one aspect of the invention, a hydrogel comprising an embedded substance is provided.

In one embodiment, the embedded substance is an embedded molecule, for example a biomolecule. The biomolecule can be a single species or a plurality of different species. For example, a protein, peptide, carbohydrate, nucleic acid or combination thereof can be encapsulated within a hydrogel particle of the invention. Moreover, different nucleic acid molecules (e.g., of varying sequences or nucleic acid type such as genomic DNA, messenger RNA or DNA-RNA hybrids) can be encapsulated by the hydrogel particle of the invention. These can be comprised of any protein or nucleic acid as both forms of biological material contain labile chemical side-groups (or can be modified by commercial vendors (e.g., Integrated DNA Technology chemical side group modifications). Such side-groups are compatible with reaction chemistries commonly found in co-monomer compositions (e.g. acrylate chemistry, NHS-ester, primary amines, copper catalyzed click chemistry (Sharpless)). The range of possible embedded molecules which contain compatible chemistries is understood by those skilled in the art.

In one embodiment, different subpopulations of hydrogel particles are fabricated, each with a different concentration of biomolecule. In a further embodiment, the biomolecule is a nucleic acid, a protein, an intracellular ion such as calcium acid (or other biomolecule of the user's choosing, for example, calcium). In another embodiment, different subpopulations of hydrogel particles are fabricated, each with a different concentration of a drug substance. The drug substance in one embodiment is a biomolecule (i.e., a biologic, antibody, antibody drug conjugate, protein/enzyme, peptide, non-ribosomal peptide, or related molecule) or a small molecule synthetic drug (e.g., Type I/II/III polyketide, non-ribosomal peptide with bioactive properties, or other small molecule entity as generally classified by those skilled in the art).

In this regard, the present invention is particularly useful for determining assay resolution where cells are stained for their respective nucleic acid or protein content. In one embodiment, different populations of the hydrogel particles provided herein are encapsulated with known, differing amounts of an intracellular substance, e.g., nucleic acid or protein. Individual hydrogel particles are stained for the intracellular substance and fluorescence is measured via a cytometric device for the individual hydrogels of the various populations. This allows for a generation of a standard curve to establish the sensitivity and dynamic range of the intracellular assay. Once established, a sample can be run through the cytometer to detect target cell(s) if present, and to quantify the amount of intracellular substance in the respective target cell(s). In one embodiment, the embedded substance is an infectious disease biomarker, for example one of the infectious disease biomarkers in the Infectious Disease Biomarker Database (IDBD, see Yang et al. (2008) IDBD: Infectious Disease Biomarker Database. *Nucleic Acid Res.* 36, pp. D455-D460, incorporated by reference in its entirety for all purposes). In a further embodiment, the infectious disease biomarker is a biomarker of gastrointestinal infection, respiratory infection, neurological infection, urogenital infection, viral infection, hemorrhagic fever, zoonosis, arbovirus, antibiotics resistance or bioterrorism. In a further embodiment, the viral infection is an Ebola infection.

In one embodiment, the methods provided herein are used to determine the sensitivity and/or dynamic range of a cellular nucleic acid quantification assay. In this embodiment, a sample is interrogated for cell types within the sample (if present), and amount of cellular nucleic acid within the cell.

In another embodiment, the present invention provides a means for determining the resolution and/or sensitivity of an intracellular protein quantification assay. Hydrogel particles, in one embodiment, encapsulate known amounts of protein, at various concentrations, and subsequently stained with the appropriate protein antibody. Fluorescence is measured for the various particles to determine the sensitivity and/or dynamic range of the assay. The fluorescence values can then be compared to the values obtained from cells in a sample, to determine whether a target cell is present and whether it contains the intracellular protein, and the amount of the protein.

In one embodiment, individual hydrogel particles are tuned to have at least one optical property substantially similar to a circulating tumor cell or a fetal cell, present in maternal blood. The individual particles are embedded with known quantities of a biomolecule of interest. The particles are used to generate a standard curve for a biomolecule detection assay for the particular cell type.

As provided above, in one aspect of the invention, a hydrogel comprising an embedded substance is provided. In one embodiment, the embedded substance is a bead or plurality of beads. In one embodiment, a hydrogel particle is embedded with a single bead. In another embodiment, individual hydrogels the average number of embedded beads in a plurality of hydrogel particles is one.

In the case where a bead or plurality of beads are embedded into a hydrogel particle, in one embodiment, the optical properties of the bead or plurality of beads are used in combination with the FSC and SSC properties of the hydrogel particle for quality control of a flow cytometry assay. For example, the embedded bead in one embodiment is used as a control to calibrate the flow cytometer system, including the laser source, optics, and stream flow. In another embodiment, the embedded bead is used as a means for quantitating the amount of fluorescence in a sample, e.g., a particular cell. In this regard, embedded beads of various intensities can be used to generate a standard curve of fluorescence to determine whether a cell expresses a certain marker and at what level of expression.

In one embodiment, a bead with the diameter of about 1 µm to about 3 µm, about 2 µm to about 4 µm or about 3 µm to about 7 µm is embedded in a hydrogel provided herein. For example, in one embodiment, the bead has a diameter of about 3 µm to about 3.5 µm. In a further embodiment, the bead is a fluorescent bead. In another embodiment, the bead has a diameter of about 1 µm to about 2.5 µm or about 1.5 µm to about 3 µm. In a further embodiment, the bead is a fluorescent bead and can be stained either internally or at its surface. In even a further embodiment, the fluorescent bead is stained internally. Without wishing to be bound by theory, it is thought that internal staining insulates the fluorophores from environmental interactions that could cause variable fluorescence output.

As provided above, in one embodiment, the embedded bead is a fluorescence bead and in a further embodiment, the fluorescent bead is stained internally. It is within the skill in the art to select the appropriate fluorophore for use in conjunction with an embedded bead. In one embodiment, the bead is derivatized with one or more of the following fluorescent dyes: 6-carboxy-4',5'-dichloro-2',7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether, -alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2 ', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and -6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium Salaissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5,7-dimethyl-4-bora-3a,4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bom3a,4a-diaza-s-indacene-3-pentanoicacid succinimidyl ester; 4,4-difluoro-5,7-dimefhyl-4-bora-3a,4a-diaza-s-indacene-3propionicacid; 4,4-difluoro-5,7-dimethyl-4-bora-3a,4adiaza-s-indacene-3-propionicacid succinimidyl ester; 4,4difluoro-5,7-dimefhyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino)hexanoicacid; 6-((4,4-difluoro-5,7 dimethyl-4-bora-3a,4a-diaza-s-indacene-3-propionyl)amino)hexanoic acid or succinimidyl ester; N-(4,4-difluoro 5,7-dimethyl-4-bora-3a,4a-diaza-s-indacene-3- propionyl) cysteic acid, succinimidyl ester or triethylammonium salt; 6-4,4-difluoro-1,3-dimethyl-5-(4-methoxyphenyl)-4-bora3a,4a4,4-difluoro-5,7-diphenyl-4-bora-3a,4a-diaza-sindacene-3-propionicacid; 4,4-difluoro-5,7-diphenyl-4-bora3a, 4a-diaza-s-indacene-3-propionicacid succinimidyl ester; 4,4-difluoro-5-phenyl-4-bora-3a,4a-diaza-s-indacene-3-propionic acid; succinimidyl ester; 6-((4,4-difluoro-5-phenyl-4 bora-3a,4a-diaza-s-indacene-3-propionyl)amino) hexanoicacid or succinimidyl ester; 4,4-difluoro-5-(4-phenyl-1,3butadienyl)-4-bora-3a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bom-3a,4a-diaza-s-indacene-3-yl)styryloxy)acetyl)aminohexanoicacid or succinimidyl ester; 4,4-difluoro-5-styryl-4-bora-3a, 4a-diaza-s-indacene-3-propionic acid; 4,4-difluoro-5-styryl-4-bora-3a,4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4,4-difluoro-5-(2-thienyl)-4-bora-3a,4adiazas-indacene-3-yl)phenoxy)acetyl)amino)hexanoic acid or succinimidyl ester; and 6-(((4,4-difluoro-5-(2-thienyl)-4-bora-3a, 4a-diaza-s-indacene-3-yl)styryloxy)acetyl) aminohexanoic acid or succinimidyl ester, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid, cyanine dyes commercially available from Amersham-Pharmacia Biotech, including, but not limited to Cy3 NHS ester; Cy 5 NHS ester; Cy5.5 NHSester; and Cy7 NHS ester.

Other Fluorophores amenable for use with the present invention are provided in Table 2 below

TABLE 2

| ID | NAME | Alternate Names | Excitation | Emission | Vendor/Source | ACS CAS# |
|---|---|---|---|---|---|---|
| ISAC148 | 6-carboxyfluorescein | | 492 | 518 | PubChem | 3301-79-9 |
| ISAC1 | 6-JOE | | 520 | 550 | LifeTechnologies | 82855-40-1 |
| ISAC2 | 7-AAD | | 545 | 647 | LifeTechnologies | 7240-37-1 |
| ISAC3 | Acridine Orange | | 503 | 525 | LifeTechnologies | 65-61-2 |
| ISAC4 | Alexa Fluor 350 | AF350; 2H-1-Benzopyran-6-sulfonic acid, 7-amino-3-[2-[[(2,5-dioxo-1-pyrrolidinyl)oxy]-2-oxoethyl]-4-methyl-2-oxo-; 200554-19-4 | 343 | 442 | LifeTechnologies | 244636-14-4 |
| ISAC6 | Alexa Fluor 405 | AF405; C46H69N5O15S3 | 401 | 425 | LifeTechnologies | 791637-08-6 |
| ISAC7 | Alexa Fluor 430 | AF430; C32H42F3N3O9S | 433 | 541 | LifeTechnologies | 467233-94-9 |
| ISAC8 | Alexa Fluor 488 | AF488; C25H15Li2N3O13S2 | 496 | 519 | LifeTechnologies | 247144-99-6 |
| ISAC9 | Alexa Fluor 500 | AF500; CAS#798557-08-1 | 503 | 525 | LifeTechnologies | 798557-08-1 |
| ISAC10 | Alexa Fluor 514 | AF514; C31H27N3O13S2 | 517 | 542 | LifeTechnologies | 798557-07-0 |
| ISAC11 | Alexa Fluor 532 | AF532; 1H-Pyrano[3,2-f: 5,6-f']diindole-10,12-disulfonic acid, 5-[4-[[(2,5-dioxo-1-pyrrolidinyl)oxy]carbonyl]phenyl]-2,3,7,8-tetrahydro-2,3,3,7,7,8-hexamethyl-; 271795-14-3 | 532 | 553 | LifeTechnologies | 222159-92-4 |
| ISAC13 | Alexa Fluor 546 | AF546; C50H62Cl3N5O14S3 | 556 | 573 | LifeTechnologies | 247145-23-9 |
| ISAC14 | Alexa Fluor 555 | AF555 | 555 | 565 | LifeTechnologies | 644990-77-2 |
| ISAC15 | Alexa Fluor 568 | AF568 | 578 | 603 | LifeTechnologies | 247145-38-6 |
| ISAC16 | Alexa Fluor 594 | AF594 | 590 | 617 | LifeTechnologies | 247145-86-4 |
| ISAC17 | Alexa Fluor 610 | AF610; C58H77Cl3N6O14S3 | 612 | 628 | LifeTechnologies | 900528-62-3 |
| ISAC18 | Alexa Fluor 633 | AF633 | 632 | 647 | LifeTechnologies | 477780-06-6 |
| ISAC19 | Alexa Fluor 635 | AF635 | 633 | 647 | LifeTechnologies | 945850-82-8 |
| ISAC20 | Alexa Fluor 647 | AF647 | 650 | 665 | LifeTechnologies | 400051-23-2 |
| ISAC21 | Alexa Fluor 660 | AF660 | 663 | 690 | LifeTechnologies | 422309-89-5 |
| ISAC22 | Alexa Fluor 680 | AF680 | 679 | 702 | LifeTechnologies | 422309-67-9 |
| ISAC23 | Alexa Fluor 700 | AF700 | 702 | 723 | LifeTechnologies | 697795-05-4 |
| ISAC24 | Alexa Fluor 750 | AF750 | 749 | 775 | LifeTechnologies | 697795-06-5 |
| ISAC25 | Alexa Fluor 790 | AF790 | 784 | 814 | LifeTechnologies | 950891-33-5 |
| ISAC26 | AMCA | | 346 | 448 | SantaCruzBiotech | 106562-32-7 |
| ISAC27 | AmCyan | | 457 | 489 | BDBioscences | 1216872-44-4 |
| ISAC28 | APC | Allophycocyanin | 650 | 660 | SigmaAldrich | No names found |
| ISAC29 | APC-Alexa Fluor 680 | APC-AF680 | 655 | 704 | LifeTechnologies | No names found |
| ISAC30 | APC-Alexa Fluor 700 | APC-AF700 | 655 | 718 | LifeTechnologies | No names found |
| ISAC31 | APC-Alexa Fluor 750 | APC-AF750 | 650 | 775 | LifeTechnologies | No names found |
| ISAC32 | APC-Cy5.5 | Allophycocyanin-Cy5.5 | 650 | 695 | LifeTechnologies | No names found |
| ISAC33 | APC-Cy7 | Allophycocyanin-Cy7 | 650 | 767 | LifeTechnologies | No names found |
| ISAC34 | APC-eFluor 750 | eFluor750APC | 650 | 750 | eBioscience | No names found |
| ISAC35 | APC-eFluor 780 | eFluor780APC | 650 | 780 | eBioscience | 1472056-77-1 |
| ISAC36 | APC-H7 | H7APC | 650 | 765 | BDBioscences | 1366000-62-5 |
| ISAC37 | APC-Vio770 | Vio770APC | 652 | 775 | Miltenyl Biotech | No names found |
| ISAC38 | Atto488 | | 501 | 523 | ATTO-TEC | 923585-42-6 |
| ISAC39 | BIOTIN | | 0 | 0 | PubChem | 58-85-5 |
| ISAC40 | BODIPY FL | | 502 | 511 | SantaCruzBiotech | 165599-63-3 |

TABLE 2-continued

| ID | NAME | Alternate Names | Excitation | Emission | Vendor/Source | ACS CAS# |
|---|---|---|---|---|---|---|
| ISAC41 | BODIPY R6G | 4,4-difluoro-5-phenyl-4-bora-3a,4a-diaza-s-indacene-3-propionic acid, succinimidyl ester; C22H18BF2N3O4 | 527 | 547 | LifeTechnologies | 335193-70-9 |
| ISAC43 | Brilliant Violet 421 | BV421 | 406 | 423 | Biolegend | 1428441-68-2 |
| ISAC44 | Brilliant Violet 510 | BV510 | 405 | 510 | Biolegend | No names found |
| ISAC45 | Brilliant Violet 570 | BV570 | 407 | 571 | Biolegend | 1428441-76-2 |
| ISAC46 | Brilliant Violet 605 | BV605 | 407 | 603 | Biolegend | 1632128-60-9 |
| ISAC47 | Brilliant Violet 612 | BV612 | 0 | 0 | Biolegend | 1428441-91-1 |
| ISAC48 | Brilliant Violet 650 | BV650 | 407 | 647 | Biolegend | No names found |
| ISAC49 | Brilliant Violet 711 | BV711 | 405 | 711 | Biolegend | No names found |
| ISAC50 | Brilliant Violet 785 | BV785 | 405 | 786 | Biolegend | 1613592-44-1 |
| ISAC53 | Calcein | CAS#: 1461-15-0 | 493 | 514 | LifeTechnologies | 1461-15-0 |
| ISAC51 | Calcein AM | | 496 | 517 | PubChem | 148504-34-1 |
| ISAC52 | Calcein Blue AM | | 360 | 445 | PubChem | 168482-84-6 |
| ISAC54 | Calcein Violet AM | | 400 | 452 | LifeTechnologies | No names found |
| ISAC55 | Calcium Sensor Dye eFluor 514 | | 490 | 514 | eBioscience | No names found |
| ISAC56 | Cascade Blue | | 401 | 420 | PubChem | 1325-87-7 |
| ISAC57 | Cascade Yellow | | 400 | 550 | Synchem UG & Co. KG | 220930-95-0 |
| ISAC58 | Cell Proliferation Dye eFluor 450 | | 405 | 445 | eBioscience | No names found |
| ISAC59 | Cell Proliferation Dye eFluor 670 | | 652 | 672 | eBioscience | No names found |
| ISAC60 | CellTrace Violet Cell Proliferation | | 392 | 455 | LifeTechnologies | No names found |
| ISAC61 | CellVue Claret | | 655 | 657 | SigmaAldrich | 1042142-46-0 |
| ISAC62 | CFSE | | 492 | 525 | SantaCruzBiotech | 150347-59-4 |
| ISAC63 | CPC | O-cresolphthalein complexone | 488 | 660 | Chemical Book | 2411-89-4 |
| ISAC65 | Cy2 | | 492 | 507 | GElifesciences | 102185-03-5 |
| ISAC66 | Cy3 | | 552 | 566 | GElifesciences | 146368-16-3 |
| ISAC67 | Cy3.5 | | 581 | 598 | GElifesciences | 189767-45-1 |
| ISAC68 | Cy5 | | 633 | 670 | GElifesciences | 144377-05-9 |
| ISAC69 | Cy5.5 | | 677 | 695 | GElifesciences | 210892-23-2 |
| ISAC70 | Cy7 | | 743 | 767 | GElifesciences | 169799-14-8 |
| ISAC71 | Cychrome | | 565 | 667 | BDBioscences | 245670-67-1 |
| ISAC73 | CyQUANT DNA | | 502 | 522 | LifeTechnologies | No names found |
| ISAC74 | CyTRAK Orange | 1,5-bis{[2-(di-methylamino)ethyl]amino}-4,8-dihydroxyanthracene-9,10-dione | 514 | 609 | Abcam (eBioscience) | 1195771-25-5 |
| ISAC76 | DAPI | | 358 | 462 | PubChem | 47165-04-8 |
| ISAC77 | DCFH | | 505 | 525 | SigmaAldrich | 106070-31-9 |
| ISAC79 | DiA | DiA; 4-Di-16-ASP (4-(4-(Dihexadecylamino)styryl)-N-Methylpyridinium Iodide); C46H79IN2 | 455 | 586 | LifeTechnologies | 371114-38-4 |
| ISAC81 | DiD | DiD' solid; DiIC18(5) solid (1,1'-Dioctadecyl-3,3,3',3'-Tetramethylindodicarbocyanine, 4-Chlorobenzenesulfonate Salt); C67H103ClN2O3S | 647 | 669 | LifeTechnologies | 127274-91-3 |
| ISAC84 | DiI | DiI Stain (1,1'-Dioctadecyl-3,3,3',3'-Tetramethylindocarbocyanine Perchlorate ('DiI'; DiIC18(3))); C59H97ClN2O4; 3H-Indolium, 2-(3-(1,3-dihydro-3,3-dimethyl-1-octadecyl-2H-indol-2-ylidene)-1-propenyl)-3,3-dimethyl-1-octadecyl-, perchlorate/ | 550 | 568 | LifeTechnologies | 41085-99-8 |
| ISAC88 | DiO | DiO'; DiOC18(3) (3,3'-Dioctadecyloxacarbocyanine Perchlorate); C53H85ClN2O6; Benzoxazolium, 3-octadecyl-2-[3-(3-octadecyl-2(3H)-benzoxazolylidene)-1-propenyl]-, perchlorate/ | 489 | 506 | LifeTechnologies | 34215-57-1 |
| ISAC92 | DiR | DiR'; DiIC18(7) (1,1'-Dioctadecyl-3,3,3',3'-Tetramethylindotricarbocyanine Iodide); C63H101IN2 | 750 | 781 | LifeTechnologies | 100068-60-8 |
| ISAC95 | DRAQ5 | | 645 | 683 | CellSignallingTech | 254098-36-7 |
| ISAC96 | DRAQ7 | | 599 | 694 | CellSignallingTech | 1533453-55-2 |
| ISAC97 | DsRED | | 532 | 595 | Clontech | 469863-23-8 |
| ISAC98 | dsRed2-RFP | | 555 | 582 | Clontech | No names found |
| ISAC99 | DY547 | 547 Dyomics | 557 | 574 | Dynomics | 947138-67-2 |
| ISAC100 | DY634 | 634 Dyomics | 635 | 658 | Dynomics | 1189010-49-8 |
| ISAC101 | DY647 | 647 Dyomics | 650 | 665 | Dynomics | 890317-39-2 |
| ISAC102 | DyLight 350 | DL350 | 353 | 432 | PierceNet | 1436849-83-0 |
| ISAC103 | DyLight 405 | DL405 | 400 | 420 | PierceNet | 1051927-09-3 |
| ISAC104 | DyLight 488 | DL488 | 493 | 518 | PierceNet | 1051927-12-8 |
| ISAC105 | DyLight 549 | DL549 | 562 | 576 | JacksonImmunoRes | 1051927-13-9 |

TABLE 2-continued

| ID | NAME | Alternate Names | Excitation | Emission | Vendor/Source | ACS CAS# |
|---|---|---|---|---|---|---|
| ISAC106 | DyLight 550 | DL550 | 562 | 576 | PierceNet | 1340586-78-8 |
| ISAC107 | DyLight 594 | DL594 | 593 | 618 | PierceNet | 1268612-00-5 |
| ISAC108 | DyLight 633 | DL633 | 638 | 658 | PierceNet | 1051927-14-0 |
| ISAC109 | DyLight 649 | DL649 | 654 | 670 | JacksonImmunoRes | 1051927-15-1 |
| ISAC110 | DyLight 650 | DL650 | 652 | 672 | PierceNet | 1364214-13-0 |
| ISAC111 | DyLight 680 | DL680 | 682 | 712 | PierceNet | 1051927-24-2 |
| ISAC112 | DyLight 800 | DL800 | 777 | 794 | PierceNet | 1051927-23-1 |
| ISAC113 | EB | Ethidium Bromide | 523 | 604 | SigmaAldrich | 1239-45-8 |
| ISAC114 | ECD |  | 563 | 613 | LifeTechnologies | 88475-75-6 |
| ISAC116 | ECFP | enhanced cyan fluorescent protein | 435 | 477 | MyBiosource | No names found |
| ISAC118 | EdU | EdU(5-ethynyl-2\u2032-deoxyuridine); C11H12N2O5 | 0 | 0 | LifeTechnologies | 61135-33-9 |
| ISAC120 | EdU Alexa Fluor 488 |  | 496 | 516 | LifeTechnologies | No names found |
| ISAC121 | EdU Alexa Fluor 647 |  | 650 | 665 | LifeTechnologies | No names found |
| ISAC122 | EdU Pacific Blue |  | 405 | 455 | LifeTechnologies | No names found |
| ISAC123 | eFluor 450 |  | 400 | 450 | eBioscience | 1592653-87-6 |
| ISAC124 | eFluor 450 Fixable Viability Dye |  | 400 | 450 | eBioscience | No names found |
| ISAC125 | eFluor 490 |  | 350 | 490 | eBioscience | No names found |
| ISAC126 | eFluor 506 Fixable Viability Dye |  | 420 | 506 | eBioscience | No names found |
| ISAC127 | eFluor 525 |  | 350 | 525 | eBioscience | No names found |
| ISAC128 | eFluor 565 |  | 350 | 565 | eBioscience | No names found |
| ISAC129 | eFluor 585 |  | 350 | 604 | eBioscience | No names found |
| ISAC130 | eFluor 605 |  | 350 | 605 | eBioscience | 1248429-27-7 |
| ISAC131 | eFluor 615 |  | 590 | 622 | eBioscience | No names found |
| ISAC132 | eFluor 625 |  | 350 | 625 | eBioscience | No names found |
| ISAC133 | eFluor 650 |  | 350 | 650 | eBioscience | No names found |
| ISAC134 | eFluor 660 |  | 633 | 658 | eBioscience | 1634649-16-3 |
| ISAC135 | eFluor 670 |  | 0 | 0 | eBioscience | 1437243-07-6 |
| ISAC136 | eFluor 700 |  | 350 | 700 | eBioscience | No names found |
| ISAC137 | eFluor 710 |  | 350 | 710 | eBioscience | No names found |
| ISAC138 | eFluor 780 Fixable Viability Dye |  | 755 | 780 | eBioscience | No names found |
| ISAC139 | EGFP | enhanced green fluorescent protein | 480 | 510 | MyBiosource | No names found |
| ISAC141 | Emerald 300 |  | 289 | 530 | LifeTechnologies | No names found |
| ISAC142 | Eosin |  | 525 | 546 | SigmaAldrich | 17372-87-1 |
| ISAC143 | Ethidium Homodimer-1 |  | 528 | 617 | SigmaAldrich | 61926-22-5 |
| ISAC144 | Ethidium Monoazide EMA |  | 510 | 590 | SigmaAldrich | 58880-05-0 |
| ISAC145 | EYFP | enhanced yellow fluorescent protein | 515 | 528 | MyBiosource | No names found |
| ISAC147 | FAM |  | 492 | 518 | PubChem | 76823-03-5 |
| ISAC149 | FITC | Fluorescein | 500 | 520 | PubChem | 27072-45-3 |
| ISAC153 | Fluo-3 | C51H50Cl2N2O23; Glycine, N-[4-[6-[(acetyloxy)methoxy]-2,7-dichloro-3-oxo-3H-xanthen-9-yl]-2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-, (acetyloxy)methyl ester/ | 506 | 526 | LifeTechnologies | 123632-39-3 |
| ISAC155 | Fluo-4 | C51H50F2N2O23; Glycine, N-[4-[6-[(acetyloxy)methoxy]-2,7-difluoro-3-oxo-3H-xanthen-9-yl]-2-[2-[bis[2-[(acetyloxy)methoxy]-2-oxoethyl]amino]-5-methylphenoxy]ethoxy]phenyl]-N-[2-[(acetyloxy)methoxy]-2-oxoethyl]-, (acetyloxy)methyl ester/ | 494 | 516 | LifeTechnologies | 273221-59-3 |
| ISAC152 | FLMA | Fluorescein-5-maleimide | 495 | 520 | PierceNet | 75350-46-8 |
| ISAC157 | Fluoro-Emerald | Dextran, Fluorescein, 10,000 MW, Anionic, Lysine Fixable | 495 | 523 | LifeTechnologies | 194369-11-4 |
| ISAC159 | Fura Red |  |  |  | LifeTechnologies | 149732-62-7 |
| ISAC162 | Fura3 | Fura-2 LeakRes (AM) | 325 | 510 | SigmaAldrich | 172890-84-5 |
| ISAC164 | FxCycle Far Red |  | 640 | 658 | LifeTechnologies | No names found |
| ISAC165 | FxCycle Violet | C16H17Cl2N5; 1H-Indole-6-carboximidamide, 2-[4-(aminoiminomethyl)phenyl]-, dihydrochloride/ | 358 | 462 | LifeTechnologies | 28718-90-3 |
| ISAC167 | GFP | green fluorescent protein | 488 | 515 | MyBiosource | No names found |
| ISAC169 | GFP Violet Excited |  | 398 | 515 | MyBiosource | No names found |
| ISAC170 | GFP-Vex1 |  | 398 | 515 | MyBiosource | No names found |
| ISAC171 | HiLyte Fluor 488 |  | 501 | 527 | Anaspec | 1051927-29-7 |
| ISAC172 | HiLyte Fluor 555 |  | 550 | 566 | Anaspec | 1051927-30-0 |
| ISAC173 | HiLyte Fluor 647 |  | 649 | 674 | Anaspec | 925693-87-4 |
| ISAC174 | HiLyte Fluor 680 |  | 0 | 0 | Anaspec | 1051927-34-4 |
| ISAC175 | HiLyte Fluor 750 |  | 754 | 778 | Anaspec | 1051927-32-2 |

TABLE 2-continued

| ID | NAME | Alternate Names | Excitation | Emission | Vendor/Source | ACS CAS# |
|---|---|---|---|---|---|---|
| ISAC176 | Hoechst 33258 | | 345 | 455 | SigmaAldrich | 23491-45-4 |
| ISAC177 | Hoechst 33342 | bisBenzimide H 33342 trihydrochloride | 343 | 455 | SigmaAldrich | 23491-52-3 |
| ISAC179 | Hydroxycoumarin | C10H6O5; 7-hydroxycoumarin-3-carboxylic acid; 2H-1-Benzopyran-3-carboxylic acid, 7-hydroxy-2-oxo-/; 4-chloromethyl-7-hydroxycoumarin | 360 | 450 | LifeTechnologies | 43070-85-5 |
| ISAC183 | Indo-1 | Indo-1 AM Calcium Sensor Dye; C47H51N3O22; 1H-Indole-6-carboxylic acid, 2-[4-[bis[2-[(acetyloxy)methoxy]-2-oxoethyl]amino]-3-[2-[2-[bis[2-[(acetyloxy)methoxy]-2-oxoethyl]amino]-5-methylphenoxy]ethoxy]phenyl]-, (acetyloxy)methyl ester/ | 347 | 480 | LifeTechnologies | 96314-96-4 |
| ISAC187 | JC-1 | 5,5',6,6'-tetrachloro-1,1',3,3'-tetraethylbenzimidazolylcarbocyanine iodide; C25H27Cl4IN4 | 593 | 595 | LifeTechnologies | 3520-43-2 |
| ISAC189 | Krome Orange | | 398 | 530 | Beckman Coulter | 1558035-65-6 |
| ISAC190 | Leadmium | | 490 | 520 | LifeTechnologies | No names found |
| ISAC191 | LIVE/DEAD Fixable Aqua Dead Cell Stain | Aqua LIVE/DEAD | 367 | 526 | LifeTechnologies | No names found |
| ISAC193 | LIVE/DEAD Fixable Blue Dead Cell Stain | Blue LIVE/DEAD | 343 | 442 | LifeTechnologies | No names found |
| ISAC195 | LIVE/DEAD Fixable Far Red Dead Cell Stain | | 650 | 670 | LifeTechnologies | No names found |
| ISAC196 | LIVE/DEAD Fixable Green Dead Cell Stain | Green LIVE/DEAD | 498 | 525 | LifeTechnologies | No names found |
| ISAC198 | LIVE/DEAD Fixable Near-IR Dead Cell Stain | | 752 | 776 | LifeTechnologies | No names found |
| ISAC199 | LIVE/DEAD Fixable Red Dead Cell Stain | | 594 | 612 | LifeTechnologies | No names found |
| ISAC200 | LIVE/DEAD Fixable Violet Dead Cell Stain | Violet LIVE/DEAD | 403 | 455 | LifeTechnologies | No names found |
| ISAC202 | LIVE/DEAD Fixable Yellow Dead Cell Stain | Yellow LIVE/DEAD | 401 | 551 | LifeTechnologies | No names found |
| ISAC204 | Lucifer Yellow | C13H9Li2N5O9S2; 1H-Benz[de]isoquinoline-5,8-disulfonic acid, 6-amino-2-[(hydrazinocarbonyl)amino]-2,3-dihydro-1,3-dioxo-, dilithium salt/ | 428 | 544 | LifeTechnologies | 82446-52-4 |
| ISAC206 | Magnesium Green | C33H26Cl2K5N2O13; Glycine, N-[2-(carboxymethoxy)-4-[[(2',7'-dichloro-3',6'-dihydroxy-3-oxospiro[isobenzofuran-1(3H),9'-[9H]xanthen]-5-yl)carbonyl]amino]phenyl]-N-(carboxymethyl)-, pentapotassium salt/ | 507 | 531 | LifeTechnologies | 170516-41-3 |
| ISAC208 | Marina Blue | C16H11F2NO7; 2,5-Pyrrolidinedione, 1-[[[(6,8-difluoro-7-hydroxy-4-methyl-2-oxo-2H-1-benzopyran-3-yl)acetyl]oxy]-/; | 364 | 461 | LifeTechnologies | 215868-23-8 |
| ISAC210 | mBanana | | 540 | 553 | Clontech | 1114839-40-5 |
| ISAC211 | mCherry | | 587 | 610 | Clontech | 1628764-31-7 |
| ISAC212 | mCitrine | | 516 | 529 | Not Commercialized | 1357606-54-2 |
| ISAC213 | MethylCoumarin | AMCA-X, SE (6-((7-Amino-4-Methylcoumarin-3-Acetyl)amino)Hexanoic Acid, Succinimidyl Ester); C22H25N3O7 | 360 | 448 | LifeTechnologies | 1333-47-7 |
| ISAC216 | MitoTracker Green | C34H28Cl5N3O; Benzoxazolium, 2-[3-[5,6-dichloro-1,3-bis[[4-(chloromethyl)phenyl]methyl]-1,3-dihydro-2H-benzimidazol-2-ylidene]-1-propenyl]-3-methyl-, chloride/ | 490 | 512 | LifeTechnologies | 1304563-13-0 |
| ISAC218 | MitoTracker Orange | C24H24Cl2N2O | 550 | 575 | LifeTechnologies | No names found |
| ISAC219 | MitoTracker Red | C39H36Cl5N3 | 578 | 598 | LifeTechnologies | No names found |
| ISAC220 | mOrange | | 548 | 562 | Clontech | 1114839-60-9 |
| ISAC221 | mPlum | | 590 | 649 | Clontech | 1399820-93-9 |
| ISAC222 | mRaspberry | | 597 | 624 | Clontech | 1452799-41-5 |
| ISAC223 | mRFP1 | | 584 | 607 | Not Commercialized | 1452799-30-2 |
| ISAC224 | mStrawberry | | 574 | 596 | Clontech | 1114834-99-9 |
| ISAC225 | Na-Green | Sodium Green ™, tetra(tetramethylammonium) salt; C84H100Cl4N8O19 | 506 | 532 | LifeTechnologies | 195244-55-4 |
| ISAC228 | Nile Red | C20H18N2O2; 5H-Benzo[\u03B1]phenoxazin-5-one, 9-(diethylamino)-/ | 559 | 637 | LifeTechnologies | 7385-67-3 |
| ISAC230 | Oregon Green | | 491 | 519 | LifeTechnologies | 195136-58-4 |

TABLE 2-continued

| ID | NAME | Alternate Names | Excitation | Emission | Vendor/Source | ACS CAS# |
|---|---|---|---|---|---|---|
| ISAC232 | Oregon Green 488-X, succinimidyl ester | | 500 | 525 | LifeTechnologies | 890416-18-9 |
| ISAC233 | Oregon Green 514 | Oregon Green ® 514 carboxylic acid, succinimidyl ester; C26H12F5NO9S | 510 | 532 | LifeTechnologies | 198139-53-6 |
| ISAC235 | Pacific Blue | PacBlue; Pacific Blue ™succinimidyl ester; C14H7F2NO7 | 405 | 455 | LifeTechnologies | 215868-31-8 |
| ISAC236 | Pacific Blue succinimidyl ester | | 405 | 455 | LifeTechnologies | 215868-33-0 |
| ISAC237 | Pacific Orange | PacOrange | 403 | 551 | LifeTechnologies | 1122414-42-9 |
| ISAC240 | PE-Alexa Fluor 610 | RPE-AF610 | 563 | 628 | LifeTechnologies | No names found |
| ISAC241 | PE-Alexa Fluor 647 | RPE-AF647 | 567 | 669 | LifeTechnologies | No names found |
| ISAC242 | PE-Alexa Fluor 680 | RPE-AF680 | 570 | 702 | LifeTechnologies | No names found |
| ISAC243 | PE-Alexa Fluor 700 | RPE-AF700 | 563 | 720 | LifeTechnologies | No names found |
| ISAC244 | PE-Alexa Fluor 750 | RPE-AF750 | 570 | 776 | AbD Serotec | No names found |
| ISAC245 | PE-CF594 | PE-Dazzle 594 | 564 | 612 | BDBiosciences | 1613592-67-8 |
| ISAC72 | PE-Cy5 | | 565 | 667 | BDBiosciences | 1448849-77-1 |
| ISAC248 | PE-Cy5.5 | | 563 | 695 | AbD Serotec | No names found |
| ISAC249 | PE-Cy7 | | 563 | 760 | AbD Serotec | 1429496-42-3 |
| ISAC250 | PE-DY590 | | 563 | 599 | LSBio | No names found |
| ISAC251 | PE-DY647 | | 563 | 672 | LSBio | No names found |
| ISAC252 | PerCP | | 490 | 675 | AbD Serotec | 422551-33-5 |
| ISAC253 | PerCP-Cy5.5 | | 488 | 695 | AbD Serotec | 1474026-81-7 |
| ISAC254 | PerCP-eFluor 710 | | 488 | 710 | eBioscience | 1353683-31-4 |
| ISAC115 | PE-Texas Red | | 563 | 613 | LifeTechnologies | No names found |
| ISAC256 | PE-Vio770 | | 565 | 775 | Miltenyl Biotech | No names found |
| ISAC257 | pHrodo | pHrodo ™ Red, succinimidyl ester (pHrodo ™ Red, SE); pHrodo ™ Green STP Ester | 560 | 586 | LifeTechnologies | No names found |
| ISAC260 | pHrodo Green STP Ester | | 560 | 586 | LifeTechnologies | No names found |
| ISAC258 | pHrodo Red, succinimidyl ester | | 560 | 586 | LifeTechnologies | No names found |
| ISAC261 | Phycocyanin | | 617 | 646 | SigmaAldrich | 11016-15-2 |
| ISAC262 | PicoGreen | Quant-iT ™ PicoGreen ® dsDNA Reagent | 502 | 522 | LifeTechnologies | 177571-06-1 |
| ISAC264 | PKH2 | PKH2 Green Fluorescent Cell Linker | 490 | 504 | SigmaAldrich | 145687-07-6 |
| ISAC266 | PKH26 | PKH26 Red Fluorescent Cell Linker | 551 | 567 | SigmaAldrich | 154214-55-8 |
| ISAC268 | PKH67 | PKH67 Green Fluorescent Cell Linker | 490 | 504 | SigmaAldrich | 257277-27-3 |
| ISAC270 | POPO-1 | C41H54I4N6O2; Benzoxazolium, 2,2'-[1,3-propanediylbis[(dimethyliminio)-3,1-propanediyl-1(4H)-pyridinyl-4-ylidenemethylidyne]]bis[3-methyl]-, tetraiodide/ | 433 | 457 | LifeTechnologies | 169454-15-3 |
| ISAC272 | PO-PRO-1 | C20H27I2N3O; Benzoxazolium, 3-methyl-2-[[1-[3-(trimethylammonio)propyl]-4(1H)-pyridinylidene]methyl]-, diiodide/; | 435 | 457 | LifeTechnologies | 157199-56-9 |
| ISAC274 | Propidium Iodide | C27H34I2N4; Phenanthridinium, 3,8-diamino-5-[3-(diethylmethylammonio)propyl]-6-phenyl-, diiodide | 350 | 617 | LifeTechnologies | 25535-16-4 |
| ISAC276 | PURE | | 0 | 0 | Not Commercialized | No names found |
| ISAC277 | Pyronin Y | | 547 | 560 | SigmaAldrich | 92-32-0 |
| ISAC278 | Qdot 525 | | 350 | 525 | LifeTechnologies | 885332-45-6 |
| ISAC279 | Qdot 545 | | 350 | 545 | LifeTechnologies | 948906-89-6 |
| ISAC280 | Qdot 565 | | 350 | 565 | LifeTechnologies | 859509-02-7 |
| ISAC281 | Qdot 585 | | 350 | 585 | LifeTechnologies | 885332-46-7 |
| ISAC282 | Qdot 605 | | 350 | 605 | LifeTechnologies | 849813-89-4 |
| ISAC283 | Qdot 625 | | 350 | 625 | LifeTechnologies | 1144512-19-5 |
| ISAC284 | Qdot 655 | | 350 | 655 | LifeTechnologies | 674287-64-0 |
| ISAC285 | Qdot 705 | | 350 | 705 | LifeTechnologies | 885332-47-8 |
| ISAC286 | Qdot 800 | | 350 | 800 | LifeTechnologies | 885332-50-3 |
| ISAC287 | RD1 | R-Phycoerythrin | 563 | 578 | LifeTechnologies | 1376573-14-6 |
| ISAC295 | Rhodamine | | 550 | 570 | LifeTechnologies | No names found |
| ISAC290 | Rho 110 | Rhodamine 110 | 497 | 520 | LifeTechnologies | 13558-31-1 |
| ISAC293 | Rho 123 | Rhodamine 123 | 507 | 529 | LifeTechnologies | 62669-70-9 |
| ISAC296 | Rhodamine Green | Rhodamine Green ™carboxylic acid, succinimidyl ester, hydrochloride; C25H18ClN3O7 | 505 | 527 | LifeTechnologies | 189200-71-3 |
| ISAC297 | Rhodamine Green carboxylic acid, succinimidyl ester, hydrochloride | | 505 | 527 | LifeTechnologies | 254732-34-8 |
| ISAC298 | Rhodamine Red | | 573 | 591 | LifeTechnologies | 99752-92-8 |
| ISAC299 | Rhodamine Red-X | Rhodamine Red ™-X, succinimidyl ester; C37H44N4O10S2 | 570 | 576 | LifeTechnologies | 178623-12-6 |
| ISAC300 | Rhodamine Red-X, succinimidyl ester | | 570 | 576 | LifeTechnologies | 178623-13-7 |

TABLE 2-continued

| ID | NAME | Alternate Names | Excitation | Emission | Vendor/Source | ACS CAS# |
|---|---|---|---|---|---|---|
| ISAC301 | RiboFlavin | | 266 | 531 | SigmaAldrich | 83-88-5 |
| ISAC239 | R-Phycoerythrin | PE | 563 | 578 | LifeTechnologies | 11016-17-4 |
| ISAC303 | | SNARF-1 carboxylic acid, acetate, succinimidyl ester | 549 | 586 | LifeTechnologies | No names found |
| ISAC302 | SNARF-1 pH 6 | SNARF ®-1 carboxylic acid, acetate, succinimidyl ester; C33H24N2O9 | 549 | 586 | LifeTechnologies | No names found |
| ISAC304 | SNARF-1 pH 9 | | 576 | 640 | LifeTechnologies | No names found |
| ISAC305 | Spectral Red | | 506 | 665 | MyBiosource | No names found |
| ISAC306 | SureLight P1 | | 545 | 667 | Abcam (Columbia Biosciences) | No names found |
| ISAC307 | SureLight P3 | | 614 | 662 | Abcam | 1365659-06-8 |
| ISAC308 | SureLight PBXL-3 | | 614 | 662 | Abcam | No names found |
| ISAC309 | SYBR Green | | 498 | 522 | SigmaAldrich | 217087-73-5 |
| ISAC310 | SYTO 11 | | 506 | 526 | LifeTechnologies | 173080-67-6 |
| ISAC311 | SYTO 13 | | 488 | 506 | LifeTechnologies | 173080-69-8 |
| ISAC312 | SYTO 16 | | 488 | 520 | LifeTechnologies | 173080-72-3 |
| ISAC313 | SYTO 17 | | 618 | 637 | LifeTechnologies | 189233-66-7 |
| ISAC314 | SYTO 45 | | 450 | 486 | LifeTechnologies | 335078-86-9 |
| ISAC315 | SYTO 59 | | 622 | 643 | LifeTechnologies | 235422-34-1 |
| ISAC316 | SYTO 60 | | 650 | 681 | LifeTechnologies | 335079-14-6 |
| ISAC317 | SYTO 61 | | 618 | 651 | LifeTechnologies | 335079-15-7 |
| ISAC318 | SYTO 62 | | 650 | 681 | LifeTechnologies | 286951-08-4 |
| ISAC319 | SYTO 82 | | 540 | 560 | LifeTechnologies | 335079-10-2 |
| ISAC320 | SYTO 9 | | 482 | 500 | LifeTechnologies | 208540-89-0 |
| ISAC321 | SYTOX AADvanced | | 546 | 646 | LifeTechnologies | No names found |
| ISAC322 | SYTOX Blue | | 431 | 480 | LifeTechnologies | 396077-00-2 |
| ISAC323 | SYTOX Green | | 504 | 523 | LifeTechnologies | 194100-76-0 |
| ISAC324 | SYTOX Orange | | 547 | 570 | LifeTechnologies | 324767-53-5 |
| ISAC325 | SYTOX Red | | 640 | 658 | LifeTechnologies | 915152-67-9 |
| ISAC326 | tdTomato | | 554 | 581 | Clontech | 1114838-94-6 |
| ISAC334 | Tetramethylrhodamine | TMRho | 553 | 581 | LifeTechnologies | 70281-37-7 |
| ISAC329 | Texas Red | Texas Red ®-X, succinimidyl ester; C41H44N4O10S2 | 589 | 615 | LifeTechnologies | 82354-19-6 |
| ISAC330 | Texas Red-X, succinimidyl ester | | 589 | 615 | LifeTechnologies | 216972-99-5 |
| ISAC331 | Thiazole Orange | | 500 | 530 | SigmaAldrich | 107091-89-4 |
| ISAC332 | ThiolTracker Violet | | 406 | 526 | LifeTechnologies | No names found |
| ISAC335 | TO-PRO-1 | TO-PRO ®-1 iodide (515/531); C24H29I2N3S; Quinolinium, 4-[(3-methyl-2(3H)-benzothiazolylidene)methyl]-1-[3-(trimethylammonio)propyl]-, diiodide/; | 509 | 533 | LifeTechnologies | 157199-59-2 |
| ISAC338 | TO-PRO-3 | TO-PRO ®-3 iodide (642/661); C26H31I2N3S; Quinolinium, 4-[3-(3-methyl-2(3H)-benzothiazolylidene)-1-propenyl]-1-[3-(trimethylammonio)propyl]-, diiodide/ | 642 | 661 | LifeTechnologies | 157199-63-8 |
| ISAC341 | TOTO-1 | TOTO ®-1 iodide (514/533); C49H58I4N6S2; Quinolinium, 1-1'-[1,3-propanediylbis[(dimethyliminio)-3,1-propanediyl]]bis[4-[(3-methyl-2(3H)-benzothiazolylidene)methyl]]-, tetraiodide/ | 509 | 533 | LifeTechnologies | 143413-84-7 |
| ISAC344 | TOTO-3 | TOTO ®-3 iodide (642/660); C53H62I4N6S2 | 642 | 661 | LifeTechnologies | 166196-17-4 |
| ISAC346 | Tricolor | | 563 | 670 | LifeTechnologies | 478184-50-8 |
| ISAC347 | TRITC | Tetramethylrhodamine; tetramethylrhodamine-5-(and-6)-isothiocyanate; C25H21N3O3S; Xanthylium, 9-(2-carboxyisothiocyanatophenyl)-3,6-bis(dimethylamino)-, inner salt/ | 547 | 572 | LifeTechnologies | 745735-42-6 |
| ISAC351 | TruRed | | 490 | 695 | Not Commercialized | 396076-95-2 |
| ISAC352 | V19 | | 397 | 572 | Not Commercialized | No names found |
| ISAC353 | V450 | | 405 | 448 | BDBioscences | 1257844-82-8 |
| ISAC354 | V500 | | 415 | 500 | BDBioscences | 1333160-12-5 |
| ISAC355 | VioBlue | | 400 | 452 | Miltenyl Biotech | 1431147-59-9 |
| ISAC356 | VioGreen | | 388 | 520 | Miltenyl Biotech | No names found |
| ISAC357 | Vybrant DyeCycle Green | | 505 | 535 | LifeTechnologies | 1431152-50-9 |
| ISAC358 | Vybrant DyeCycle Orange | | 518 | 563 | LifeTechnologies | 1055990-89-0 |
| ISAC359 | Vybrant DyeCycle Ruby | | 637 | 686 | LifeTechnologies | 1345202-72-3 |
| ISAC360 | Vybrant DyeCycle Violet | | 370 | 436 | LifeTechnologies | 1015439-88-9 |

TABLE 2-continued

| ID | NAME | Alternate Names | Excitation | Emission | Vendor/Source | ACS CAS# |
|---|---|---|---|---|---|---|
| ISAC361 | YFP | Yellow Fluorescent Protein | 505 | 530 | Clontech | No names found |
| ISAC363 | YO-PRO-1 | YO-PRO ®-1 iodide (491/509); C24H29I2N3O | 491 | 506 | LifeTechnologies | 152068-09-2 |
| ISAC365 | YO-PRO-3 | YO-PRO ®-3 iodide (612/631); C26H31I2N3O; Quinolinium, 4-[3-(3-methyl-2(3H)-benzoxazolylidene)-1-propenyl]-1-[3-(trimethylammonio)propyl]-, diiodide/ | 613 | 629 | LifeTechnologies | 157199-62-7 |
| ISAC368 | YOYO-1 | YOYO ®-1 iodide (491/509); C49H58I4N6O2; | 491 | 509 | LifeTechnologies | 143413-85-8 |
| ISAC370 | YOYO-3 | YOYO ®-3 iodide (612/631); C53H62I4N6O2; Quinolinium, 1,1'-[1,3-propanediylbis[(dimethyliminio)-3,1-propanediyl]]bis[4-[3-(3-methyl-2(3H)-benzoxazolylidene)-1-propenyl]]-, tetraiodide/; | 613 | 629 | LifeTechnologies | 156312-20-8 |
| ISAC373 | ZsGreen | | 494 | 517 | Clontech | 1216871-88-3 |

Commercially available beads including, but not limited to, those sold by Bangs Laboratories, Inc, Sperhotech Inc., Thermo Scientific, Inc. and equivalent suppliers) can be used in combination with the hydrogel particles described herein. Depending on the assay, it is within the ordinary skill in the art to select a bead with the proper bead diameter, fluorescent emission and/or excitation spectrum and/or fluorescent intensity. For example, a quality control bead used in conjunction with a blue, red or UV laser can be embedded into one or more hydrogel particles provided herein. For example, an Alignflow™ flow cytometry alignment bead for blue lasers (catalog no. A-16500 (2.5 μm), A-16503 (6.0 μm)), red lasers (catalog no. A-16501 (2.5 μm), A-16504 (6.0 μm)) or UV lasers (catalog no. A-16502 (2.5 μm), A-16505 (6.0 μm)) can be embedded in on or more of the hydrogel particles provided herein.

In one embodiment, a fluorescent bead that can be excited at any wavelength from 365 nm-650 nm is embedded in a hydrogel particle. In one embodiment, the bead is a "rainbow particle" that contains a mixture of fluorophores, for example 4 fluorophores, 5 fluorophores, 6 fluorophores, seven fluorophores or eight fluorophores. In this regard, the user selects which wavelength to excite the particle, depending on the fluorophore being interrogated. Rainbow particles are commercially available, for example, from BD Biosciences (catalog nos. 556298 (mid range FL1 fluorescence), 556286 (6 color, 3.0-3.4 μm), 556288 (6 color, 6.0-6.4 μm), 559123 (8 color)) and Spherotech in various diameters (e.g., catalog nos. RCP20-5 (4 color), RCP-30-5 (6 peaks), RCP-30-5A (8 peaks)

A cell sorting set-up bead can be embedded in one or more of the hydrogel particles provided herein. In one embodiment, a cell sorting set-up beads approximates the size, emission wavelength, and intensity of a biological sample, and can be used to calibrate a flow cytometer's cell sorting system, including laser source, optics, and stream flow. In one embodiment, a cell sorting set-up beads is embedded in one or more hydrogel particles and is amenable for use with a UV, blue, green/yellow or red laser. Where a green laser is used, in one embodiment, the embedded bead is excited at 570 nm with emission of 575 nm, but may also be exited at 488 nm. Commercially available cell sorting set-up beads are available, for example, from Life Technologies (catalog nos. C-16506 (UV laser), C-16508 (blue laser), C-16509 (green-yellow laser), C-16507 (red laser)).

A compensation control bead can also be embedded in one or more of the hydrogel particles provided herein. Accurate compensation is an important parameter for effective multicolor analysis inflow cytometry. However, cellular-based compensation controls are not completely effective as many antigens are not highly expressed, and dimly stained cells can lead to inaccurate compensation settings.

A compensation control bead, in one embodiment, includes a fluorescent antibody conjugate capture capacity (positive compensation bead) or is inert (negative compensation bead). The compensation bead is mixed with a fluorophore-conjugated human, mouse, rat, hamster, or rabbit antibody; the two components provide a distinct high-signal positive control with an appropriate negative population that can then be used to set compensation properly regardless of the intensity of the cells in the actual experiment. Once the antibody is mixed with the bead, it is embedded in one or more of the hydrogel particles provided herein. Commercially available compensation beads are available, for example, from Life Technologies (catalog nos. A-10344, A-10389, A10497, A10513) and Spherotech (catalog nos. CMIg-P-08-2K, CMIg-P-30-2K, CMIg-P-50-3K, CMIg-P-70-3K).

In one embodiment, a hydrogel particle with an embedded/encapsulated bead is used as a reference for a cellular assay, for example, a phagocytosis assay cytoxicity assay, motility assay, viability assay, etc. Phagocytosis is the process by which a cell engulfs a solid particle to form an internal vesicle known as a phagosome. In this regard, a hydrogel particle can be tuned to have one or more optical properties substantially similar to a phagocyte, before and after the phagocyte engulfs a particle. Accordingly, in one embodiment, the hydrogel particles provided herein are used as control particles for a phagocytosis assay. In a further embodiment, (i) one or more of the optical properties of a hydrogel particle is substantially similar to a phagocyte prior to particle uptake and (ii) one or more of the optical properties of a second hydrogel particle is substantially similar to a phagocyte after to particle uptake. In this regard, a control is generated for measuring particle uptake by a phagocyte.

In one embodiment, the phagocyte is a professional phagocyte. In another embodiment, the phagocyte is a non-professional phagocyte (i.e., a cell that consumes dying cells and foreign organisms). In a further embodiment, the non-professional phagocyte is an epithelial cell, endothelial cell, fibroblast or mesenchymal cell. Hydrogel particles in one embodiment, are tuned to have one or more optical properties substantially similar to a professional phagocyte set forth in Table 3 below (prior to and/or after particle uptake).

TABLE 3

| Location | Phagocyte type |
| --- | --- |
| Blood | Neutrophil, monocyte |
| Bone marrow | Macrophage, monocyte, sinusoidal cell, lining cell |
| Bone tissue | Osteoclast |
| Gut and intestinal Peyer's patches | Macrophage |
| Connective tissue | Histiocyte, macrophage, monocyte, dendritic cell |
| Liver | Kupffer cell, monocyte |
| Lung | Self-replicating macrophage, monocyte, mast cell, dendritic cell |
| Lymphoid tissue | Free and fixed macrophages and monocytes, dendritic cell |
| Nervous tissue | Microglial cell (CD4+) |
| Spleen | Free and fixed macrophages, monocytes, sinusoidal cell |
| Thymus | Free and fixed macrophages, monocytes |
| Skin | Resident Langerhans cells, dendritic cells, conventional macrophage, mast cell |

In one embodiment, a plurality of hydrogel particles of the invention, embedded with a substance such as nucleic acid or a bead is used as control reagents for a genomic cytometry assay. In this regard, a specific number of copies of a particular chromosome, RNA sequence and/or DNA sequence can be mimicked by the embedded substance. The hydrogel particle can then be used as a control for a sample being probed for genetic information, such as the number of copies of a chromosome, the number of copies of an RNA sequence and/or the number of copies of an RNA sequence.

The three primary modes of deconvolution for flow cytometry are the two passive optical properties of a particle (forward scattering, FSC, corresponding to the refractive index, or RI; and side scattering, SSC) and biomarkers present on the surface of a given cell type. Therefore, compositions that allow hydrogel particles of the disclosure to mimic specific cell types with respect to these three modes are useful for providing synthetic, robust calibrants for flow cytometry.

In one embodiment, the refractive index (RI) of a disclosed hydrogel particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In another embodiment, the refractive index (RI) of a disclosed hydrogel particle is about 1.10 to about 3.0, or about 1.15 to about 3.0, or about 1.20 to about 3.0, or about 1.25 to about 3.0, or about 1.30 to about 3.0, or about 1.35 to about 3.0, or about 1.4 to about 3.0, or about 1.45 to about 3.0, or about 1.50 to about 3.0, or about 1.6 to about 3.0, or about 1.7 to about 3.0, or about 1.8 to about 3.0, or about 1.9 to about 3.0, or about 2.0 to about 3.0.

In some embodiments, the refractive index (RI) of a disclosed hydrogel particle is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

The SSC of a disclosed hydrogel particle is most meaningfully measured in comparison to that of target cell. In some embodiments, a disclosed hydrogel particle has an SSC within 30%, within 25%, within 20%, within 15%, within 10%, within 5%, or within 1% that of a target cell, as measured by a cytometric device.

The SSC of a hydrogel particle in one embodiment, is modulated by incorporating a high-refractive index molecule (or plurality thereof) in the hydrogel. In one embodiment, a high-refractive index molecule is provided in a hydrogel particle, and in a further embodiment, the high-refractive index molecule is colloidal silica, alkyl acrylate, alkyl methacrylate or a combination thereof. Thus in some embodiments, a hydrogel particle of the disclosure comprises alkyl acrylate and/or alkyl methacrylate. Concentration of monomer in one embodiment is adjusted to further adjust the refractive index of the hydrogel particle.

Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tertbutyl, 2-ethylhexyl, heptyl or octyl groups. The alkyl group may be branched or linear.

High-refractive index molecules can also include vinylarenes such as styrene and methylstyrene, optionally substituted on the aromatic ring with an alkyl group, such as methyl, ethyl or tert-butyl, or with a halogen, such as chlorostyrene.

In some embodiments, FSC is modulated by adjusting the percentage of monomer present in the composition thereby altering the water content present during hydrogel formation. In one embodiment, where a monomer and co-monomer are employed, the ratio of monomer and co-monomer is adjusted to change the hydrogel particle's forward scatter properties. This is shown in both FIG. 11 and FIG. 12.

The FSC of a disclosed hydrogel particle is most meaningfully measured in comparison to that of target cell. In some embodiments, a disclosed hydrogel particle has an FSC within 30%, within 25%, within 20%, within 15%, within 10%, within 5%, or within 1% that of a target cell, as measured by a cytometric device.

FSC is related to particle volume, and thus can be modulated by altering particle diameter, as described herein. Generally, it has been observed that large objects refract more light than smaller objects leading to high forward scatter signals (and vice versa). Accordingly, particle diameter in one embodiment is altered to modulate FSC properties of a hydrogel particle. For example, hydrogel particle diameter is increased in one embodiment is altered by harnessing larger microfluidic channels during particle formation.

SSC can be engineered by encapsulating nanoparticles within hydrogels to mimic organelles in a target cell. In some embodiments, a hydrogel particle of the disclosure comprises one or more types of nanoparticles selected from the group consisting of: polymethyl methacrylate (PMMA) nanoparticles, polystyrene (PS) nanoparticles, and silica nanoparticles. See also FIGS. 11 and 12 which show that addition of various concentrations of nanoparticles allow for the adjustment of side scatter of a particle. Without wishing to be bound by theory, the ability to selectively tune both forward and side scatter of a hydrogel, as described herein, allows for a robust platform to mimic a vast array of cell types.

Although the invention is mainly described with respect to the modification of optical properties, the invention is not limited thereto. For example, hydrogel particles can be fabricated and adjusted to tune the capacitance of the particles, e.g., to calibrate coulter counters. In one embodiment, a hydrogel particle's capacitance is adjusted by altering the amount of hydrogel monomer in the composition. For example, polyanaline, polyacetylene; polyphenylene vinylene; polypyrrole (X=NH) and polythiophene (X=S) co-monomers; and polyaniline (X=NH/N) and polyphenylene sulfide (X=S) co-monomer concentrations can all be adjusted to alter capacitance. In one embodiment, the concentration of one or more of these monomers is increased to increase the capacitance of the hydrogel particle.

In some embodiments, a hydrogel particle of the disclosure has material modulus properties (e.g., elasticity) more closely resembling that of a target cell as compared to a polystyrene bead of the same diameter.

After the hydrogel particle is formed, one or more of the particle's surfaces can be functionalized, for example, to mimic one or more optical properties of a target cell or a labeled target cell. The functionalized hydrogel particle can also include an embedded bead or substance such as a biomolecule, as described above. In one embodiment, one or more hydrogel particles are functionalized with one or more fluorescent dyes, one or more cell surface markers (or epitope binding regions thereof), or a combination thereof. In one embodiment, the hydrogel particle is formed by polymerizing at least one bifunctional monomer and after formation, the hydrogel particle includes one or more functional groups that can be used for further attachment of a cell surface marker, an epitope binding region of a cell surface marker, a fluorescent dye, or combination thereof. The free functional group, in one embodiment, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

A hydrogel particle can be functionalized with any fluorescent dye known in the art, including fluorescent dyes listed in The MolecularProbes® Handbook-A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the hydrogel, as discussed above.

Non-limiting examples of known fluorescent dyes that can be used to functionalize the surface of a hydrogel particle described herein include: 6-carboxy-4',5'-dichloro-2',7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxyfluoresceinsuccinimidyl ester; 6-carboxyfluorescein succinimidyl ester; 5-(and-6)-carboxyfluorescein succinimidyl ester; 5-(4,6-dichlorotriazinyl) amino fluorescein; 2 ', 7'-difluoro fluorescein; eosin-5-isothiocyanate; elythrosin5-isothiocyanate; 6-(fluorescein-5-carboxamido) hexanoic acid or succinimidyl ester; 6-(fluorescein-5-(and-6)-carboxamido)hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetmmethylrhodamine; 5-carboxytetramethylrhodamine succinimidyl ester; 6-carboxytetramethylrhodaminesuccinimidyl ester; 5-(and -6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium Salaissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate.

Other examples of fluorescent dyes for use with the hydrogel particles described herein include, but are not limited to, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5,7-dimethyl-4-bona-3a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora3a,4a-diaza-s-indacene-3-pentanoic acid succinimidyl ester; 4,4-difluoro-5,7-dimefhyl-4-bora-3a,4a-diaza-s-indacene-3propionicacid; 4,4-difluoro-5,7-dimethyl-4-bora-3a,4adiaza-s-indacene-3-propionicacid succinimidyl ester; 4,4difluoro-5,7-dimefhyl-4-bona-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino) hexanoic acid; 6-((4,4-difluoro-5,7 dimethyl-4-bora-3a,4a-diaza-s-indacene-3-propionyl) amino) hexanoic acid or succinimidyl ester; N-(4,4-difluoro 5,7-dimethyl-4-bora-3a,4a-diaza-s-indacene-3-propionyl) cysteic acid, succinimidyl ester or triethylammonium salt;

6-4,4-difluoro-1,3-dimethyl-5-(4-methoxyphenyl)-4-bora3a, 4a4,4-difluoro-5,7-diphenyl-4-bora-3a,4a-diaza-sindacene-3-propionicacid; 4,4-difluoro-5,7-diphenyl-4-bora3a,4a-diaza-s-indacene-3-propionic acid succinimidyl ester; 4,4-difluoro-5-phenyl-4-bora-3a,4a-diaza-s-indacene-3-propionic acid; succinimidyl ester; 6-((4,4-difluoro-5-phenyl-4 bora-3a,4a-diaza-s-indacene-3-propionyl)amino) hexanoicacid or succinimidyl ester; 4,4-difluoro-5-(4-phenyl-1,3butadienyl)-4-bora-3a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)aminohexanoicacid or succinimidyl ester; 4,4-difluoro-5-styryl-4-bora-3a,4a-diaza-s-indacene-3-propionic acid; 4,4-difluoro-5-styryl-4-bora-3a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionicacid succinimidyl ester; 4,4-difluoro-5-(2-thienyl)-4-bora-3a,4a-diaza-sindacene-3-propionicacid succinimidyl ester; 6-(((4-(4,4-difluoro-5-(2-thienyl)-4-bora-3a,4adiazas-indacene-3-yl)phenoxy)acetyl)amino)hexanoic acid or succinimidyl ester; and 6-(((4,4-difluoro-5-(2-thienyl)-4-bora-3a,4a-diaza-s-indacene-3-yl) styryloxy)acetyl) aminohexanoic acid or succinimidyl ester.

Fluorescent dyes for derivatization of the surface of one or more hydrogel particles in one embodiment, include, but are not limited to, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In another embodiment, fluorescent dyes for use with the hydrogel particles and methods described herein include cyanine dyes commercially available from Amersham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired spectral excitation and emission properties of the hydrogel particle.

Hydrogel particles, in one embodiment, are functionalized with one or more cell surface markers (see, e.g., Tables 4 and 7-8), or fragments thereof, for example, extracellular portions thereof in the case of transmembrane proteins, for example, by attaching the one or more cell surface markers, extracellular portions or ligand binding regions thereof to the particle via a free amine, free carboxyl and/or free hydroxyl group present on the surface of the hydrogel particle. Functionalization of a hydrogel particle with a dye or cell surface molecule can also occur through a linker, for example a streptavidin/biotin conjugate.

Depending on the target cell, individual hydrogel particles can be derivatized with one or more cell surface markers, or fragments thereof, for example, extracellular portions thereof in the case of transmembrane proteins to further mimic the structural properties of the target cell. Tables 4 and 7-8, provided below, sets forth a non-limiting list of cell surface markers that can be used to derivative hydrogel particles, depending on the target cell. Although the cell surface marker is provided, it is understood that a portion of the cell surface marker, for example, a receptor binding portion, a ligand binding portion, or an extracellular portion of the marker can be used to derivative the hydrogel particle (at the free functional group, as described above). See also FIGS. 11 and 12 which show that hydrogel surface modification with for example, a cell surface receptor, together with the selective tuning of FSC and/or SSC, allows for the fabrication of a hydrogel particle with the desired feature(s).

TABLE 4

| Target Cell | Cell Surface Marker(s) (human) | Cell Surface Marker(s) (mouse) |
|---|---|---|
| B Cell | CD19, CD20 | CD19, CD22 (B cell activation marker), CD45R/B220 |
| T Cell | CD3, CD4, CD8 | CD3, CD4, CD8 |
| Activated T Cells | CD25, CD69 | CD25, CD69 |
| Dendritic Cell | CD1c, CD83, CD123, CD141, CD209, MHC II | CD11c, CD123, MHC II |
| Plasmacytoid Dendritic Cells* | CD123, CD303, CD304 | CD11c$^{int}$, CD317 |
| Platelet (resting) | CD42b | CD41 |
| Platelet (activated) | CD62P | CD62P |
| Natural Killer Cells | CD16, CD56 | CD49b (clone DX5) |
| Hematopoietic Stem Cell | CD34, CD90 | CD48, CD117, CD150, Sca-1 |
| Macrophage | CD11b, CD68, CD163 | F4/80, CD68 |
| Monocyte | CD14, CD16, CD64 | CD11b, CD115, Ly-6C |
| Plasma Cell | CD138 | CD138 |
| Red Blood Cell | CD235a | TER-119 |
| Neutrophil | CD15, CD16 | CD11b, Ly-6B.2, Ly6G, Gr-1 |
| Basophil | 2D7 antigen, CD123, CD203c, FcεRIα | CD200R3, FcεRIα |
| Eosinophil | CD11b, CD193, EMR1, Siglec-8 | CD11b, CD193, F4/80, Siglec-F |
| Granulocyte | CD66b | CD66b, Gr-1/Ly6G, Ly6C |
| Endothelial cell | CD146 | CD146 MECA-32, CD106, CD31, CD62E (activated endothelial cell) |
| Epithelial cell | CD326 | CD326 (EPCAM1) |
| Natural Killer (NK) cell | CD56 | CD335 (NKp46) |
| Myeloid derived suppressor cell (MDSC) | CD11b, CD14, CD33 (Siglec-3) | CD11b, GR1 |

Cell types including but not limited to various cell lines such as CHO, HEK-293, BHK-21, NS0, MDCK, VERO, MRC-S, W1-38 and Sp2/0 Mouse Myeloma (hybridomas). Table 5 and Table 6 each provides other cell types for use with the hydrogel particles described herein.

TABLE 5 keratinocyte of epidermis
basal cell of epidermis
keratinocyte of fingernails and toenails
basal cell of nail bed
hair shaft cells
medullary hair shaft cells
cortical hair shaft cells
cuticular hair shaft cells
hair-root sheath cells
cuticular hair-root sheath cells
hair-root sheath cells of Huxley's layer
hair-root sheath cells of Henle's layer
external hair-root sheath cells
hair matrix cell (stem cell)
surface epithelial cell of stratified squamous epithelium of tongue
surface epithelial cell of stratified squamous epithelium of oral cavity
surface epithelial cell of stratified squamous epithelium of esophagus
surface epithelial cell of stratified squamous epithelium of anal canal
surface epithelial cell of stratified squamous epithelium of distal urethra
surface epithelial cell of stratified squamous epithelium of vagina
basal cell of these epithelia TABLE 5-continued cell of urinary epithelium
cells of salivary gland
Mucous cells of salivary gland
Serous cell of salivary gland
cell of von Ebner's gland in tongue
cell of mammary gland
cell of lacrimal gland
cell of ceruminous gland of ear
cell of eccrine sweat gland
cell of eccrine sweat gland
cell of apocrine sweat gland
cell of gland of Moll in eyelid
cell of sebaceous gland
cell of Bowman's gland in nose
cell of Brunner's gland in duodenum
cell of seminal vesicle
cell of prostate gland
cell of bulbourethral gland
cell of Bartholin's gland
cell of gland of Littre
cell of endometrium of uterus
isolated goblet cell of respiratory and digestive tracts
mucous cell of lining of stomach
zymogenic cell of gastric gland
oxyntic cell of gastric gland
acinar cell of pancreas
Paneth cell of small intestine
type II pneumocyte of lung
Clara cell of lung
cells of anterior pituitary
cell of intermediate pituitary
cells of posterior pituitary
cells of gut and respiratory tract
cells of thyroid gland
cells of parathyroid gland
cells of adrenal gland
steroid hormones
cells of gonads
cells of juxtaglomerular apparatus of kidney
juxtaglomerular cell
macula
densa cell
peripolar cell
mesangial cell
brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
hepatocyte
white fat cell
brown fat cell
lipocyte of liver
type I pneumocyte
pancreatic duct cell
parietal cell of kidney glomerulus
podocyte of kidney glomerulus
cell of thin segment of loop of Henle
collecting duct cell (in kidney)
duct cell of seminal vesicle
duct cell of prostate gland
vascular endothelial cells of blood vessels and lymphatics
fenestrated vascular endothelial cells
continuous vascular endothelial cells
splenic vascular endothelial cells
synovial cell
serosal cell
squamous cell lining perilymphatic space of ear
cells lining endolymphatic space of ear
squamous cell
columnar cells of endolymphatic sac
"dark" cell
vestibular membrane cell
stria vascularis basal cell
stria vascularis marginal cell
cell of Claudius
cell of Boettcher TABLE 5-continued choroid plexus cell
squamous cell of pia-arachnoid
cells of ciliary epithelium of eye
corneal "endothelial" cell
Ciliated Cells of respiratory tract
Ciliated Cells of oviduct and of endometrium of uterus
Ciliated Cells of rete testis and ductulus efferens
Ciliated Cells of central nervous system
epithelial
ameloblast
nonepithelial
chondrocytes
osteoblast/osteocyte
osteoprogenitor cell
hyalocyte of vitreous body of eye
stellate cell of perilymphatic space of ear
skeletal muscle cells
heart muscle cells
smooth muscle cells (various)
myoepithelial cells
red blood cell
megakaryocyte
macrophages and related cells
neutrophil
eosinophil
basophil
mast cell
T lymphocyte
B lymphocyte
photoreceptors (rods, cones, and can be blue sensitive, green sensitive, red sensitive)
inner hair cell of organ of Corti
outer hair cell of organ of Corti
type I hair cell of vestibular apparatus of ear
type II hair cell of vestibular apparatus of ear
type II taste bud cell
olfactory neuron
basal cell of olfactory epithelium
carotid body cell type I
carotid body cell type II
Merkel cell of epidermis
primary sensory neurons specialized for touch (various)
primary sensory neurons specialized for temperature - cold sensitive
primary sensory neurons specialized for temperature - heat sensitive
primary sensory neurons specialized for pain (various)
proprioceptive primary sensory neurons (various)
Autonomic Neurons
inner pillar cell
outer pillar cell
inner phalangeal cell
outer phalangeal cell
border cell
Hensen cell
supporting cell of vestibular apparatus
supporting cell of taste bud (type I taste bud cell)
supporting cell of olfactory epithelium
Schwann cell
satellite cell (encapsulating peripheral nerve cell bodies)
enteric glial cell
neurons
glial cells
anterior lens epithelial cell
lens fiber (crystallin-containing cell)
melanocyte
retinal pigmented epithelial cell
oogonium/oocyte
spermatocyte
spermatogonium (stem cell for spermatocyte)
ovarian follicle cell
Sertoli cell (in testis)
thymus epithelial cell
Salivary gland mucous cell
Salivary gland number 1
Von Ebner's gland cell in tongue
Mammary gland cell
Lacrimal gland cell
Ceruminous gland cell in ear
Eccrine sweat gland dark cell
Eccrine sweat gland clear cell
Apocrine sweat gland cell TABLE 5-continued Gland of Moll cell in eyelid
Sebaceous gland cell
Bowman's gland cell in nose
Brunner's gland cell in duodenum
Seminal vesicle cell
Prostate gland cell
Bulbourethral gland cell
Bartholin's gland cell
Gland of Littre cell
Uterus endometrium cell
goblet cell of respiratory and digestive tracts
Stomach lining mucous cell
Gastric gland zymogenic cell
Gastric gland oxyntic cell
Pancreatic acinar cell
Paneth cell of small intestine
pneumocyte of lung
Clara cell of lung
anterior pituitary cells
Somatotropes
Lactotropes
Thyrotropes
Gonadotropes
Corticotropes
melanocyte-stimulating hormone
Magnocellular neurosecretory cells secreting:
Gut and respiratory tract cells secreteing:
Thyroid gland cells
thyroid epithelial cell
parafollicular cell
Parathyroid gland cells
Parathyroid chief cell
Oxyphil cell
Adrenal gland cells
chromaffin cells
secreting steroid hormones (mineralcorticoids and gluco corticoids)
Leydig cell of testes secreting testosterone
Theca interna cell of ovarian follicle secreting estrogen
Corpus luteum cell of ruptured ovarian follicle secreting progesterone
Granulosa lutein cells
Theca lutein cells
Juxtaglomerular cell (renin secretion)
Macula densa cell of kidney
Peripolar cell of kidney
Mesangial cell of kidney
epidermal keratinocyte
Epidermal basal cell
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell
Hair matrix cell (stem cell)
epithelial cell of stratified squamous epithelium of cornea,
epithelial cell of stratified squamous epithelium of tongue
epithelial cell of stratified squamous epithelium of oral cavity
epithelial cell of stratified squamous epithelium of esophagus
epithelial cell of stratified squamous epithelium of anal canal
epithelial cell of stratified squamous epithelium of distalurethra
epithelial cell of stratified squamous epithelium of vagina
basal cell (stem cell) of epithelia of cornea
basal cell (stem cell) of epithelia of tongue
basal cell (stem cell) of epithelia of oral cavity
basal cell (stem cell) of epithelia of esophagus
basal cell (stem cell) of epithelia of anal canal
basal cell (stem cell) of epithelia of distal urethra
basal cell (stem cell) of epithelia of vagina
Urinary epithelium cell
Auditory inner hair cell of organ of Corti
Auditory outer hair cell of organ of Corti
basal cell of olfactory epithelium
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor cells of retina in eye:
Photoreceptor rod cells
Photoreceptor blue-sensitive cone cell of eye
Photoreceptor green-sensitive cone cell of eye
Photoreceptor red-sensitive cone cell of eye
Proprioceptive primary sensory neurons
Touch-sensitive primary sensory neurons
Type I carotid body cell
Type II carotid body cell
Type I hair cell of vestibular system of ear
Type II hair cell of vestibular system of ear
Type I taste bud cell
Cholinergic neural cell
Adrenergic neural cell
Peptidergic neural cell
Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Taste bud supporting cell
Olfactory epithelium supporting cell
Schwann cell
Satellite glial cell
Enteric glial cell
Astrocyte
Neuron cells
Oligodendrocyte
Spindle neuron
Anterior lens epithelial cell
Crystallin-containing lens fiber cell
Hepatocyte
Adipocytes (white fat cell, brown fat cell, liver lipocyte)
Kidney parietal cell
Kidney glomerulus podocyte
Kidney proximal tubule brush border cell
Loop of Henle thin segment cell
Kidney distal tubule cell
Kidney collecting duct cell
Type I pneumocyte
Pancreatic duct cell
Nonstriated duct cell
principal cell
Intercalated cell
Duct cell
Intestinal brush border cell
Exocrine gland striated duct cell
Gall bladder epithelial cell
Ductulus efferens nonciliated cell
Epididymal principal cell
Epididymal basal cell
Ameloblast epithelial cell
Planum semilunatum epithelial cell of vestibular system of ear
Organ of Corti interdental epithelial cell
Loose connective tissue fibroblasts
Corneal fibroblasts (corneal keratocytes)
Tendon fibroblasts
Bone marrow reticular tissue fibroblasts
nonepithelial fibroblasts
Pericyte
Nucleus pulposus cell of intervertebral disc
Cementoblast/cementocyte
Odontoblast/odontocyte
Hyaline cartilage chondrocyte
Fibrocartilage chondrocyte
Elastic cartilage chondrocyte
Osteoblast/osteocyte
Osteoprogenitor cell
Hyalocyte of vitreous body of eye
Stellate cell of perilymphatic space of ear
Hepatic stellate cell (Ito cell)
Pancreatic stelle cell
skeletal muscle Cell
Red skeletal muscle cell (slow)
White skeletal muscle cell (fast)
Intermediate skeletal muscle cell
nuclear bag cell of muscle spindle
nuclear chain cell of muscle spindle TABLE 5-continued Satellite cell (stem cell)
Heart muscle cells
Ordinary heart muscle cell
Nodal heart muscle cell
Purkinje fiber cell
Smooth muscle cell
Myoepithelial cell of iris
Myoepithelial cell of exocrine glands
Erythrocyte
Megakaryocyte
Monocyte
Connective tissue macrophage
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Hybridoma cell
Mast cell
Helper T cell
Suppressor T cell
Cytotoxic T cell
Natural Killer T cell
B cell
Natural killer cell
Reticulocyte
Stem cells and committed progenitors for the blood and immune system (various types)
Oogonium/Oocyte
Spermatid
Spermatocyte
Spermatogonium cell
Spermatozoon
Ovarian follicle cell
Sertoli cell (in testis)
Thymus epithelial cell
Interstitial kidney cells

TABLE 6

Keratinizing Epithelial Cells keratinocyte of epidermis (= differentiating epidermal cell)
basal cell of epidermis (stem cell)
keratinocyte of fingernails and toenails
basal cell of nail bed (stem cell)
hair shaft cells
  medullary
  cortical
  cuticular
hair-root sheath cells
Cuticular root sheath cells
root sheath cells of Huxley's layer
root sheath cells of Henle's layer
external root sheath cells
hair matrix cell (stem cell)
Cells of Wet Stratified Barrier Epithelia surface epithelial cell of stratified squamous epithelium of cornea, tongue, oral cavity, esophagus, anal canal, distal urethra, vagina
basal cell of these epithelia (stem cell)
cell of urinary epithelium (lining bladder and urinary ducts)
Epithelial Cells Specialized for Exocrine Secretion cells of salivary gland
  mucous cell (secretion rich in polysaccharide)
  serous cell (secretion rich in glycoprotein enzymes)
cell of von Ebner's gland in tongue (secretion to wash over taste buds)
cell of mammary gland, secreting milk
cell of lacrimal gland, secreting tears
cell of ceruminous gland of ear, secreting wax
cell of eccrine sweat gland, secreting glycoproteins (dark cell)
cell of eccrine sweat gland, secreting small molecules (clear cell)
cell of apocrine sweat gland (odoriferous secretion, sex-hormone sensitive)
cell of gland of Moll in eyelid (specialized sweat gland)

TABLE 6-continued cell of sebaceous gland, secreting lipid-rich sebum
cell of Bowman's gland in nose (secretion to wash over olfactory epithelium)
cell of Brunner's gland in duodenum, secreting alkaline solution of mucus and enzymes
cell of seminal vesicle, secreting components of seminal fluid, including fructose (as fuel for swimming sperm)
cell of prostate gland, secreting other components of seminal fluid
cell of bulbourethral gland, secreting mucus
cell of Bartholin's gland, secreting vaginal lubricant
cell of gland of Littre, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung (function unknown)
Cells Specialized for Secretion of Hormones cells of anterior pituitary, secreting growth hormone, follicle-stimulating hormone, luteinizing hormone, prolactin, adrenocorticotropic hormone, and/or thyroid-stimulating hormone
cell of intermediate pituitary, secreting melanocyte-stimulating hormone
cells of posterior pituitary, secreting oxytocin and/or vasopressin
cells of gut and respiratory tract, secreting serotonin, endorphin, somatostatin, gastrin, secretin, cholecystokinin, insulin, glucagon, and/or bombesin
cells of thyroid gland, secreting
  thyroid hormone
  calcitonin
cells of parathyroid gland, secreting
  parathyroid hormone
  oxyphil cell (function unknown)
cells of adrenal gland, secreting
  epinephrine
  norepinephrine
  steroid hormones
    mineralocorticoids
    glucocorticoids
cells of gonads, secreting
  testosterone (Leydig cell of testis)
  estrogen (theca interna cell of ovarian follicle)
  progesterone (corpus luteum cell of ruptured ovarian follicle)
cells of juxtaglomerular apparatus of kidney
juxtaglomerular cell (secreting renin)
  macula densa cell    (uncertain but probably related in function;
  peripolar cell    possibly involved in secretion of
  mesangial cell    erythropoietin)
Epithelial Absorptive Cells in Gut, Exocrine Glands, and Urogenital Tract brush border cell of intestine (with microvilli)
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte (liver cell)
fat cells
  white fat
  brown fat
  lipocyte of liver
Epithelial Cells Serving Primarily a Barrier Function, Lining the Lung, Gut, Exocrine Glands, and Urogenital Tract type I pneumocyte (lining air space of lung)
pancreatic duct cell (centroacinar cell)
nonstriated duct cell of sweat gland, salivary gland, mammary gland, etc. (various)
parietal cell of kidney glomerulus
podocyte of kidney glomerulus
cell of thin segment of loop of Henle (in kidney)
collecting duct cell (in kidney)
duct cell of seminal vesicle, prostate gland, etc. (various)

TABLE 6-continued

Epithelial Cells Lining Closed Internal Body Cavities vascular endothelial cells of blood vessels and lymphatics
    fenestrated
    continuous
    splenic
synovial cell (lining joint cavities, secreting largely hyaluronic acid)
serosal cell (lining peritoneal, pleural, and pericardial cavities)
squamous cell lining perilymphatic space of ear
cells lining endolymphatic space of ear
    squamous cell
    columnar cells of endolymphatic sac
        with microvilli
        without microvilli
    "dark" cell
    vestibular membrane cell
    stria vascularis basal cell
    stria vascularis marginal cell
    cell of Claudius
    cell of Boettcher
choroid plexus cell (secreting cerebrospinal fluid)
squamous cell of pia-arachnoid
cells of ciliary epithelium of eye
    pigmented
    nonpigmented
corneal "endothelial" cell Ciliated Cells with Propulsive Function Ciliated Cells of respiratory tract
Ciliated Cells of oviduct and of endometrium of uterus (in female)
Ciliated Cells of rete testis and ductulus efferens (in male)
Ciliated Cells of central nervous system (ependymal cell lining brain cavities)

Cells Specialized for Secretion of Extracellular Matrix epithelial
    ameloblast (secreting enamel of tooth)
    plenum semilunatum cell of vestibular apparatus of ear
        (secreting proteoglycan)
    interdental cell of organ of Corti (secreting tectorial "membrane" covering
    hair cells of organ of Corti)
nonepithelial (connective tissue)
    fibroblasts (various-of loose connective tissue, of cornea, of tendon, of reticular tissue of bone marrow, etc.)
    pericyte of blood capillary
    nucleus pulposus cell of intervertebral disc
    cementoblast/cementocyte (secreting bonelike cementum of root of tooth)
    odontoblast/odontocyte (secreting dentin of tooth)
    chondrocytes
        of hyaline cartilage
        of fibrocartilage
        of elastic cartilage
    osteoblast/osteocyte
    osteoprogenitor cell (stem cell of osteoblasts)
    hyalocyte of vitreous body of eye
    stellate cell of perilymphatic space of ear Contractile Cells skeletal muscle cells
    red (slow)
    white (fast)
    intermediate
    muscle spindle-nuclear bag
    muscle spindle-nuclear chain
    satellite cell (stem cell)
heart muscle cells
    ordinary
    nodal
    Purkinje fiber
smooth muscle cells (various)
myoepithelial cells
    of iris
    of exocrine glands Cells of Blood and Immune System red blood cell
megakaryocyte
macrophages and related cells
    monocyte
    connective-tissue macrophage (various)
    Langerhans cell (in epidermis)
    osteoclast (in bone)
    dendritic cell (in lymphoid tissues)
    microglial cell (in central nervous system)
neutrophil
eosinophil
basophil
mast cell
T lymphocyte
    helper T cell
    suppressor T cell
    killer T cell
B lymphocyte
    IgM
    IgG
    IgA
    IgE
killer cell
stem cells and committed progenitors for the blood and immune system (various)

Sensory Transducers photoreceptors
    rod
    cones
        blue sensitive
        green sensitive
        red sensitive
hearing
    inner hair cell of organ of Corti
    outer hair cell of organ of Corti
acceleration and gravity
    type I hair cell of vestibular apparatus of ear
    type II hair cell of vestibular apparatus of ear
taste
    type II taste bud cell
smell
    olfactory neuron
    basal cell of olfactory epithelium (stem cell for olfactory neurons)
blood pH
    carotid body cell
        type I
        type II
touch
    Merkel cell of epidermis
    primary sensory neurons specialized for touch (various)
temperature
    primary sensory neurons specialized for temperature
        cold sensitive
        heat sensitive
pain
    primary sensory neurons specialized for pain (various)
configurations and forces in musculoskeletal system
    proprioceptive primary sensory neurons (various)

Autonomic Neurons cholinergic (various)
adrenergic (various)
peptidergic (various)

Supporting Cells of Sense Organs and of Peripheral Neurons supporting cells of organ of Corti
inner pillar cell
    outer pillar cell
    inner phalangeal cell
    outer phalangeal cell
    border cell
    Hensen cell
supporting cell of vestibular apparatus
supporting cell of taste bud (type I taste bud cell)
supporting cell of olfactory epithelium
Schwann cell
satellite cell (encapsulating peripheral nerve cell bodies)
enteric glial cell Neurons and Glial Cells of Central Nervous System neurons (huge variety of types-still poorly classified)
glial cells TABLE 6-continued astrocyte (various)
oligodendrocyte
Lens Cells anterior lens epithelial cell
lens fiber (crystallin-containing cell)
Pigment Cells melanocyte
retinal pigmented epithelial cell
Germ Cells oogonium/oocyte
spermatocyte
spermatogonium (stem cell for spermatocyte)
Nurse Cells ovarian follicle cell
Sertoli cell (in testis)
thymus epithelial cell
Exocrine secretory epithelial cells Salivary gland mucous cell (polysaccharide-rich secretion)
Salivary gland number 1 (glycoprotein enzyme-rich secretion)
Von Ebner's gland cell in tongue (washes taste buds)
Mammary gland cell (milk secretion)
Lacrimal gland cell (tear secretion)
Ceruminous gland cell in ear (earwax secretion)
Eccrine sweat gland dark cell (glycoprotein secretion)
Eccrine sweat gland clear cell (small molecule secretion)
Apocrine sweat gland cell (odoriferous secretion, sex-hormone sensitive)
Gland of Moll cell in eyelid (specialized sweat gland)
Sebaceous gland cell (lipid-rich sebum secretion)
Bowman's gland cell in nose (washes olfactory epithelium)
Brunner's gland cell in duodenum (enzymes and alkaline mucus)
Seminal vesicle cell (secretes seminal fluid components, including fructose for swimming sperm)
Prostate gland cell (secretes seminal fluid components)
Bulbourethral gland cell (mucus secretion)
Bartholin's gland cell (vaginal lubricant secretion)
Gland of Littre cell (mucus secretion)
Uterus endometrium cell (carbohydrate secretion)
Isolated goblet cell of respiratory and digestive tracts (mucus secretion)
Stomach lining mucous cell (mucus secretion)
Gastric gland zymogenic cell (pepsinogen secretion)
Gastric gland oxyntic cell (hydrochloric acid secretion)
Pancreatic acinar cell (bicarbonate and digestive enzyme secretion)
Paneth cell of small intestine (lysozyme secretion)
Type II pneumocyte of lung (surfactant secretion)
Clara cell of lung
Hormone secreting cells Anterior pituitary cells
   Somatotropes
   Lactotropes
   Thyrotropes
   Gonadotropes
   Corticotropes
Intermediate pituitary cell, secreting melanocyte-stimulating hormone
Magnocellular neurosecretory cells
   secreting oxytocin
   secreting vasopressin
Gut and respiratory tract cells
   secreting serotonin
   secreting endorphin
   secreting somatostatin
   secreting gastrin
   secreting secretin
   secreting cholecystokinin
   secreting insulin
   secreting glucagon
   secreting bombesin
Thyroid gland cells
   thyroid epithelial cell
   parafollicular cell
Parathyroid gland cells
   Parathyroid chief cell
   Oxyphil cell
Adrenal gland cells
   chromaffin cells
   secreting steroid hormones (mineralcorticoids and gluco corticoids)
Leydig cell of testes secreting testosterone
Theca interna cell of ovarian follicle secreting estrogen
Corpus luteum cell of ruptured ovarian follicle secreting progesterone
   Granulosa lutein cells
   Theca lutein cells
Juxtaglomerular cell (renin secretion)
Macula densa cell of kidney
Peripolar cell of kidney
Mesangial cell of kidney
Derived primarily from ectoderm
Integumentary system
Keratinizing epithelial cells Epidermal keratinocyte (differentiating epidermal cell)
Epidermal basal cell (stem cell)
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell
Hair matrix cell (stem cell)
Wet stratified barrier epithelial cells Surface epithelial cell of stratified squamous epithelium of cornea, tongue, oral cavity, esophagus, anal canal, distalurethra and vagina
basal cell (stem cell) of epithelia of cornea, tongue, oral cavity, esophagus, anal canal, distal urethra and vagina
Urinary epithelium cell (lining urinary bladder and urinary ducts)
Nervous system There are nerve cells, also known as neurons, present in our human body. They are branched out. These cells make upnervous tissue. A neuron consists of a cell body with a nucleus and cytoplasm, from which long thin hair-like parts arise.
Sensory transducer cells Auditory inner hair cell of organ of Corti
Auditory outer hair cell of organ of Corti
Basal cell of olfactory epithelium (stem cell for olfactory neurons)
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor cells of retina in eye:
   Photoreceptor rod cells
   Photoreceptor blue-sensitive cone cell of eye
   Photoreceptor green-sensitive cone cell of eye
   Photoreceptor red-sensitive cone cell of eye
Proprioceptive primary sensory neurons (various types)
Touch-sensitive primary sensory neurons (various types)
Type I carotid body cell (blood pH sensor)
Type II carotid body cell (blood pH sensor)
Type I hair cell of vestibular system of ear (acceleration and gravity)
Type II hair cell of vestibular system of ear (acceleration and gravity)
Type I taste bud cell
Autonomic neuron cells Cholinergic neural cell
Adrenergic neural cell
Peptidergic neural cell
Sense organ and peripheral neuron supporting cells Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Taste bud supporting cell
Olfactory epithelium supporting cell
Schwann cell
Satellite glial cell (encapsulating peripheral nerve cell bodies)
Enteric glial cell TABLE 6-continued Central nervous system neurons and glial cells Astrocyte (various types)
Neuron cells (large variety of types, still poorly classified)
Oligodendrocyte
Spindle neuron
Lens cells Anterior lens epithelial cell
Crystallin-containing lens fiber cell
Derived primarily from mesoderm
Metabolism and storage cells Hepatocyte (liver cell)
Adipocytes:
   White fat cell
   Brown fat cell
Liver lipocyte
Barrier function cells (lung, gut, exocrine glands and urogenital tract)
Kidney Kidney parietal cell
Kidney glomerulus podocyte
Kidney proximal tubule brush border cell
Loop of Henle thin segment cell
Kidney distal tubule cell
Kidney collecting duct cell[disambiguation needed]
Type I pneumocyte (lining air space of lung cell)
Pancreatic duct cell (centroacinar cell)
Nonstriated duct cell (of sweat gland, salivary gland, mammary gland, etc.)
   principal cell
   Intercalated cell
Duct cell (of seminal vesicle, prostate gland, etc.)
Intestinal brush border cell (with microvilli)
Exocrine gland striated duct cell
Gall bladder epithelial cell
Ductulus efferens nonciliated cell
Epididymal principal cell
Epididymal basal cell
Extracellular matrix cells Ameloblast epithelial cell (tooth enamel secretion)
Plenum semilunatum epithelial cell of vestibular system of ear (proteoglycan secretion)
Organ of Corti interdental epithelial cell (secreting tectorial membrane covering hair cells)
Loose connective tissue fibroblasts
Corneal fibroblasts (corneal keratocytes)
Tendon fibroblasts
Bone marrow reticular tissue fibroblasts
Other nonepithelial fibroblasts
Pericyte
Nucleus pulposus cell of intervertebral disc
Cementoblast/cementocyte (tooth root bonelike ewan cell secretion)
Odontoblast/odontocyte (tooth dentin secretion)
Hyaline cartilage chondrocyte
Fibrocartilage chondrocyte
Elastic cartilage chondrocyte
Osteoblast/osteocyte
Osteoprogenitor cell (stem cell of osteoblasts)
Hyalocyte of vitreous body of eye
Stellate cell of perilymphatic space of ear
Hepatic stellate cell (Ito cell)
Pancreatic stelle cell
Contractile cells skeletal muscle Cell
   Red skeletal muscle cell (slow)
   White skeletal muscle cell (fast)
   Intermediate skeletal muscle cell
   nuclear bag cell of muscle spindle
   nuclear chain cell of muscle spindle
Satellite cell (stem cell)
Heart muscle cells
   Ordinary heart muscle cell
   Nodal heart muscle cell
   Purkinje fiber cell
Smooth muscle cell (various types)

Myoepithelial cell of iris
Myoepithelial cell of exocrine glands
Blood and immune system cells Erythrocyte (red blood cell)
Megakaryocyte (platelet pecursor)
Monocyte (white blood cell)
Connective tissue macrophage (various types)
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Hybridoma cell
Mast cell
Helper T cell
Suppressor T cell
Cytotoxic T cell
Natural Killer T cell
B cell
Natural killer cell
Reticulocyte
Stem cells and committed progenitors for the blood and immune system (various types)
Germ cells Oogonium/Oocyte
Spermatid
Spermatocyte
Spermatogonium cell (stem cell for spermatocyte)
Spermatozoon
Nurse cells Ovarian follicle cell
Sertoli cell (in testis)
Thymus epithelial cell
Interstitial cells Interstitial kidney cells

TABLE 7

B Cell maturation markers for use with the hydrogel particles described herein.

| B-cell type | Cell surface marker(s) |
|---|---|
| Pro-B | CD19, CD20, CD34, CD38, CD45R |
| Pre-B | CD19, CD20, CD38, CD45R |
| Immature B | CD19, CD20, CD40, CD45R, IgM |
| Tr-B | CD10, CD19, CD20, CD24, CD28 |
| Naïve-B | CD19, CD20, CD23, CD40, CD150 (SLAM), IgD, IgM |
| B-1 | CD19, CD20, CD27, IgM |
| Memory B | CD19, CD20, CD28, CD40, IgA, IgG |
| Plasma Cell | CD9, CD28, CD31, CD38, CD40, CD95 (FAS), CD184 (CXCR4) |

TABLE 8

Cell surface markers for use ACD with the hydrogel particles described ACE2 herein.

14-3-3 Î ± Î²
14-3-3 Îμ
14-3-3 Î¶
14-3-3 Î·
14-3-3 Îf
15-Lipoxygenase 1
160 kD Neurofilament Medium
200 kD Neurofilament Heavy
2H2
3G11 sialoganglioside antigen TABLE 8-continued Cell surface markers for use with the hydrogel particles described herein.

4E-BP1
4E-BP1 Phospho (Thr37/46)
5-Methylcytidine
5HT3A receptor
5T4
68 kDa Neurofilament Light
7.1
70 kD Neurofilament Light
A20
A2B5
AAK1
ABCA1
ABCA7
ABCB4
ABCB5
ABCC10
ABCC11
ABCG1
ABI2
ABIN3
ABIN3Î²
ABL2
Abraxas
ACAA1
ACADM
ACAT2
ACBD3
ACD
ACE2
Acetyl Coenzyme A Carboxylase
Acetyl Coenzyme A Carboxylase Î±
Acetyl Coenzyme A Synthetase
Acetylated Lysine
AChRÎ±
AChRÎ²
AChRÎ³
Aconitase2
ACOT12
ACSA2
ACSF2
ACSM5
Act1
Activation molecule 8 (B cells)
Activin A Receptor Type IB
Activin A Receptor Type IIB
ACTN3
ACY1
ACY3
ADA
ADAM12
ADE2
Adenosine A1 Receptor
Adenosine A2aR
Adenovirus
Adenovrus Fiber monomer and trimer
Adenovirus hexon protein
Adenylate Kinase 1
Adenylosuccinate Lyase
ADFP
ADH1B
ADH6
ADH7
ADI1
Adiponectin
Adiponectin Receptor 2
Adipose Triglyceride Lipase
ADP Ribosylation Factor
ADP-ribosyltransferase 2.2 gene
Adrenodoxin
AF10
AFAP1
AFP
AG2
AGAP1
AGPAT5
AGR2
AHSG
AICDA
AID
AIF
AIM-2
Aiolos
AIPL1
AIRE
AK3
AK3L1
AK5
Akt
Akt (pS473)
Akt (pT308)
Akt1
Akt2
Akt3
Albumin
Alcohol Dehydrogenase
Adehyde Reductase
ALDH1A1
ALDH1L1
ALDH2
ALDH3A1
ALDH3A2
ALDH5A1
ALDH6A1
ALDH7A1
ALDOB
Aldolase B
Alexa Fluor 405/Cascade Blue
Alexa Fluor 488
ALG2
Alix
Allergin1
alpha 1 Antitrypsin
alpha 1 Catenin
alpha 1 Sodium Potassium ATPase
alpha 2 Catenin
alpha 2 Macroglobulin
alpha Actin 1
alpha Actin 2
alpha Actinin
alpha Actinin 2
alpha Actinin 3
alpha Actinin 4
alpha Adaptin
alpha Adducin
alpha B Crystallin
alpha Fodrin
alpha Internexin
alpha Synuclein
ALS1
AMACR
Aminopeptidase P
AML1
Amphiphysin
AMPKÎ±
AMPKÎ± 1
AMPKÎ± 2
AMPKÎ²1
AMPKÎ³1
AmyloidÎ² 42
ANAPC2
AND1
Androgen Receptor
Angiotensin I
Angiotensin II Receptor 2
Angiotensin III
ANKRD53
Annexin IV
Annexin V
ANP
Anti-Kudoa thrysites
Anti-T. brucei procyclin (GPEET)
Anti-T. brucei procyclin (phosphorylated TABLE 8-continued Cell surface markers for use
with the hydrogel particles described
herein.

GPEET)
Antiglobulin (Coombs)
Antithrombin III
AP2 α
AP2 β ± β2
AP2 γ
AP2M1
AP2S1
APAF1
APBB3
APC
APC-1
APC-10
APC-11
APC-2
APC-3
APC-5
APC-7
APC-8
APE1
APG12
APG3
APG5
APG7
APMAP
Apo-2.7
Apo-2.7 (7A6)
ApoE
ApoE4
APOER2
Apolipoprotein AI
Apolipoprotein AII
Apolipoprotein AIV
Apolipoprotein B
Apolipoprotein CIII
Apolipoprotein D
Apolipoprotein E
Apolipoprotein F
Apolipoprotein H
Apolipoprotein J
Apolipoprotein L1
Apolipoprotein M
Apoptotic neutrophils
APP
Aquaporin1
Aquaporin5
ARF1
ARF5
ARFGAP1
ARFRP1
Argonaute-1
ARH
ARHGAP25
ARHGAP4
ARL11
ARL5B
ARPC5
Artemis
Aryl hydrocarbon Receptor
ASB-1
ASCC1
ASCC2
ASGPR
Asialo-GM1
ASK1
Asparagine synthetase
Ataxin 1
ATF1
ATF2
ATG4A
ATG9A
ATIC
Atlantic Salmon Ig
ATM
ATP citrate lyase
ATP1B3

TABLE 8-continued

Cell surface markers for use ACD
with the hydrogel particles described ACE2
herein.

ATP5A
ATP5H
ATP5J
ATP5O
ATP6V0D1
ATP6V1B1
ATPB
ATRIP
Aurora A
Aurora A Phospho (Thr288)
Aurora B
Aurora B Phospho (Thr232)
AVEN
Avian Influenza A Neuraminidase
Avidin
Axin 2
Axl
B and Activated T Cells
B Cell
B Cell Subset
B cells (pan reactive)
B lymphocytes antibody [UCH-B1]
b-Endorphin
B-Raf Phospho (Thr598/Ser601)
B18R
B7-H4
BACE1
BACE2
BACH1
baculovirus envelope gp64 protein
BAG1
BAG2
BAG3
BAG4
BAIAP2
BAK
BAMBI
BAP31
BAP37
basal cell Cytokeratin
Basophils
Bassoon
BATF
Bax
BCAR1
BCAR2
BCKD complex E2 subunit
Bcl-10
Bcl-2
Bcl-2 (pS70)
Bcl-2 like 12
Bcl-2 like 2
Bcl-22
Bcl-2A1
Bcl-2β
Bcl-3
Bcl-6
Bcl-xL
Bcl-XS/L
BCR
BCSC1
BDH2
BDKRB2
BDNF
Beclin1
Bestophin 3
beta 2 Adrenoreceptor
Beta 3 Adrenergic Receptor
beta 3 Sodium Potassium ATPase
beta Actin
beta Arrestin 1
beta Arrestin 2
beta Catenin
beta Catenin (npaa 27-37)
beta Catenin (npaa 35-50)
beta Catenin (pS45)

TABLE 8-continued

Cell surface markers for use with the hydrogel particles described herein.

beta Dystroglycan
beta galactosidase
beta galactosidase fusion proteins
beta Synuclein
beta2 Microglobulin
BHMT
Bid
Biglycan
Bilirubin Oxidase
Bim
BimL
BIN1
BIN3
Biotin
BiP
BLBP
Blimp-1
BLK
BLNK
BLNK (pY84)
Blood Group A Antigen
Blood Group AB Antigen
Blood Group B Antigen
Blood Group H ab Antigen
Blood Group H ab Antigen/n Antigen
Blood Group H inhibitor
Blood Group Lewis a
Blood Group M Antigen
Blood Group N Antigen
Blooms Syndrome Protein Blm
BM1
BMAL1
BMI1
Bmk
BMP15
BMP4
BMP7
BMPR1A
BMPR2
BMX
bMyc
BNIP2
BNIP3
BNIP3L
BOB1
BORA
Borealin
*Borrelia burgdorferi*
BPI
BRaf
BRCA1
BRCC36
BRD3
BrdU
BRF1
BRG1
BRN3A
Btk
Btk (pY551)/Itk (pY511)
BTLN-2
BTN1A1
Bu1
Bu1a
Bu1a/Bu1b
Bu1b
BubR1
Bulb
Butyrylcholinesterase
C peptide
C reactive protein
C/EBPβ2
C1 Inhibitor
C15orf40
C16orf72
C1orf50
C1Q

TABLE 8-continued

Cell surface markers for use with the hydrogel particles described ACE2 herein.

ACD
ACE2

C1QA
C1QB
C1QC
C1QG
C1r
C1s
C20orf30
C20orf43
C21orf56
C21orf59
C2orf43
C3
C3aR
C3b
C3c
C3d
C4
C4 binding protein
C4b
C4c
C4d
C4orf42
C5
C5aR1
C5L2
C6
C6orf64
C8A/B/G
C9
C9orf41
CA125
CA19.9
CAB39
CACNA1S
CACNA2
CACNG1
CAD
Cadherin 1
Cadherin 10
Cadherin 11
Cadherin 7
Cadherin 8
Cadherin 9
Cadherin E
Cadherin H
Cadherin K
Cadherin P
Cadherin R
CAK C Terminus
CAK N Terminus
CAK Phospho (Ser164/Thr170)
Calbindin
Calcineurin A
Calcitonin Receptor
Calcium Sensing Receptor
Caldesmon
Calgranulin A
Calgranulin B
Calmodulin
Calnexin-ER membrane marker
Calpain 1
Calpain 2
Calpain 9
Calpain S1 (small subunit)
Calpastatin
Calponin
Calreticulin
Calretinin
Calsequestrin 2
CaMKI
CaMKII
CaMKII Phospho (Thr286)
CaMKIIIʹ
CaMKIV
CaMKIIα
CAMLG TABLE 8-continued Cell surface markers for use with the hydrogel particles described herein.

cAMP Protein Kinase Catalytic subunit
cAMP Protein Kinase Catalytic subunit α
Cannabinoid Receptor I
Cannabinoid Receptor II
CAP-G2
CAP18
CAP2
CAP3
Carbonic Anhydrase I
Carbonic Anhydrase IX
Carboxylesterase 1
Carboxypeptidase A1
Carboxypeptidase A2
CARD11
CARD8
CARD9
Cardiac Troponin T
CARKL
CARM1
Casein Kinase 1 α
Casein Kinase 1 β2
Casein Kinase 2 β2
Caspase 1
Caspase 10
Caspase 11
Caspase 12
Caspase 2
Caspase 2L
Caspase 3
Caspase 4
Caspase 5
Caspase 6
Caspase 7
Caspase 8
Caspase 9
Catalase
Catechol-O-methyltransferase
Cathepsin D
Cathepsin K
Cathepsin L
Caveolin1
Caveolin1 (pY14)
Caveolin2
Cbl
CBP
CBWD1
CBX1
cCbl (pY700)
cCbl (pY774)
CCDC98
CCK4
CCL11
CCL17
CCL18
CCL19-Fc
CCL20
CCL21
CCL25
CCL3
CCL5
CCL6
CCNB1IP1
CCR10
CCR11
CCRD6
CCRL2
CD1
CD1.1
CD10
CD100
CD101
CD102
CD103
CD104
CD105
CD106

TABLE 8-continued

Cell surface markers for use with the hydrogel particles described herein.

CD107a
CD107b
CD108
CD109
CD11
CD110
CD111
CD112
CD113
CD114
CD115
CD116
CD117
CD118
CD119
CD11a
CD11a, strain polymorphism
CD11a/CD18
CD11b
CD11b/c
CD11c
CD11d
CD120a
CD120b
CD121a
CD121b
CD122
CD123
CD124
CD125
CD126
CD127
CD129
CD13
CD130
CD131
CD132
CD133
CD133/2
CD134
CD135
CD136
CD137
CD137L
CD138
CD139
CD14
CD140a
CD140b
CD140b (pY1009)
CD140b (pY1021)
CD140b (pY771)
CD140b (pY857)
CD141
CD142
CD143
CD144
CD146
CD147
CD148
CD15
CD150
CD151
CD152
CD153
CD154
CD155
CD156c
CD157
CD158a
CD158a/h
CD158b
CD158b1/b2/j
CD158d
CD158e
CD158e/k TABLE 8-continued Cell surface markers for use with the hydrogel particles described herein.

- CD158e1
- CD158e1/e2
- CD158f
- CD158g
- CD158h
- CD158i
- CD158j
- CD159a
- CD159c
- CD15s
- CD16
- CD16/32
- CD16/56
- CD160
- CD161
- CD161a
- CD162
- CD162R
- CD163
- CD164
- CD165
- CD166
- CD167a
- CD168
- CD169
- CD16b
- CD17
- CD170
- CD171
- CD172
- CD172a
- CD172a/b
- CD172b
- CD172g
- CD173
- CD177
- CD178
- CD178.1
- CD179a
- CD179b
- CD18
- CD180
- CD181
- CD182
- CD183
- CD184
- CD185
- CD186
- CD19
- CD191
- CD192
- CD193
- CD194
- CD195
- CD195 (cytoplasmic)
- CD195 Phospho (Ser337)
- CD195 Phospho (Ser349)
- CD196
- CD197
- CD198
- CD199
- CD1a
- CD1b
- CD1b/c
- CD1c
- CD1d
- CD1d Î± GalCer Complex
- CD2
- CD20
- CD200
- CD200R
- CD200R3
- CD201
- CD202b
- CD203a
- CD203c
- ACD
- ACE2
- CD204
- CD205
- CD206
- CD207
- CD208
- CD209
- CD209b
- CD21
- CD21/CD35
- CD210
- CD212
- CD213a1
- CD213a2
- CD217
- CD218a
- CD22
- CD22 (pY822)
- CD22.2
- CD220
- CD220Î±
- CD221
- CD221 (pY1131)
- CD222
- CD223
- CD224
- CD226
- CD227
- CD229
- CD229.1
- CD23
- CD230
- CD231
- CD233
- CD234
- CD235a
- CD235ab
- CD236
- CD239
- CD24
- CD240CE
- CD240DCE
- CD243
- CD244
- CD244.1
- CD244.2
- CD245
- CD246
- CD247
- CD247 (pY142)
- CD249
- CD25
- CD252
- CD253
- CD254
- CD255
- CD256
- CD257
- CD258
- CD26
- CD261
- CD262
- CD263
- CD264
- CD265
- CD266
- CD267
- CD268
- CD269
- CD27
- CD270
- CD271
- CD272
- CD273
- CD274
- CD275
- CD276

TABLE 8-continued

Cell surface markers for use with the hydrogel particles described herein.

| |
|---|
| CD277 |
| CD278 |
| CD279 |
| CD28 |
| CD280 |
| CD281 |
| CD282 |
| CD283 |
| CD284 |
| CD284/MD2 Complex |
| CD286 |
| CD289 |
| CD29 |
| CD290 |
| CD294 |
| CD298 |
| CD299 |
| CD2a |
| CD3 |
| CD3/CD44 |
| CD30 |
| CD300 |
| CD300a |
| CD300e |
| CD300f |
| CD301 |
| CD303 |
| CD303a |
| CD304 |
| CD305 |
| CD307d |
| CD309 |
| CD31 |
| CD310 |
| CD312 |
| CD314 |
| CD314 (activating) |
| CD314 (blocking) |
| CD317 |
| CD318 |
| CD319 |
| CD32 |
| CD321 |
| CD323 |
| CD324 |
| CD325 |
| CD326 |
| CD328 |
| CD329 |
| CD32B |
| CD33 |
| CD334 |
| CD335 |
| CD336 |
| CD337 |
| CD338 |
| CD339 |
| CD34 |
| CD340 |
| CD344 |
| CD349 |
| CD35 |
| CD351 |
| CD354 |
| CD357 |
| CD358 |
| CD36 |
| CD360 |
| CD361 |
| CD36L1 |
| CD37 |
| CD38 |
| CD39 |
| CD39L4 |
| CD3D |
| CD3G |

TABLE 8-continued

Cell surface markers for use with the hydrogel particles described herein.

ACD
ACE2

| |
|---|
| CD3Î³ |
| CD3Î' |
| CD3Îµ |
| CD3Îµ (CD3 Molecular Complex) |
| CD4 |
| CD4 (domain 1) |
| CD4 (domain 2) |
| CD4 v4 |
| CD40 |
| CD40bp |
| CD41 |
| CD41/CD61 |
| CD41a |
| CD41b |
| CD42a |
| CD42b |
| CD42d |
| CD43 |
| CD44 |
| CD44 (v3) |
| CD44 (v4) |
| CD44 (v5) |
| CD44 (v6) |
| CD44 (v7) |
| CD44.2 |
| CD44std |
| CD44v6 |
| CD44var (v10) |
| CD44var (v3) |
| CD44var (v3-v10) |
| CD44var (v4) |
| CD44var (v5) |
| CD44var (v6) |
| CD44var (v7) |
| CD44var (v7-v8) |
| CD45 |
| CD45.1 |
| CD45.2 |
| CD45R |
| CD45RA |
| CD45RB |
| CD45RC |
| CD45RO |
| CD46 |
| CD47 |
| CD48 |
| CD49a |
| CD49a/CD29 |
| CD49b |
| CD49b/CD29 |
| CD49b/CD61 |
| CD49c |
| CD49d |
| CD49d/CD29 |
| CD49e |
| CD49e/CD29 |
| CD49f |
| CD49f/CD29 |
| CD4Î± |
| CD5 |
| CD5.1 |
| CD5.2 |
| CD5.6 |
| CD50 |
| CD51 |
| CD51/61 |
| CD52 |
| CD53 |
| CD54 |
| CD55 |
| CD56 |
| CD57 |
| CD58 |
| CD59 |
| CD59a |
| CD6 |

TABLE 8-continued

Cell surface markers for use with the hydrogel particles described herein.

- CD60b
- CD61
- CD62E
- CD62L
- CD62P
- CD63
- CD64
- CD64 a, b alloantigens
- CD64.1
- CD65
- CD65s (CD65 sialylated)
- CD66
- CD66a
- CD66a/b/c/e
- CD66a/c/d
- CD66a/c/d/e
- CD66a/c/e
- CD66a/e
- CD66b
- CD66c
- CD66c/e
- CD66e
- CD66f
- CD68
- CD69
- CD7
- CD70
- CD70b
- CD71
- CD72
- CD72 a, b, c alloantigens
- CD72 b, c alloantigens
- CD72.1
- CD73
- CD74
- CD75
- CD77
- CD78
- CD79a
- CD79b
- CD8
- CD80
- CD81
- CD82
- CD83
- CD84
- CD85
- CD85a
- CD85d
- CD85g
- CD85h
- CD85j
- CD85k
- CD86
- CD87
- CD88
- CD89
- CD8Î±
- CD8Î±.1
- CD8Î±.2
- CD8Î²
- CD9
- CD90.1
- CD90.2
- CD90.9
- CD91
- CD91Î±
- CD91Î²
- CD93
- CD94
- CD95
- CD96
- CD97
- CD98
- CD98hc
- CD99

TABLE 8-continued

Cell surface markers for use with the hydrogel particles described herein. ACD ACE2

- CD99R
- Cdc-123
- Cdc-2 (p34)
- Cdc-25A Phosph (Ser17)
- Cdc-25C
- Cdc-37
- Cdc-45L
- Cdc-6
- CDc-7
- Cdk1
- Cdk2
- Cdk4
- Cdk5
- Cdk6
- Cdk7
- Cdk9
- CdkA1
- CdkN2A
- CdkN3
- CDT1
- CDX2
- CEACAM19
- CEACAM20
- CEACAM7
- CEBPÎ±
- CEBPÎ²
- CEND1
- CENPA
- CENPE
- CENPF
- CENPH
- Centrin 2
- CFAH
- cFos
- CFTR
- CGB5
- cGK1
- CH2
- CHCHD5
- CHD3
- CHD4
- Chemerin
- CHIPS, C-terminus
- CHIPS, N-terminus
- Chk1
- Chk2
- Chondroitin Sulfate
- CHOP
- Chromogranin C
- ChT1
- chTOG
- cIAP1
- CIAP2
- CIAS1
- CIDEA
- CIP4
- CISD1
- CITED1
- CITED2
- cJun
- cJun Phospho (Tyr91/Tyr93)
- CKIIÎ±
- CKMT2
- CLASP1
- Clathrin
- Claudin-1
- Claudin-10
- Claudin-15
- Claudin-16
- Claudin-18 (C-term)
- Claudin-18 (Mid)
- Claudin-4
- Claudin-5
- Claudin-8
- CLAW-H
- CLEC12A TABLE 8-continued Cell surface markers for use with the hydrogel particles described herein.

CLEC1B
CLEC4A
CLEC4M
CLEC9A
CLIP
CLOCK
*Clostridium botulinum* Toxin B
CLPP
cMaf
cMet
CMKLR1
CMRF44
CMRF56
cMyb
cMyc
CNDP2
CNTFRÎ±
COASY
Coatomer Î'
Cofilin
Colec12
Collagen I
Collagen I/III
Collagen II
Collagen III
Collagen IV
Collagen V
Collagen VI
Collagen VII
COMMD1
Complement Factor B
Complex I Immunocapture
Conjugated Choline Glutaric acid
Connexin 26
Connexin 30
Connexin 30.2
Connexin 30.3
Connexin 32
Connexin 36
Connexin 37
Connexin 37 (C-term)
Connexin 37 (Mid)
Connexin 39
Connexin 39 (Mid)
Connexin 40 (C-term)
Connexin 40 (Mid)
Connexin 43
Connexin 45
Connexin 45 (C-term)
Connexin 46
Connexin 47
Connexin 57 (C-term)
Connexin 57 (Mid)
Contactin 2
COPS3
Coronavirus
Coronin 1A
Coronin 1B
Cortactin
Cortical Thymocytes
COX I
COX I/III
COX II
COX IV
COX VA
COX VIA1
Coxsackie Adenovirus Receptor
CPF
CPI17Î±
Cpn10
CPO
CPS1
CPT2
CRABP1
CRABP2
CRALBP
ACD
ACE2
Creatine Kinase BB
Creatine Kinase MM
CREB
CREB Phospho (Ser133)
cRel
Cripto1
CRISP3
Crk p38
CrkL
CrkL (pY207)
CROT
CRRY
CRTAM
CRTC3
CRY2
Cryptochrome I
Cryptosporidium
Cryptosporidium Parvum
CRYZL1
CSK
CSK Binding Protein
CSPS
cSrc
CST2
CTDSP1
CTNNA3
CTNNBL1
Cullin 1
Cullin 2
Cullin 3
Cullin 4A
Cullin 4A/B
Cullin 4B
Cutaneous Lymphocyte Antigen
CUTL1
CX3CL1
CX3CR1
CXCL1
CXCL10
CXCL12Î±
CXCL12Î²
CXCL13
CXCL9
CXCR7
CXorf26
Cyanine
CYB5R2
CYB5R3
Cyclin A
Cyclin A2
Cyclin B1
Cyclin B2
Cyclin D1
Cyclin D2
Cyclin D3
Cyclin E
Cyclin E2
Cyclin H
Cyclins D1/D2/D3
Cyclophilin 40
CYLD
CysLT1
Cystatin C
Cystatin S
Cytochrome B245 heavy chain
Cytochrome B245 light chain
Cytochrome c
Cytochrome P450 17A1
Cytochrome P450 19A1
Cytochrome P450 1A2
Cytochrome P450 2A6
Cytochrome P450 2B6
Cytochrome P450 2C9
Cytochrome P450 2J2
Cytochrome P450 3A4
Cytochrome P450 3A5

TABLE 8-continued

Cell surface markers for use with the hydrogel particles described herein.

Cytochrome P450 Reductase
Cytokeratin
Cytokeratin (acidic)
Cytokeratin (basic)
Cytokeratin (Pan-reactive)
Cytokeratin 1
Cytokeratin 10
Cytokeratin 10/13
Cytokeratin 13
Cytokeratin 14
Cytokeratin 14/15/16/19
Cytokeratin 15
Cytokeratin 16
Cytokeratin 17
Cytokeratin 18
Cytokeratin 19
Cytokeratin 2
Cytokeratin 20
Cytokeratin 4
Cytokeratin 4/5/6/8/10/13/18
Cytokeratin 40
Cytokeratin 5
Cytokeratin 5/6/18
Cytokeratin 5/8
Cytokeratin 6
Cytokeratin 6a
Cytokeratin 7
Cytokeratin 7/17
Cytokeratin 8
Cytokeratin 8/18/19
D4-GDI
DAB2
DACH1
DAND5
DAP1
DAP12
DAPK1
DAPK2
DARPP32
Daxx
DAZL
DBC1
DCAMKL1
DCC
DCIR2
DCLRE1B
DCP1a
DcR3
DCTN2
DcTRAIL-R1
DcTRAIL-R2
DCXR
DDB1
DDDDK tag
DDX3
DDX4
DDX50
DECR1
Dectin1
Dectin2
DEF8
Defensin Î ± 1
DELETE
delta 1 Catenin
Delta like protein 1
Delta like protein 4
Delta Opioid Receptor
DeltaC
DeltaD
Dendritic Cell Marker
Deoxycytidine kinase
Desmin
Desmoglein 2
Desmoglein1
Desmoplakin
Destrin TABLE 8-continued Cell surface markers for use with the hydrogel particles described herein.

ACD
ACE2

Dextran
DGKA
Dicer
DISC1 (C-term)
DISC1 (Mid)
Dishevelled 3
Disialoganglioside GD2
Disialoganglioside GD3
Dkk1
Dkk3
DLC8
DLK1
Dlx5
DM-GRASP
DMT1
DNA-PKcs
DNA-PKcs Phospho (Thr2609)
DNAI1
DNAJA2
DNAJB2
DNAJC3
DNAPK
DNM1L
Dnmt1
Dnmt3b
DNP
DOK2
DOK7
Dopamine Receptor D1
Dopamine Receptor D3
Dopamine Receptor D5
Dopamine Î² Hydroxylase
Doublecortin
DP1
DPH2
DPP10
DPP3
DPP9
Dppa4
DPYD
DR3
DRAK1
DRAK2
Drebrin
DTYMK
DUSP23
DUSP27
DUSP3
DUSP5
DUSP6
DUX4
DYKDDDDK Epitope Tag
Dynamin
Dynamin1
Dynamitin
Dynein light chain 2
Dysbindin
Dysferlin
Dystrobrevin Î±
Dystrobrevin Î²
Dystroglycan Phospho (Tyr893)
*E. Coli* O/E
E2A-Pbx1
E2F1
E47
E4BP4
Ea52-68 peptide bound to I-A
Ea52-68 peptide bound to the I-A
EAAT1
Early B Lineage
EBF1
EBI3
EBP50
ECGF1
ECH1
ECRG4

TABLE 8-continued

Cell surface markers for use with the hydrogel particles described herein.

EDA
EDA-A2R
EDG1
EDG2
EDG3
EDG6
EEA1
EEF1G
EEF2
EEF2K
EEN
EFEMP1
EFEMP2
Eg5
Eg5 Phospho (Thr927)
EGF
EGF Receptor
EGF Receptor (pY1173)
EGF Receptor (pY845)
EGF Receptor (pY992)
EGR1
EGR2
EHD1
eIF1
eIF2C2
EIF2S1
eIF2Î3
eIF3
eIF3D
eIF3D (p66)
eIF3F
eIF3G
eIF3H (p40)
eIF3I (p36)
eIF3J
eIF3K
eIF4B
eiF4E
eIF4E (pS209)
eIF4E2
eIF5A
eIF6
Elastase
Elk1
Elk1 (pS383)
ELK3
Elongin B
Elongin C
EMAP II
Embigin
EMG1
Emi1
EMR3
EMSY
Ena/Vasp-like
EndoG
EndoGlyx-1
Endomucin
Endothelial Cells
Endothelial Lipase
Endothelial Venule Marker
Endothelium
Engrailed1
ENO1
Enolase1
eNOS
eNOS (pS1177)
Entpd2
Eomes
Eos
Epac1
Eph Receptor A1
Eph Receptor A2
Eph Receptor A4
Eph Receptor B4
Eph Receptor B6

TABLE 8-continued

Cell surface markers for use with the hydrogel particles described herein.

ACD
ACE2
Ephrin A2
Ephrin A3
EPHX2
EPM2AIP1
EPOR
EPS15R
Epsin 1
Epsin 2
ER-HR3
ER-MP54
ER-TR7
ER81
ERAB
ERCC1
ERG
ERK1
ERK1/2 (pT185/pY187)
ERK1/2 (pT202/pY204)
ERK1/ERK2
ERK2
ERK5
ERMAP
ERp29
ERp72
Erythroid Cells
Erzin/Radixin/Moesin
ERÎ ± Phospho (Ser167)
ESAM
Estrogen Inducible Protein pS2
Estrogen Receptor
Estrogen Receptor Î±
Estrogen Receptor Î²
Estrogen Related Receptor alpha
ETAR
Ethenoadenosine
ETS1
EVI2A
EVI2B
EWSR1
EXD1
EXOSC3
EXOSC7
EYA2
EZH1/2
Ezrin
Ezrin (pY353)
F-actin
F10A1
F4/80
FAA4
FABP4
Factor I
Factor IX
Factor VIII.vWF (delete)
Factor XIIIa
FADD
FAHD2A
FAK
FAK (pS910)
FAM119A
FAM175A
FAM84B
FAM91A1
FANCC
FANCD2
Fanconi anemia D2 Phospho (Ser222)
FAP
Fascin
FBP1
FBXO21
FBXO31
FBXO42
FBXO43
Fc Receptor Binding Inhibitor
Fc receptor IgA + IgM
FcR TABLE 8-continued Cell surface markers for use with the hydrogel particles described herein.

FcRL6
FcRLA
FcÎµRI
FDC
FDFT1
FDPS
FE65
FeLV p27
FEN1
FER
Ferritin Heavy Chain
Ferritin Light Chain
Ferritin, mitochondrial
FES
Fetal Hemoglobin
FGF acidic
FGF basic
FGF21
FGFR1
FGFR2
FGR
FH
FHL1
Fibrillarin
Fibrillin
Fibrinogen
Fibrinogen Î± chain
Fibrinogen Î³ chain
Fibrinopeptide A
Fibrinopeptide B
Fibroblast activation protein Î±
Fibroblast Surface Protein
Fibroblasts/Epithelial cells
Fibronectin
Fibronectin Receptor
Fibulin5
Ficolin B
Filaggrin
Filamin A
FITC
FITC/Oregon Green
FIV
FIV gp120
FIV gp95
FIV p24
FIV p24 gag
FKBP12
FKBP4
FKBP6
FKBPL
FLiC
Flightless1
FLIP
Flt3L
Fluorescent Protein
FLV gp70
FLYWCH2
FMC7
fMLP Receptor
FMRP
FNTA
FNTB
Follicular Dendritic Cells
Fos
FOXA1
FOXA2
FOXC2
FOXD3
FOXI1
FOXJ1
FOXM1
FOXO1
FOXO3A
FOXP1
FOXP3
FPRL1
ACD
ACE2
FR4
Fra2
Fragilis
FRAT1
Frataxin
Frequenin
Frizzled-1
FSHÎ±
FSHÎ²
FUK
FUS
FXYD3
FYB
Fyn
Fyn (pY528)/c-Src (pY530)
Fyn-Related Kinase
FZR1
G-CSF
G3BP
G6PD
GAB1
GAB2
GABA B Receptor 2
GABARAP
GAD65
GAD67
GADD34
Galacto-cerebroside
Galactocerebroside
Galectin 1
Galectin 10
Galectin 3
Galectin 4
Galectin 7
Galectin 8
Galectin 9
gamma Synuclein
Ganglioside GD2
Ganglioside GD3
Ganglioside GM1
Gankyrin
GAP
GAP43
GAPDH
GARP
GAS2
GAS7
GAT2
GATA1
GATA2
GATA3
GATA4
GATM
GBA3
GBE1
GBP1
GBP2
GBP5
GC1qR
GCDFP15
GCDH
GCK1
GCLM
GCN2
GCN5
GCTM2
GDAP1L1
GDF15
Gelsolin
Gemin1
Gephyrin
GFAP
GFP
GILZ
GIMAP4
GIPR TABLE 8-continued Cell surface markers for use with the hydrogel particles described herein.

- GIT2
- GITRL
- GLAST
- Gli1
- Glial Fibrilary Acidic Protein
- Glicentin
- GLIPR1L1
- Glucagon
- Glucocorticoid Receptor
- Glucocorticoid Receptor alpha
- Glucose 1 Dehydrogenase
- Glucose 6 Phosphate Isomerase
- GLUH1
- GLUT1
- GLUT2
- GLUT4
- GLUT5
- Glutamate receptor 2
- Glutamate receptor 2/3
- Glutamate receptor 3
- Glutamate receptor 4
- Glutaminase
- Glutamine Synthetase
- Glutaredoxin 2
- Glutathione NEM
- Glutathione NEW
- Glutathione Peroxidase 1
- Glutathione Peroxidase 4
- Glutathione Reductase
- Glutathione S Transferase Î, 2
- Glutathione S Transferase Î°1
- Glutathione S Transferase Î¼
- Glutathione Synthetase
- Glycogen synthase 1
- Glycoprotein IX
- Glycoprotein VI
- GM-CSF
- GM130
- GM3.2
- GNB2
- GNB2L1
- GNLY
- GNMT
- GnRHR
- Golgi Protein (58K)
- Golgi Zone
- GOLM1
- GOLPH2
- GOSR1
- gp340
- gp49R
- GPA33
- GPCR5C
- GPR-120
- GPR-143
- GPR-151
- GPR-18
- GPR-30
- GPR-40
- GPR-48
- GPR-49
- GPR-50
- GPR-56
- GPR-73A
- GPR-73B
- GPR-77
- GPR-83
- GPR-86
- GPR-C5C
- GPR-C5D
- Granulin
- Granulysin
- Granzyme A
- Granzyme B
- Granzyme K
- GRAP2

TABLE 8-continued

Cell surface markers for use with the hydrogel particles described herein.

- ACD
- ACE2
- GRASP1
- GRASP65
- GRB2
- GRB7
- GRHPR
- GRIM19
- GRK1
- GRK2
- GRK3
- GRK5
- GRK6
- Growth hormone receptor
- GRP170
- GRP94
- GSC
- GSK3Î±
- GSK3Î±/Î²
- GSK3Î²
- GSPT2
- GST
- GST Epitope Tag
- GSTA4
- GTF2D1
- GTPase HRAS
- GTPBP4
- Guanylate kinase
- H-2
- H-2.m31
- H-2Db
- H-2Dd
- H-2Kd
- H2-M
- H2-M3
- H2A.X
- H2A.X Phospho (Ser139)
- H2A1J
- H60
- HA tag
- HADHA
- HADHA/HADHB
- HADHB
- HADHSC
- HAND1
- HAO1
- Haptoglobin
- HARS
- HARS2
- HBF
- hCGÎ±
- hCGÎ²
- hCGÎ²4
- HCN4
- HDAC1
- HDAC10
- HDAC2
- HDAC3
- HDAC4
- HDAC6
- HDAC9
- HDHD1A
- HDHD2
- HDJ2
- HDLBP
- HE4
- HEC1
- HEF1
- Helios
- Hematopoiesis related Macrophage
- Hematopoietic Lineage Cocktail
- Hematopoietic Progenitor Cell
- Hemoglobin
- Hemoglobin F
- Hemoglobin subunit Î±
- Hepatitis B Virus
- Hepatitis B Virus Core Antigen
- Hepatitis B Virus E Antigen TABLE 8-continued Cell surface markers for use with the hydrogel particles described herein.

- Hepatitis B Virus Surface Antigen (Ad/Ay)
- Hepatitis C Virus
- Hepatitis C Virus Core Antigen
- Hepatitis C Virus NS4
- Hepsin
- HER3
- HER4
- Hes1
- Hexokinase
- Hexokinase1
- Hexokinase2
- HFE1
- HGF
- HGFA Inhibitor 1
- HHEX
- HHV8 GPCR
- HIBCH
- HID1
- HIF-1α
- HIF-2α
- HIF1AN
- HINT1
- HIP2
- HIPK2
- Hippocalcin
- Histamine H3 Receptor
- Histocytes
- Histone H1
- Histone H1.0
- Histone H2A
- Histone H2B
- Histone H2B type 1B
- Histone H3
- Histone H3 Phospho (Ser10)
- Histone H3 Phospho (Ser28)
- Histone H3.3
- Histone H4
- HIV1 Core Antigen
- HIV1 p17
- HIV1 p24
- HIV1 p55/p17
- HIV1 tat
- HL60
- HLA Class I
- HLA-2Kb/2Db
- HLA-2kb/2Dd
- HLA-A
- HLA-A/B/C
- HLA-A1/A11/A26
- HLA-A1/A36
- HLA-A10/A11
- HLA-A10/A28/B75
- HLA-A10/B62/B71
- HLA-A11
- HLA-A2
- HLA-A2/A25/A32
- HLA-A2/A28
- HLA-A2/A3/A29
- HLA-A2/A69
- HLA-A2/B17
- HLA-A2/B5
- HLA-A2/B57
- HLA-A23/A24
- HLA-A24/A11/A2403
- HLA-A25
- HLA-A25/A26
- HLA-A25/A26/A34
- HLA-A25/A32
- HLA-A26/A34/B71/B62
- HLA-A29
- HLA-A3
- HLA-A30/A31
- HLA-A33/B8
- HLA-A34/B71/A26
- HLA-A9
- HLA-A9/A25/A32
- HLA-A9/A32/B13
- HLA-B
- HLA-B12
- HLA-B13/B62/B15
- HLA-B14
- HLA-B17
- HLA-B17/B35/B44
- HLA-B21/B70/B55
- HLA-B27/B44/B47
- HLA-B35/B57/B75/B77
- HLA-B44/B75/B17
- HLA-B48/B60
- HLA-B5/B49/B56
- HLA-B7
- HLA-B8
- HLA-B8/B14
- HLA-BC
- HLA-Bw4/A9/A32
- HLA-Bw6
- HLA-Bw6/B77
- HLA-class I free chain
- HLA-D
- HLA-DM
- HLA-DO
- HLA-DP
- HLA-DQ
- HLA-DQ/DR
- HLA-DQ1/DQ3
- HLA-DQ1/DR7
- HLA-DQ3
- HLA-DQ6
- HLA-DQ7
- HLA-DQA1
- HLA-DQB1
- HLA-DQw1
- HLA-DR
- HLA-DR/DP
- HLA-DR/DP/DQ
- HLA-DR1
- HLA-DR11
- HLA-DR3/DR6
- HLA-DR4
- HLA-DR7
- HLA-DR7/DRβ2
- HLA-DR8/DR12
- HLA-DR9
- HLA-DRA
- HLA-DRβ2
- HLA-DRβ23
- HLA-E
- HLA-G
- HLCS
- HLF
- HLXB9
- HMG14
- HMG17
- HMG4
- HMGB1
- HMGB2
- HMOX1
- HMOX2
- HNF4α
- hnRNPA1
- hnRNPC1/C2
- hnRNPD
- hnRNPK
- hnRNPL
- hnRNPU
- hnRNPUL1
- Homing Receptor
- HOXB4
- HOXB5
- HP1α
- HPa1
- HPa2
- HPD TABLE 8-continued Cell surface markers for use with the hydrogel particles described herein.

- HPd1
- HPd2
- HPi1
- HPi2
- HPi3
- HPi4
- HPR1
- HPRT1
- HPV16 E1/E4
- HPx1
- HPx2
- Hrk
- Hsc70
- HSD17B1
- HSD3B1
- HSF1
- HSF2
- HSF4
- HSL
- Hsp105
- Hsp14
- Hsp22
- HSP25
- Hsp27
- Hsp40
- Hsp47
- Hsp60
- Hsp70
- Hsp70-2
- Hsp90
- Hsp90α
- Hsp90β
- HspA4
- HspA6
- HSPA9
- HspB2
- HspB7
- HSV tag
- HTLV I gp46
- HTLV I p19
- HtrA2/Omi
- Human Papillomavirus 16 (E7)
- Huntingtin
- HUS1
- Hydrogen Potassium ATPase β
- I-Ak (Aα ± k)
- I-Ak (Aβk)
- Ia (B cells)
- IBA1
- IBP2
- ICAD
- IDO
- IFABP
- IFN-α
- IFN-γ ± 1
- IFN-γ ± 2β
- IFN-β
- IFN-γ
- IFN-γRβ
- IFN-ι ©
- IFNA1
- IFNAR1
- IFT88
- Ig
- Ig (polyspecific)
- Ig light chain κ
- Ig light chain λ
- Ig light chain λ1, λ2, λ3
- IgA
- IgA (Fab2)
- IgA(H)
- IgA, κ
- IgA, λ
- IgA1
- IgA2
- IgD

- ACD
- ACE2
- IgD (δ heavy chain)
- IgDa
- IgDb
- IgE
- IgE, ε
- IgEa
- IgEb
- IgG
- IgG (Fab H/L)
- IgG (Fab)
- IgG (Fab2 Fc)
- IgG (Fab2 H/L)
- IgG (Fab2)
- IgG (Fc)
- IgG (H/L)
- IgG (γ chain specific)
- IgG Fd
- IgG light chain
- IgG, ε
- IgG/IgM
- IgG/IgM/IgA
- IgG/IgM/IgA (Fab2 H/L)
- IgG/IgM/IgA (Fab2)
- IgG/IgM/IgA (H/L)
- IgG/IgY
- IgG1
- IgG1 (heavy chain)
- IgG1, κ
- IgG1, λ
- IgG1/2a
- IgG1/3
- IgG1a
- IgG1b
- IgG2
- IgG2, κ
- IgG2, λ
- IgG2/3
- IgG2a
- IgG2a, κ
- IgG2a, λ
- IgG2a/b
- IgG2b
- IgG2b, κ
- IgG2c
- IgG2c, κ
- IgG3
- IgG3, κ
- IgG3, λ
- IgG4
- IgGDa
- IgK
- IGKC
- IgL
- IGLC2
- IgM
- IgM (Fab2)
- IgM (Fc)
- IgM (H/L)
- IgM, κ
- IgM, λ
- IgMa
- IgMb
- IgY
- Ig's
- Ihh
- Ikaros
- IkBα
- IkBβ
- IkBγ
- IKKα
- IKKβ
- IKKγ p(S376)
- IKKμ
- IL-10
- IL-11Rα
- IL-12

TABLE 8-continued

Cell surface markers for use with the hydrogel particles described herein.

- IL-12 (p35)
- IL-12 (p70)
- IL-12 Rβ1
- IL-12 Rβ2
- IL-12/IL-23 (p40)
- IL-13
- IL-15
- IL-15/IL-15R
- IL-15Rα
- IL-16
- IL-17D
- IL-17A
- IL-17A/F
- IL-17B
- IL-17C
- IL-17E
- Il -17F
- IL-18
- IL-18BP
- IL-19
- IL-1RA
- IL-1RN
- IL-1α
- IL-1β
- IL-2
- IL-20R2
- IL-20Rα
- IL-20Rβ
- IL-21
- IL-22
- IL-22Rα2
- IL-23 (p19)
- IL-23R
- IL-24
- IL-25
- IL-27
- IL-27 (p28)
- IL-27Rα
- IL-28
- IL-28Rα
- IL-29
- IL-3
- IL-31
- IL-32αβγδ
- IL-32αδ
- IL-33
- IL-34
- IL-4
- IL-4Rα
- IL-5
- IL-6
- IL-7
- IL-7Rα
- IL-8
- IL-9
- ILF3
- ILK
- ILK1
- ImmunofluorescenceN-γ
- IMP3
- Importin9
- Influenza A Virus M2 Protein
- Influenza B Virus Nucleoprotein
- ING1
- ING2
- ING3
- ING4
- Inhibin α
- iNOS
- INPP4A
- INPP4B
- Insulin
- Insulin Degrading Enzyme (IDE)
- Insulin Receptor R
- Integrin α 4/β7
- Integrin α 9/β1

TABLE 8-continued

Cell surface markers for use with the hydrogel particles described ACE2 herein.

- Integrin α V/β5
- Integrin α V/β6
- Integrin β1 Phospho (Tyr783)
- Integrin β1 Phospho (Tyr795)
- Integrin β5
- Integrin β6
- Intonrin β7
- Intercalated DNA
- Intra Acrosomal Protein
- Intra-Acrosomal Proteins
- Invariant NK T
- IP10
- IQGA1
- IRAK1
- IRAK3
- IRAK4
- IRE1
- IRF1
- IRF3
- IRF4
- IRF5
- IRF6
- IRF7
- IRF7 (pS477/pS479

TABLE 8-continued

Cell surface markers for use with the hydrogel particles described herein.

- KMT4
- KMT5A
- KOR-SA3544
- KS1/4
- Ksp37
- KSR1
- Ku70
- Ku70/80
- Ku80
- Kudoa Thyrsites
- Kunitz Protease Inhibitor
- Kv4.2
- L/S-MAG
- Labeling Check Reagent
- Lactate Dehydrogenase
- Lactate Dehydrogenase B
- Lambda
- Lamin A
- Lamin A/C
- Lamin B Receptor
- Lamin B1
- Lamin B2
- Lamin C
- Laminin
- Laminin 5
- Laminin Receptor
- Laminin β1
- LAMP2a
- LAMP2b
- LAT
- LAT (pY171)
- LAT (pY226)
- LBP
- LC3
- LC3B
- LCAT
- Lck
- Lck (pY505)
- LDH1
- LDH1/B/C
- LDL (MDA oxidized)
- LDLR
- LEF1
- Leishmania LPG (repeat epitope)
- Leishmania Major Surface Protease (GP-63)
- LEKTI
- Leukemia Inhibitory Factor
- Leukotriene A4 hydrolase
- Leukotriene B4 Receptor
- LHX3
- LI-Cadherin
- LIF
- DNA Ligase I
- DNA Ligase III
- LIM kinase 2
- LIME1
- LIMK1
- LIMS1
- Lin28
- Lineage Cocktail
- Lipin 1
- LIS1
- Liver Carboxylesterase 1
- LKB1
- LMO2
- LOX
- LOX1
- LRP5/6
- LRP6
- LRPAP1
- LSD1
- LSP1
- LSS
- LTβ
- Luciferase
- LXRα

TABLE 8-continued

Cell surface markers for use with the hydrogel particles described herein.

- ACD
- ACE2
- Ly-108
- Ly-49A
- Ly-49A/D
- Ly-49AB6
- Ly-49C/F/I/H
- Ly-49C/I
- Ly-49D
- Ly-49E/F
- Ly-49F
- Ly-49G
- Ly-49G2
- Ly-49G2B6
- Ly-49H
- Ly-49I
- Ly-51
- Ly-6A.2/Ly-6E.1
- Ly-6A/E
- Ly-6b
- Ly-6B.2
- Ly-6C
- Ly-6D
- Ly-6G
- Ly-6G/C
- Ly-6K
- Ly-77
- Lymphotoxin β
- Lymphotoxin β Receptor
- Lyn
- LYRIC
- Lysophospholipase 1
- Lysosomal acid lipase
- Lysozome
- Lysozyme
- Lyve1
- M-CSF
- M13 Bacteriophage Coat Protein g8p
- M13 Bacteriophage Protein
- MAA
- Mac-2BP
- macroH2A.1
- Macrophage
- Macrophage Activator
- Macrophage galactose lectin
- Macrophage/Granulocyte
- Macrophages/Monocytes
- MAD2
- MadCAM1
- MADD
- MADH7
- MAFB
- MAG
- MAGE-A
- MAGE1
- MAIR2
- MAIR4
- MALT1
- Mammaglobin A
- MAP1LC3A
- MAP2
- MAP2B
- MAP2K1IP1
- MAP3K8
- MAP4 Phospho (Ser768)
- MAP4K1
- MAP4K4
- MAPK12
- MAPK6
- MAPKAP Kinase 2
- MAPKAP Kinase 2 Phospho (Thr334)
- MARCKS
- MARCO
- Marginal Zone B Cells
- MARK2
- MARK3
- MART1
- Mast Cell TABLE 8-continued Cell surface markers for use with the hydrogel particles described herein.

ACD
ACE2
Mast Cell Protease 11
mature macrophage marker
MBD1
MBD2
MBL
MCL1
MCM2
MCM3
MCM4
MCM5
MCM6
MCM7
MCP-1
MCP-4
MCP-8
MCSF
MD1
MD2
MDC
MECT1
MEF2A
MEIS1
MEK1
MEK1 (p298)
MEK1 (pS218)/MEK2 (pS222)
MEK1/2 (pS222)
MEK2
MEK3
MEK4
MEK5
MEK6
MEK7
MEKK1
MEKK2
MEKK3
MEKK4
Melanoma
MELK
MEMO1
Mena
Menin
MEOX2
Merlin
MERTK
Mesothelin
Metallothionein
MetRS
mGluR5
MGMT
MHC Class I
MHC Class I (H-2Db)
MHC Class I (H-2Dd)
MHC Class I (H-2Dk)
MHC Class I (H-2Dq/Lq)
MHC Class I (H-2Kb)
MHC Class I (H-2Kb/Db)
MHC Class I (H-2Kb/Dd)
MHC Class I (H-2Kd a3 domain)
MHC Class I (H-2Kd)
MHC Class I (H-2Kd/Dd)
MHC Class I (H-2Kd/Dd/q/u/v)
MHC Class I (H-2Kk)
MHC Class I (H-2Kq)
MHC Class I (H-2Ks)
MHC Class I (H-2Ld)
MHC Class I (H-2Ld/Db)
MHC Class Ib (H2-M3)
MHC Class II
MHC Class II (DQ)
MHC Class II (DR)
MHC Class II (I-A)
MHC Class II (I-A/E)
MHC Class II (I-Ab)
MHC Class II (I-Ab/Ad)
MHC Class II (I-Ab/As)
MHC Class II (I-Ad)
MHC Class II (I-Ak)
MHC Class II (I-Ak/Ad/Ab/Aq/Ar)
MHC Class II (I-Ak/As)
MHC Class II (I-Ap)
MHC Class II (I-Aq)
MHC Class II (I-E)
MHC Class II (I-Eî°)
MHC Class II (RT1B)
MHC Class II (RT1Bu)
MHC Class II (RT1D)
MHC Class II Î²
MHC Qa1b
MICA
MICA/MICB
MICB
Microfold (M) Cells
Microtubule Associated Protein 2ab
Microtubule Associated Protein RP/EB 2
Midkine
Mineralocorticoid Receptor
MIP-1Î²
MIPEP
Mitochondria
Mitofilin
Mitofusin 1
Mitofusin 2
Mitotic Cells
MKK6
MLH1
MLK3
MLL1
MLLT11
MMP1
MMP10
MMP11
MMP12
MMP13
MMP14
MMP15
MMP17
MMP19
MMP2
MMP20
MMP21
MMP26
MMP3
MMP8
MMP9
Mnk1
mNOS
MnSOD
Moesin
Monoamine Oxidase B
Monocyte/Granulocyte
Mononuclear Phagocyte
Mouse Embryonic Fibroblast (mEF) Feeder Cells
Mouse Lineage
MPP1
MRCL3
MRE11
MRGPR-X2
MRI1
MRP14
MRP2
MRP3
MRP4
MRP5
MRP6
MRP8
MRP8/14
MSC (W8B2)
MSC (W3D5)
MSC (W5C5)
MSC (W7C6)
MSC/NPC TABLE 8-continued Cell surface markers for use with the hydrogel particles described herein.

ACD
ACE2
MSH2
MSH6
MSI2H
MSK1
MST1
MST1/MST2
MST3
MST4
MST4/MST3/STK25
mTOR
Muc-16
Muc-2
Muc-3
Muc-4
Muc-7
MULT-1
Munc13-4
Munc18
MUPP1
Mus81
Musashi1
Muscarinic Acetylcholine Receptor 2
muscle Actin
Muscleblind-like 1
MVP
MYBBP1A
MYBPC3
Myc tag
MyD88
Myelin Basic Protein
Myelin oligodendrocyte glycoprotein
Myelin PLP
Myeloid Antigen
Myeloid Cell Nuclear Differentiation Antigen
Myeloid Lineage
Myocilin
Myogenin
Myosin heavy chain
Myosin IIA
Myosin light chain 2
Myosin light chain 3
Myosin light chain kinase
Myosin Phosphatase
Myosin Phosphatase 1/2
MYST2
NADH2
Naf1
NAK
Nanog
NAPE-PLD
NAT1
Native Lipoteichoic Acid
Natriuretic Peptide Receptor A
Natural Killer Cell
Natural Killer Cell Activation Structures
NBS1
NC1.1
NCF4
Nck
NCOA1
NCOA2
NCX1
NDUFAF1
NDUFB4
NDUFS3
NEDD8
NEK2
NEK6
NEK7
NEK9
NEK9 Phospho (Thr210)
Nestin
NETO2
Neurabin1
Neuregulin1

TABLE 8-continued

Cell surface markers for use with the hydrogel particles described herein.

ACD
ACE2
Neuregulin3
Neuroblastoma
NeuroD1
NeuroD2
Neurofibromin
Neurofilament Heavy Protein
Neurofilament Medium Protein
Neurogenin 2
Neurokinin 1 Receptor
Neuron Specific Enolase
Neuronal Growth Factor Receptor
Neurotensin Receptor 1
NFÎ°B p50/p105
NFÎ°B p65 (pS536)
NFATc1
NFÎ°B p50
NFÎ°B p50/p105
NFÎ°B p52/p100
NFÎ°B p65
NFÎ°B p65 (pS529)
NG2
NGF
Nhedc2
NHERF1
Nicastrin
Ninein
Nitrotyrosine
NKG2A/C/E
NKG2AB6
NKp80
NKX3.1
NM23A
NMDA Receptor 2A
NMDA Receptor 2B
NMDE2
NMDZ1
NMNA2
nMyc
nNOS
NNTM
Nociceptin
Nod2
Nodal
Noggin
NONO
Nonspecific Cytotoxic Cells
Notch1
Notch2
Notch3
Notch4
NOX2
NOX4
NOXA2
NPC
NPM-ALK
NPM/B23 Phospho (Thr199)
NPM/B23 Phospho (Thr234/Thr237)
NPY5R
NQOI
NR2E1
NRC2C
Nrf2
NRG3
NSPA/B
NTAL
NTF97
Nucleolin
Nucleolin Phospho (Thr76/Thr84)
Nucleophosmin
NUDC
NUMA1
Nur77
O acetyl GD3
2-Oct
Oct3/4
Oct3/4A TABLE 8-continued Cell surface markers for use with the hydrogel particles described herein.

- 4-Oct
- ODAG
- OGDH
- OLIG1
- OLIG2
- Oligodendrocyte Marker
- Oligodendrocyte Marker O1
- Oligodendrocyte Marker O4
- Oncostatin M Receptor
- Orai1
- OSCAR
- OSR1
- Osteonectin
- Osteopontin
- Osteoprotegerin
- Otx2
- OVA (SIINFEKL) H-2Kb
- Oval Cell Marker
- Ovalbumin
- Ovarian Carcinoma-associated Antigen
- OX-62
- p110Î'
- p120 Catenin
- p120 Catenin (pS268)
- p120 Catenin (pS288)
- p120 Catenin (pS879)
- p120 Catenin (pT310)
- p120 Catenin (pT916)
- p120 Catenin (pY228)
- p13
- p130
- p130 Cas
- p130 Cas (pY249)
- p14ARF
- p150, 95
- p19ARF
- P21
- p22phox
- p23
- p27Kip1
- P2RX4
- P2RY8
- P2X3
- P2X7
- P2Y6
- p34Cdc-2
- p38
- p38 MAPK (pT180/pY182)
- p400
- p53
- p53 Acetylated (Lys305)
- p53 Acetylated (Lys382)
- p53 Phospho (Ser15)
- p53 Phospho (Ser37)
- p53 Phospho (Ser392)
- p53BP1 (Ser1778)
- p57Kip2
- p60 CAF1
- p62
- p63
- p63 (TA)
- p70 S6 Kinase Î2
- p90 Rsk
- p90 Rsk Phospho (Thr368/Ser372)
- p95 NBS1
- p97
- PA28Î3
- PABP1
- PABP2
- PABPN1
- PAC1
- PAD2
- PAG1
- PAK1
- PAK2
- PAK3

TABLE 8-continued

Cell surface markers for use ACD with the hydrogel particles described ACE2 herein.

- pan Actin
- pan Macrophage
- Panendothelial Cell Antigen
- PAR1
- Parainfluenza Virus type 1
- Parainfluenza Virus type 2
- Parainfluenza Virus type 3
- PARC
- PARD3
- PARK7/DJ1
- PARP, Cleaved Form
- PARP16
- PARP4
- PARVA
- Pax2
- Pax5
- Pax6
- Pax7
- Pax8
- Pax9
- Paxillin
- Paxillin Phospho (Tyr118)
- Paxillin Phospho (Tyr31)
- PBEF
- PBK
- PBP
- PBR
- PBX3
- PCB
- PCNA
- PCYT1A
- PD-1H
- PD-ECGF
- PDC-TREM
- PDCD4
- PDCD6
- PDE3B
- PDECGF
- PDGF-AA
- PDI
- PDK1
- PDK2
- PDPK1
- PDPK1 (pS241)
- PDX1
- PDZK1
- PE
- PECR
- PEI-Transferrinfection
- Pellino 1
- Pentraxin 3
- PEPD
- Perforin
- Peroxiredoxin 1
- Peroxiredoxin 2
- Peroxiredoxin 6
- PEX5
- PF4
- PGC1Î±
- PGIS
- PGP9.5
- PGRP-Ia
- PGRP-S
- PHD1
- PHD2
- Phosphatidylserine
- Phospho SHIP
- Phospholipase A2 activator protein (PLAP)
- Phospholipase C Î²3
- Phospholipase C Î³1
- Phospholipase D1
- Phosphoserine/threonine/tyrosine
- Phosphotyrosine
- PI 3 Kinase catalytic subunit Î±
- PI 3 Kinase catalytic subunit Î³

TABLE 8-continued

Cell surface markers for use with the hydrogel particles described herein.

PI 3 Kinase p110 β
PI 3 Kinase p110 γ
PI 3 Kinase p150
PI 3 Kinase p85 α
PI 4 kinase β
PIAS1
PIAS3
PICK1
PIM1
PIM2
Pin1
PINK1
PIP5K2α
PIP5KIIγ
PIR-A/B
Pirh2
PIST
PiTX3
PIWIL2
PKA RIIα (pS99)
PKA RIIβ (pS114)
PKA2β
PKAR2
PKAγ
PKC
PKCq
PKCα
PKCα (pT497)
PKCα (pT638)
PKCβ
PKCβ2
PKCγ
PKCδ
PKCμ
PKC¶
PKCι
PKCι ...
PKN
PKN2
PKR
PKX1
PLA2G1B
Placental alkaline phosphatase
Placental Protein 14
Plakophilin 3
Plastin L
Platelet
PLAU
PLCγ1
PLCγ1 (pY783)
PLCγ2
PLCγ2 (pY759)
Plectin
Pleiotrophin
PlexinA1
PlexinB2
PLGF
PLK1
PLK1 Phospho (Thr210)
PLK4
PLSCR1
PLVAP
PLZF
PMCA(1-4)
PMCA4
PMEL17/SILV
PMN
PMP70
PMS2
PNAd
PNPH
Podocalyxin
Podoplanin
POKEMON
Polyhistidine Tag
PON1
ACD
ACE2
PON3
PP2Aα
PP2Aα β
PPM1A
PPP1A
PPP5C
PPP6C
PR3
PRA1
PRC1
Pre-BCR
Pre-T Cell Receptor α Chain
Prealbumin
Presenilin1
Presenilin2
Prion protein PrP
PRKRA
PRLR
PRMT1
PRMT5
pro Relaxin 1/2
pro Relaxin 2
Profilin1
Progesterone Receptor
Prohibitin
Prokineticin 1
Prokineticin 2
Prolactin
ProMBP1
Prostaglandin D2 Receptor
Prostaglandin dehydrogenase 1
Prostaglandin E Receptor EP3
Prostate Cell Surface Antigen
Prostate Specific Antigen
Prostatic Acid Phosphatase
Proteasome 20S C2
Proteasome 20S α 2
Proteasome 20S α 3
Proteasome 20S α 5
Proteasome 20S α 6
Proteasome 20S α 7
Proteasome 20Sα 1/2/3/5/6/7
Protein A
Protein G
Protein Kinase D2
Protein Phosphatase 1β
Protein phosphotase inhibitor 1
Protein S
Proteinase Activated Receptor 4
Prothrombin
PSA-NCAM
PSD95
*Pseudomonas Aeruginosa*
PSMA
PSMD14
Psoriasin
PTAFR
PTBP1
PTEN
PTGER2
PTGER4
PTHLH
PTK7
PTP1B
PTP4A2
PTPS
PTPμ
PTRH2
PU.1
PU60
PUMA
PUMAγ
Pumilio1
Pumilio2
PXR
PYCARD TABLE 8-continued Cell surface markers for use
with the hydrogel particles described
herein.

Pygopus2
Pyk2
Pyk2 (pY402)
Pyruvate Dehydrogenase E1α
Pyruvate Dehydrogenase E2
Pyruvate Dehydrogenase E2/E3bp
q2
Qa1(b)
Qa2
RAB11A
RAB25
RAB27A
RAB4
RAB5a
RAB9
Rac1
Rac1/Cdc42
RAD17
RAD17 Phospho (Ser645)
RAD23A
RAD51
RAD54
RAD9A
Radixin
RAE-1β
RAE-1γ
RAF1
RAGE
RAIDD
Rainbow Trout Ig
RalBP1
RanBP9
RanGAP1
RAP1A/RAP1B
RAP1GAP
Raptor
RARα
RAS
RASGAP
RASGRF1
RASSF1A
Rb
Rb (a.a. 332-344)
Rb (pS780)
Rb (pS807/pS811)
RbAp46
RbAp48
RBC
RBC (Polyclonal Rabbit)
RBM35A
RBP4
RBX1
RCC1
RcRL6
Red Blood Cell
Relaxin 1
Relaxin 1/2
Relaxin 2
RelB
RELMβ
RELT
Renin
RENT1
Reptin
Repulsive Guidance Molecule C
Resistin
REST
Ret
Reticular Fibroblasts and Reticular Fibres
Reticulon1A
Reticulum Cells
Retinoblastoma 1
RFLAT1
RFP
RGS6
RGS7

TABLE 8-continued

Cell surface markers for use ACD
with the hydrogel particles described ACE2
herein.

RGS9
RHEB
Rho
RhoA
RHOC
RhoGAP
RhoGDI
RIAM
RICTOR
RIG1
RIP1
RIP2
Rituximab
RLA DQ
RLA DR
RNA polymerase II
RNA polymerase II CTD repeat YSPTSPS
RNASE-L
RNASE1
RNF144B
RNF168
RNF36
RNPEP
ROCK1
ROR1
ROR2
RORα
RORγ
ROS
RPA32/RPA2
RPA70
RPS6
RSF1
RSK1 p90
RSK2
RSK3
RSK4
RT1A
RT1Aa
RT1Aa, b
RT1Aa, b, l
RT1Ac
RT1Au
RT1B
RT6.1
RT6.2
Ryanodine Receptor
RYK
RyR
S-Tag
S100A1
S100A10
S100A13
S100A4
S100A6
S100A9
S100α
S100β
S100γ
S6 (pS235/pS236)
S6 (pS240)
S6 (pS244)
S6K
SAA4
Sall4
*Salmonella Paratyphi* A
*Salmonella Typhimurium*
Salmonid Ig (H and L chain)
Salmonid Ig (H chain)
SAM68
SAMD2
SAP
SARA
SATB1
SATB2

TABLE 8-continued

Cell surface markers for use with the hydrogel particles described herein.

ACD
ACE2
SC5A5
SC6A4
SCAI
SCD1
Scramblase1
SCY1-like 3
SDF1
SDF1α
SDHA
SDHB
Secretory component
Securin
SELP
Sema4A
Sema7A
SENP1
SEPP1
SERCA2
SerpinB1
SerpinB2
SerpinB6
Sestrin1
SFRP2
SGK1
SHC1
*Shigella Boydii*
SHIP1
SHP1
SHP2
SHP2 (pY542)
SIAH2
SIGIRR
Siglec-10
Siglec-8
Siglec-9
Siglec-F
Siglec-H
SIK2
SIRT1
SIRT2
SIRT3
SIRT5
SIT1
SIX2
SKP1A
SLA-DR
Slan
SLC1A3
SLC1A7
SLC22A1
SLC22A5
SLC26A6
SLC26A7
SLC30A4
SLC39A11
SLC4A3
SLC6A19
SLC6A6
SLC7A10
SLC7A14
SLC7A3
SLC7A8
SLC8A2
SLC9A6
SLP76
SLP76 (pY128)
SM22α
SMAC
SMAC3
SMAD1
SMAD1 (pS463/465)
SMAD1/5
SMAD1/9
SMAD2
SMAD2/3 (pS465/467) DELETE
SMAD3

TABLE 8-continued

Cell surface markers for use with the hydrogel particles described herein.

ACD
ACE2
SMAD4
SMAD5
SMAD6
SMC1
SMC1L1
SMN
Smoothelin
SMURF2
SNAP25
SNX1
SOAT1
SOCS1
SOCS2
SOCS3
SOCS6
SOD2
Sodium Potassium ATPase
Sonic Hedgehog
Sortilin
SOSC3
SOX1
SOX10
SOX17
SOX18
SOX2
SOX2 (COOH terminus)
SOX2 (NH2 terminus)
SOX9
SP-D
Sp1
Sp3
Spectrin Î ± 1
SPHK1
Spt16
Src (pY418)
SREBP1
ssDNA
SSEA3
SSEA4
SSEA5
SSH3BP1
SSR2
SSR5
SSRP1
SSX2IP
Stat1
Stat1 (N-Terminus)
Stat1 (pS727)
Stat1 (pY701)
Stat1α
Stat2
Stat3
Stat3 (pS727)
Stat3 (pY705)
Stat4
Stat4 (pY693)
Stat5
Stat5 (pY694)
Stat5a
Stat5b
Stat6
Stat6 (pY641)
Stathmin/Op18 Phospho (Ser16)
Stathmin1
Stefin B
Stem Cell Factor
STIM1
STK3
STK33
STK39
STOM
STRO1
STUB1
SULT1A1
SULT1A3/SULT1A4
SULT1C2

TABLE 8-continued

Cell surface markers for use with the hydrogel particles described herein.

SULT2A1
SUMO1
SUMO2
SUMO3
SUN1
Suppressor of Fused
SUPT16H
Survivin
Survivin Phospho (Thr34)
SV40 Large T and Small t Antigens
SWC1a
SWC6
SYBL1
Syk
Syk (pY348)
Synapsin I
Synapsin II
Synaptojanin2
Synaptophysin
Syndecan4
SynGAP
Synip
Syntaxin
Syntaxin6
Syntrophin
SYWC
T cells (pan reactive)
T Lymphocytes
T- and B-Cell Activation Antigen
T7 tag
TAB1
TACE
TACI
TAF172
TAF250
TAG72
Talin1
Talin2
Tamm Horsfall (Uromucoid)
TANK1
TAP1
TAP2
TARDBP
TARP
Tartrate-resistant acid phosphatase
TAS1R1
Tau
TBA1B
Tbet
TBK1 (pS172)
TBX1
TC10
TCF3
TCF7L1
TCF7L2
TCL1
TCP1α
TCP1β
TCR
TCR DO11.10
TCR HY
TCR Vα 11
TCR Vα 11.1/11.2b, d
TCR Vα 2
TCR Vα 24
TCR Vα 24-Jα 18
TCR Vα 3.2
TCR Vα 3.2b, c
TCR Vα 7.2
TCR Vα 8
TCR Vα 8.3
TCR Vβ1
TCR Vβ10a
TCR Vβ10b
TCR Vβ11
TCR Vβ12

TABLE 8-continued

Cell surface markers for use with the hydrogel particles described herein. ACD ACE2

TCR Vβ12b
TCR Vβ13
TCR Vβ13.1
TCR Vβ13.2
TCR Vβ13.6
TCR Vβ14
TCR Vβ16
TCR Vβ17
TCR Vβ17α
TCR Vβ18
TCR Vβ2
TCR Vβ20
TCR Vβ21.3
TCR Vβ22
TCR Vβ23
TCR Vβ3
TCR Vβ4
TCR Vβ5
TCR Vβ5.1
TCR Vβ5.1/5.2
TCR Vβ5.2
TCR Vβ5.3
TCR Vβ6
TCR Vβ7
TCR Vβ7.1
TCR Vβ7.2
TCR Vβ8
TCR Vβ8.1/8.2
TCR Vβ8.2
TCR Vβ8.2/8.3
TCR Vβ8.2/8.4
TCR Vβ8.3
TCR Vβ8.5
TCR Vβ9
TCR Vγ1.1
TCR Vγ1.1/γ1.2
TCR Vγ2
TCR Vγ3
TCR Vγ9
TCR Vδ1
TCR Vδ2
TCR Vδ4
TCR Vδ6.3/2
TCR α
TCR α/β
TCR β
TCR γδ
TCR γ
TCTP
TdT
Tec
TEF1
TEM8
Tenascin C
TER119
TERF2
Terminal-Deoxynucleotidyl Transferase
TERT
Tetranectin
TFF3
TFIIB
TGF-β
TGF-β1
TGF-β3
TGF-βR1
TGF-βR2
TGN38
TGN46
THAP11
THEMIS
Thioredoxin
Thioredoxin Reductase 1
ThPOK
Thrombin Receptor
Thrombocyte
Thrombospondin

TABLE 8-continued

Cell surface markers for use with the hydrogel particles described herein.

Thymidine Kinase 1
Thyroglobulin
TIA-1
TIAM2
Tie1
Tie2 (pY1102)
Tie2 (pY992)
TIF1β Phospho (Ser473)
TIGIT
Tim1
Tim2
Tim3
Tim3 Fc Fusion Protein
Tim4
Tim50
Timeless
TIMP1
TIMP2
TIP49A
TIRAP
TIS11b
TL1A
TLK1
TLR11
TLR12
CD285
TLR7
TLR8
TMEFF2
TMPS2
TMSA
TMTSP
TNAP
TNAP3
TNF-α
TNF-β
TNFR Related Protein
TNPO3
Tollip
TOMM20
TOMM22
TOP1
TOP2A
TOP2B
TORC2
Torsin A
TOX
TPH1
TPPP
TPTE
TR11B
TRA-1-60
TRA-1-60R
TRA-1-81
TRA-2-49
TRA-2-54
TRADD
TRAF2
TRAF4
TRAF5
TRAF6
TRAM2
Transferrin
Transglutaminase
Transglutaminase2
Transketolase
TRAP1
TRAPPC2
TRAPα
Trem-like 2
Trem-like 4
TRIB2
TRIB3
TRIM
TRIM25
TRIM29

TABLE 8-continued

Cell surface markers for use with the hydrogel particles described herein.

ACD
ACE2
TRK
TrkA
TrkC
Trop2
Tropomyosin 1
TROY
TRPC6
TRPM2
TRPM8
TRX1
Trypanosoma brucei Major Lysosomal Protein
Trypanosoma brucei procyclin (EP)
Trypanosoma congolense procyclin
Trypanosoma cruzi LPG
TSC2 Phospho (Ser664)
TSC2 Phospho (Thr1462)
TSG101
TSHR
TSLP
TSLP Receptor
TSPO
TTF1
Tubb3
Tuberin
Tubulin α
Tubulin α 1B
Tubulin α 4a
Tubulin α 3E
Tubulin α 8
Tubulin β
Tubulin β class III
Tubulin β4
Tubulin β3
tumor antigens of epithelial origin
Twist2
TXNIP
TYK2
TYMS
Tyro3
Tyrosinase
Tyrosine Hydroxylase
UACA
UBA52
UBC9
UBE2
UBE2L3
UBE2L6
UBE2M
UBE2N
UBF
UBF1
Ubiquitin
UBK63
UCH37
UCK
UCP2
UCP3
UFM1
ULBP1
ULBP2
ULBP4
ULK3
UNC5A
UNC5B
UNG
uPA
UQCRC1
UQCRC2
Urm1
URP2
USF1
USP11
USP13
USP22
USP28

TABLE 8-continued

Cell surface markers for use with the hydrogel particles described herein.

- USP7
- UTF1
- V5 tag
- VAMP5/8
- VAP1
- VASA
- VASP
- VAV1
- VAV2
- VAV3
- VDAC1
- VEGF
- VEGF-120
- VEGF-A
- VEGF-R1
- VELIS-3
- VGLU1
- Villin
- Vimentin
- Vinculin
- Viperin
- VIPR1
- Vitamin D Binding protein
- Vitamin D Receptor
- Vitronectin
- VMAT2
- vMyb/cMyb
- von Willebrands factor
- VRK1
- VSV-G tag
- WAPL
- WASP
- WC14
- WC15
- wCD44
- WIP (pS488)
- WNT1
- WNT16
- WNT2
- WNT5B
- WNT6
- WSTF
- WWOX
- Xanthine Oxidase
- XBP1
- XBP1 (COOH terminus)
- XBPs
- XCL1
- XIAP
- XPC
- XPNPEP3
- XRCC2
- XTP4
- YAP1
- YB1
- YES1
- YY1
- ZAP-70
- ZAP-70 (pY292)
- ZAP-70 (pY319)
- ZAP-70 (pY319)/Syk(pY352)
- ZBP-1
- ZIPK
- ZO-1 (Mid)
- ZONAB (Mid)
- Zyxin
- IL-33R
- Globo H
- CCL8
- Siglec-G
- CD307e
- CLEC6
- Snail 1
- SMAD1 (pS463/pS465)/SMAD8 (pS465/pS467)
- SMAD2 (pS465/pS467)/SMAD3 (pS423/pS425)
- GSK-3β (pY216)
- NKX6.1
- FAK (pY397)
- Btk (pY223)/Itk (pY180)
- ERK3
- CD276β
- MCP-3
- FcµR
- CD238
- beta2 Microglobulin [b, c]
- Nucleostemin
- GPR-49 (Central LRR)
- GPR-49 (N-Terminal)
- Phospholipase C γ4
- coilin
- HNF1β
- Trinitrophenal
- Annexin VII
- CD301a
- CD301b
- mTOR (pS2448)
- PI16
- MSC (W5C5)
- LAMP5
- GPR-19
- FPRL2
- CXCL5
- PAR2
- PDGF-Rα
- ULBP6
- ULBP2/5/6
- IL-17B Receptor
- ULBP3
- Arginase 1
- Alkaline Phosphatase
- ULBP3
- TrkB
- Osteocalcin
- IL-22Rα 1
- APJ
- IFN-α/β Receptor Subunit 2
- FGFR3
- SR-A1
- Rae-1 (pan)
- CXCL12
- TREM2
- Brachyury
- CLEC5A
- Integrin α 7
- Mer
- XCR1
- AML2
- von Willebrands factor A2
- MMP7
- GLP-1R
- FR1
- IL-1RAcP
- Claudin-6
- Leptin Receptor
- Caherin 6
- IL-1R type II
- Nectin4
- Delta like protein 3
- ChemR23
- GPR-39
- CD158b2
- IL-10Rα
- LRIG1
- Neuropilin2
- IL-10Rβ
- IL-18Rβ
- GPR-44
- Eph Receptor B2
- Glypican3
- IFN-γR2

TABLE 8-continued

Cell surface markers for use with the hydrogel particles described herein.

IL-17C Receptor
BMPR1B
IL-31RA
OCIL
Frizzled-7
IL-26
GPR-15
PlexinD1
CD158
FPR1
HBEGF
Vitamin D3
PlexinB1
Somatostatin Receptor 2
OV-6
CXCL16
Siglec-E
EDG5
Ninjurin-1
Integrin α 9
MHC Class II (I-Ed/j/k/p/r/u/v)
ThB
MAP-2 (2a & 2b)
IgM μ-chain
MHC Class I (H-2b/p)
MHC Class I (H-2s/p/q/d/u/r)
MHC Class I (H-2s/f)
CDw60
Bad Phospho (Ser112)
Caspase 3 Cleaved (Asp 175)
Chk1 Phospho (Ser345)
Chk2 Phospho (Thr68)
Cyclin D1 Phospho (Thr286)
cFos Phospho (Ser32)
FosB
GSK-3β (pSer9)
Histone H3 Acetylated (Lys9)
HS1 Phospho (Tyr397)
Hsp27 Phospho (Ser82)
ID3
CD221β
Phospho-IRAK4 (Thr345/Ser346)
Phospho-cJun (Ser73)
S6 (pS240/pS244)
Syk (pY525/pY526)
C23
Hemoglobin β
CD221α
p27
cJun Phospho (Ser63)
PPARγ
ENPP1
PILRα
PILRβ
Twist1
Cadherin M
CD302
CD66d
CLEC14A
CD242
Syndecan2
IL-32α
CDO
Cryptic
Endothelin B Receptor
FR3
IGSF3
CD85f
Matriptase
MCEMP1
mGluR4
Stabilin1
Stabilin2
Cadherin 13
GPR-109A
TSPAN8
Reg1A
Cadherin 12
ECE1
FABP5
IGSF4C
Trem-like 1
Activin A Receptor Type IIA
ALK7
BCAM
BLAME
CEACAM4
Claudin-3
CLP24
CRHR1
DC-STAMP
Eph Receptor B3
FATP4
FcRL1
FcRL2
FcRL3
FSH-R
Gi24
Histamine H1 Receptor
Neu5Gc
Lin28A
IL-33Rα
ATM (pSer1981)
Integrin α 8
Integrin β7
Integrin β8
CD158k
KOR
CD85i
LRIG3
LRP4
MMP16
MS4A4A
NAALADase-like 2
Neuropeptide Y receptor type 1
Oncostatin M Receptor β
MS4A3
PEAR1
PEDF Receptor
PlexinA4
Protocadherin1
ROBO2
ROBO4
EDG8
Scavenger receptor A5
Semaphorin 4A
Semaphorin 4B
Semaphorin 6A
Siglec-16
Somatostatin Receptor 3
STING
GPBAR1
TM4SF4
TMEM87A
TSPAN2
VEGF-R1, 2, 3
ADAM15
Calreticulin2
Complement Factor H-related 4
CXCL6
CD158a/h/b2/f/g
Ea52-68 peptide bound to I-Ab
HLA-Bw4
ATF1 Phospho (Ser63)
Epiregulin
FATP1
Fibromodulin
Furin
Galanin
IL-11
CD306
MFG-E8

TABLE 8-continued

Cell surface markers for use with the hydrogel particles described herein.

MINA
Oct4A
OLIG1, 2, 3
Oncostatin M
Semaphorin 3E
Slug
SOX3
STYK1
LTBP1
TIMP3
VAP-B
WNT9a
5HT2C
AATK
ACLP
ADAMTS15
alpha 1B Adrenoreceptor
APLP1
Fluorescein/Oregon Green
RXR-β
L3MBTL3
CCL1
PRDM4
ACTH
PDZ binding kinase
HuC/HuD neuronal protein
TDRD3
EP300
Carbonic Anhydrase VI
Cholecystokinin A Receptor
CCL23
CD1e
Chondrolectin
Chordin-Like 2
Claudin-10b
Claudin-11
Claudin-12
Claudin-17
CLEC2A
Coagulation Factor VII
CXCL1/2/3
DDR2
DPCR1
Dipeptidyl peptidase 6
Epithelial membrane protein 3
Endoglycan
Calgranulin C
FATP2
FATP5
FcRLB
GLP-2R
GLUT3
Glypican6
GPR-22
GPR-37
GPR-37L1
INSRR
LINGO1
LINGO2
mGluR2
mGluR7
MMP25
Neuromedin B Receptor
NRAGE
Osteoactivin
Porimin
Prokineticin Receptor 1
Prominin2
Semaphorin 3A
SLAP-130
Somatostatin Receptor 5
SCARF1
STAMP2
TAFA3
TAFA4
TM4SF18
ACD
ACE2
Tuberous Sclerosis 1
TCF8
CMG2
IL-17D Receptor
Macrophage Stimulating Protein Receptor
Siglec-11
Syndecan3
TGF-β R3
CD85e
SOX7
Activin A Receptor Type IA
Carbohydrate Sulfotransferase 15
CD300b
CELSR3
Coagulation Factor II
DC-SCRIPT
DSCAM-L1
FLRT1
Frizzled-6
Glypican1
IGSF4B
IL-1R9
BAZ2B
BRD4
Kell
Kremen2
LAX1
CD85c
MIF
Neprilysin2
OBCAM
PlexinC1
RGM-B
Wilms' Tumor protein 1
Xg
DCBLD2
ASAM
Desmocollin1
Frizzled-3
MMP24
TOR
WNT3a
Glypican5
Jagged1/Jagged2
Pax3
CELSR2
Cyclin D1/D2
PlexinA2
TAFA5
FR4
CD315
NKG2I
RAMP2
TNFRH3
Biotin
GPVI
MS4A4B
PIR-B
Semaphorin 4F
IL-1F6
CD39L3
Contactin 3
CLEC4B
MC3R
PGRP-L
PLET1
ADAM9
AMIGO3
CD99-L2
Eph Receptor A5
Ephrin B2
CD316
Kremen1
Eph Receptor B1
PlexinB3

TABLE 8-continued

Cell surface markers for use ACD with the hydrogel particles described ACE2 herein.

DMBT1
FcRn
LIMPII
MUCDHL
Patched1
SLC39A4
IGSF4A
PRAT4B
HHV8-ORF74
4E-BP1 Phospho (Thr36/45)
4E-BP1 Phospho (Thr69)
DCAR1
Von Hippel-Lindau
Isotype Control
Granzyme M
REA Isotype Control
CD300LG
MR1
CD327
B7-H6
CLEC4G
BATF3
IL-38
Monocarboxylic Acid Transporter 1
MC5R
TCF7
TM4SF1
GPR-49 (CRL Region)
CD156a
ADAM33
ADAMTS13
CCL16
CXCL17
Deltex1
FBXO15
GPR34
GPRC5A
Proinsulin
JAK1
MEP1A
Hypocretin receptor 2
p70S6K
RAE-1Îµ
STRA6
FcÎ³RIIA
Insulin R/IGF-I R Heterotetramer
SPARCL1
Spi-B
TRAM
Carboxypeptidase E
Islet Cell Autoantigen 1
Patched2
ST8SIA2
AML1 (pS249)
AMPKÎ±1 (pS182)
BRF1/2
Histone H3 Phospho (Thr11)
MEK1 (pT286)
MMP16
MNK Phospho (T197/T202)
NUMB
Hsp27 Phospho (Ser78)
PKCÎ¸ (pT538)
SIRT1 (pS47)
ZAP-70 (pY493)
ZAP-70 (pY315/pY319)
sRAGE
mCherry
PI 3 Kinase regulatroy subunit Î±
TIMP4
SRC
ZAP-70 (pT493)
TSC2 Phospho (S939)
RagC
SHIP2
MKK4 (pS257)

TABLE 8-continued

Cell surface markers for use ACD with the hydrogel particles described ACE2 herein.

CD79a (pY182)
TRAF1
EVI1
SRC3
SOX11
IL-17F homodimer
CCRL1
FOXP2
IFNAR2
REA Control
CD228
Muc-13
P2X7R
Btk (pY223/Itk (pY180)
CD248
GILT
Recoverin
Cardiac Troponin I
PTF1Î±
NKX2.2
HLA-B7/B27
Myosin light chain 2a
Myosin light chain 2v
Epithelial Antigen
CD79Î± ± cy
CD92

In one embodiment, a plurality of hydrogel particles is used to determine the dynamic range and/or sensitivity of detection of a particular cell surface marker or combination thereof on a population of target cells. For example, the population of hydrogel particles can be tuned to have the SSC and/or FSC profile of the target cell, and subpopulations of the hydrogel particle are derivatized with a specific number of copies of a cell surface marker, e.g., a cell surface receptor, or a domain thereof, for example, an epitope binding region thereof. For example, individual subpopulations of hydrogel particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of hydrogel particles are fluorescently stained for the respective cell surface marker and fluorescence is detected for hydrogel particles in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

Hydrogel particles of the disclosure behave similarly to target cells in procedures such as staining and analysis by flow cytometry or FACS. For example, in one embodiment, a hydrogel particle has one or more optical properties substantially similar to one of the cell types set forth in Table 1, Table 2 or Table 3.

In some embodiments, a target cell is an immune cell. Non-limiting examples of immune cells include B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor infiltrating (TIL) cells, gene modified immune cells including hybridomas, drug modified immune cells, and derivatives, precursors or progenitors of any of the cell types listed herein.

In some embodiments, a target cell encompasses all cells of a particular class of cell with shared properties. For example, a target cell can be a lymphocyte, including NK cells, T cells, and B cells. A target cell can be an activated lymphocyte.

In some embodiments, a target cell is a primary cell, cultured cell, established cell, normal cell, transformed cell, infected cell, stably transfected cell, transiently transfected cell, proliferating cell, or terminally differentiated cells.

In one embodiment, a target cell is a primary neuronal cell. A variety of neurons can be target cells. As non-limiting examples, a target cell can be a primary neuron; established neuron; transformed neuron; stably transfected neuron; or motor or sensory neuron.

In other embodiments, a target cell is selected from the group consisting of: primary lymphocytes, monocytes, and granulocytes.

A target cell can be virtually any type of cell, including prokaryotic and eukaryotic cells.

Suitable prokaryotic target cells include, but are not limited to, bacteria such as *E. coli*, various *Bacillus* species, and the extremophile bacteria such as thermophiles.

Suitable eukaryotic target cells include, but are not limited to, fungi such as yeast and filamentous fungi, including species of *Saccharomyces, Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a non-diseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as hematopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor micro vesicles may be referred to as tumor macro vesicles, and can range in size from 3-10 jam in diameter.

The hydrogel particles described herein can be employed in any flow cytometer known to those of ordinary skill in the art. For example, one or more of the flow cytometers provided in Table 9 below are amenable for use with the hydrogels and assays described herein.

TABLE 9

Instruments for use with embodiments described herein

| Instrument | Manufacturer |
|---|---|
| MACSQuant ® Analyzer 10 | Miltenyi |
| MACSQuant ® VYB | Miltenyi |
| BD FACSCalibur ™ | BD Biosciences |
| BD FACSCanto ™ High Throughput Sampler | BD Biosciences |
| BD FACSCanto II | BD Biosciences |
| BD FACSCanto ™ | BD Biosciences |
| BD FACSCount ™ | BD Biosciences |
| BD Accuri ™ 06 | BD Biosciences |
| BD LSRFortessa TM X-20 | BD Biosciences |
| BD FACSCanto ™ II | BD Biosciences |
| BD LSR II | BD Biosciences |
| BD LSRFortessa ™ | BD Biosciences |
| BD FACSVerse ™ | BD Biosciences |
| BD FACSAria ™ Fusion | BD Biosciences |
| BD FACSAria ™ | BD Biosciences |
| BD FACSAria ™ III | BD Biosciences |
| BD FACSJazz ™ | BD Biosciences |
| BD Influx-WI | BD Biosciences |
| Fortessa X50. | BD Biosciences |
| FlowSight Flow Cytometer | Millipore |
| Guava easyCyte 6-2L Benchtop Flow Cytometer | Millipore |
| guava easyCyte 5HT Benchtop Flow Cytometer | Millipore |
| guava easyCyte 8 Benchtop Flow Cytometer | Millipore |
| guava easyCyte 5 Benchtop Flow Cytometer | Millipore |
| guava easyCyte 8HT Benchtop Flow Cytometer | Millipore |
| guava easyCyte 6HT-2L Benchtop Flow Cytometer | Millipore |
| ImageStreamX Mark II Imaging Flow Cytometer | Millipore |
| Muse Cell Analyzer | Millipore |
| guava easyCyte 12HT Benchtop Flow Cytometer | Millipore |
| guava easyCyte 12 Benchtop Flow Cytometer | Millipore |
| S3e ™ Cell Sorter | Bio-Rad |
| S3 ™ Cell Sorter | Bio-Rad |
| Avalon Cell Sorter | Bio-Rad / Propel Labs |
| CytoFLEX | Beckman Coulter |
| FP 1000 Cell Preparation System | Beckman Coulter |
| Vi-CELL ® XR Cell Viability Analyzer | Beckman Coulter |
| FC 500 Series | Beckman Coulter |
| MoFlo ® Astrios ™ | Beckman Coulter |
| Coulter Epics XL ™ and XL-MCL ™ | Beckman Coulter |
| Gallios ™ | Beckman Coulter |
| CyAn ™ ADP Analyzer | Beckman Coulter |
| Attune ™ Acoustic Focusing Cytometer | Life Technologies |
| Attune ® NxT Acoustic Focusing Cytometer | Life Technologies |
| EVOS | Life Technologies |
| Countess II FL | Life Technologies |
| EC800 Cell Analyzer | Sony |
| SH800 Cell Sorter | Sony |
| SP6800 Spectral Analyzer | Sony |
| SY3200 Cell Sorter | Sony |
| A50-Micro' | Apogee Flow Systems |
| A50-Universal | Apogee Flow Systems |
| Auto40 | Apogee Flow Systems |
| FlowSight | Amnis |
| ImageStream$^x$ Mark II | Amnis |
| JSAN | Bay Bioscience |
| CytoSense | CytoBuoy |
| CytoSub | CytoBuoy |
| CytoSense | CytoBuoy |
| CytoBuoy | CytoBuoy |
| Cytonome Viva ™ G1 | CYTONOME |
| GigaSort ™ | CYTONOME |
| Hydris | CYTONOME |
| Agilent 2100 Bioanalyzer | Agilent Technologies |
| NovoCyte | ACEA Biosciences |

TABLE 9-continued

Instruments for use with embodiments described herein

| Instrument | Manufacturer |
| --- | --- |
| CyFlow ® Space | Partec technology |
| CyFlow ® Cube 8 | Partec technology |
| CyFlow ® Cube 6 | Partec technology |
| CyFlow ® Ploidy Analyser | Partec technology |
| CyFlow ® Counter | Partec technology |
| CyFlow ® miniPOC | Partec technology |
| CyFlow ® SL | Partec technology |
| CyFlow ® Sorter | Partec technology |
| CyFlow ® CCA | Partec technology |
| CyFlow ® Oenolyser | Partec technology |
| NucleoCounter ® NC-3000 ™ | Chemometec |
| NucleoCounter ® NC-250 ™ | Chemometec |
| NucleoCounter ® NC-200 ™ - High Precision Cell Counter | Chemometec |
| HPC-100 Portable Flow Cytometer | Cronus Technologies Ltd |
| Cytell Cell Imaging System | GE Healthcare |
| MAGPIX | Luminex |
| Luminex ® 100/200 ™ System | Luminex |
| FLEXMAP 3D ® | Luminex |
| ImageXpress ® Velos Laser Scanning Cytometer | molecular devices |
| ClonePix ™ 2 | molecular devices |
| SpectraMax ® i3 | molecular devices |
| AQ1 Discrete Analyzer | SEAL Analytical Ltd. |
| AQ2 Discrete Analyzer | SEAL Analytical Ltd. |
| AQ400 Discrete Analyzer | SEAL Analytical Ltd. |
| AQUA 900 | SEAL Analytical Ltd. |
| AA3 HR AutoAnalyzer | SEAL Analytical Ltd. |
| AA1 AutoAnalyzer | SEAL Analytical Ltd. |
| QuAAtro39 | SEAL Analytical Ltd. |
| Infralyzer 2000 | SEAL Analytical Ltd. |
| Technicon AutoAnalyzer II (AAII) | SEAL Analytical Ltd. |
| Technicon / Bran + Luebbe TrAAcs 800-2000 | SEAL Analytical Ltd. |
| Bran + Luebbe FIA Analyzer | SEAL Analytical Ltd. |
| BioSorter ® Large Particle Flow Cytometer | Union Biometrica, Inc. |
| COPAS ™ Large Particle Flow Cytometers | Union Biometrica, Inc. |
| Cellometer Mini Cell Counter | Nexcelom |
| Cellometer Auto T4 Cell Viability Counter | Nexcelom |
| Cellometer Auto X4 Cell Viability Counter | Nexcelom |
| Cellometer Auto 1000 Cell Viability Counter | Nexcelom |
| Cellometer Auto 2000 Cell Viability Counter | Nexcelom |
| Cellometer Vision CBA | Nexcelom |
| Celigo S | Nexcelom |
| NoyoCyte ™ 1000 | ACEA |
| NoyoCyte ™ 2000 | ACEA |
| NoyoCyte ™ 2060 | ACEA |
| NoyoCyte ™ 3000 | ACEA |
| HPC-100 | Handyem |
| S1000EXi | Stratedigm |
| SE520Xi | Stratedigm |
| Sysmex ® DI-60 | Sysmex |
| CellaVision ® DM96 | Sysmex |
| CellaVision ® DM1200 | Sysmex |
| Cytation | BioTek |
| EasyCell Assistant | Medica |
| IN Cell Analyzer GE | Healthcare |
| Fluorish List | |
| Big Blue | BD Biosciences |
| Kermit | Miltenyi |
| ac6 | BD Biosciences |
| srDAs | BD Biosciences |
| a | BD Biosciences |
| FACSCanto II Immunology | BD Biosciences |
| Test Cyt | Millipore |
| milt | Miltenyi |
| ac | BD Biosciences |
| ietest | BD Biosciences |
| Curiel's Aria | BD Biosciences |
| AttuneÂ ® Acoustic Focusing Cytometer Blue/Violet | Life Technologies |
| Medawar LSRII | BD Biosciences |
| Medawar Calibur | BD Biosciences |
| FACSAria INER | BD Biosciences |
| Attune R/A | Life Technologies |
| Fortessa | BD Biosciences |
| Aria | BD Biosciences |
| SORTER | BD Biosciences |
| Cyan | Beckman Coulter |
| LSR II | BD Biosciences |
| ARIA | BD Biosciences |
| Canto II | BD Biosciences |
| F09 - LSR Fortessa 1 | BD Biosciences |
| "The Hoff" | BD Biosciences |
| 6th Floor Hess Fortessa A | BD Biosciences |
| Cerebro BDFACSAriaII | BD Biosciences |
| Mystique BDFACSAriaIII | BD Biosciences |
| Godzilla BDFACSAriaII | BD Biosciences |
| Wolverine BDFACSAriaII | BD Biosciences |
| Megatron BDFACSAriaII | BD Biosciences |
| Megatron BDFACSAriaII | BD Biosciences |
| Fortessa B | BD Biosciences |
| 6 colour Canto II | BD Biosciences |
| 10 colour LSR II | BD Biosciences |
| 4 laser 13 colour Influx sorter | BD Biosciences |
| 14 colour X20 | BD Biosciences |
| SORP | BD Biosciences |
| FACSAria INER | BD Biosciences |
| L5R561 | BD Biosciences |
| Fortessa FCF UZH | BD Biosciences |
| LSR 2 B | BD Biosciences |
| LSRII-C | BD Biosciences |
| Cal 3 | BD Biosciences |
| Aria II A | BD Biosciences |
| LSR 16 | BD Biosciences |
| LSB Fortessa | BD Biosciences |
| IMMUN LSRII | BD Biosciences |
| IRC | BD Biosciences |
| UV LSR | BD Biosciences |
| 5 Laser Aria | BD Biosciences |
| Curiel's LSR II | BD Biosciences |
| LSR Fortessa | BD Biosciences |
| Mauzeroll Aria | BD Biosciences |
| Frenette | BD Biosciences |
| Fallon | Beckman Coulter |
| Galios | Beckman Coulter |
| LSRIIFortessa | BD Biosciences |
| FACSCanto II CLSB | BD Biosciences |
| LSR II SC | BD Biosciences |
| UNCA Fortessa | BD Biosciences |
| VERSE | BD Biosciences |
| ARIAII | BD Biosciences |
| ARIAIII | BD Biosciences |
| F09 - BD LSRFortessa | BD Biosciences |
| HMRI FACSCanto II A | BD Biosciences |
| HMRI FACScantoll B (HTS) | BD Biosciences |
| HMRI Aria III | BD Biosciences |
| L2 | BD Biosciences |
| UoN Canto | BD Biosciences |
| LSRII M902 | BD Biosciences |
| Fortessa 1 | BD Biosciences |
| F05 - FACSAria | BD Biosciences |
| F02 - FACSAria III | BD Biosciences |
| F10 - BD FACSAria III | BD Biosciences |
| F03 - Guava | Millipore |
| Aria Blue 11 Color | BD Biosciences |
| Aria Red | BD Biosciences |
| Aria Orange | BD Biosciences |
| Aria Cyan | BD Biosciences |
| Aria Emerald | BD Biosciences |
| Aria Silver BSL3 | BD Biosciences |
| LSR Fortessa | BD Biosciences |
| LSR II Bldg 4 | BD Biosciences |
| LSR Fortessa bldg 4 | BD Biosciences |
| CANTO II Bldg 50 | BD Biosciences |
| 4 Laser LSR II | BD Biosciences |
| 5 Laser LSR II | BD Biosciences |
| FACSArray BL-2 | BD Biosciences |
| FACSCalibur | BD Biosciences |
| DUAL for long term studies | BD Biosciences |
| MoFlo 1095 Production only | Beckman Coulter |

TABLE 9-continued

Instruments for use with embodiments described herein

| Instrument | Manufacturer |
|---|---|
| BL-2 FACSAria III sorter | BD Biosciences |
| Astrios BL-2 sorter | Beckman Coulter |
| Tessy | BD Biosciences |
| LSR II-1 | BD Biosciences |
| Fortessa | BD Biosciences |
| 4 laser AriaIII | BD Biosciences |
| LSRFortessa | BD Biosciences |
| UoN FACSAria II cell sorter | BD Biosciences |
| Door | Beckman Coulter |
| Fortessa | BD Biosciences |
| WCI - FACSAria I | BD Biosciences |
| LSRII Karp8 | BD Biosciences |
| Karp 8 | BD Biosciences |
| Canto | BD Biosciences |
| Aria sorter | BD Biosciences |
| DI lab | BD Biosciences |
| DI FACSAria | BD Biosciences |
| Constance | BD Biosciences |
| DI FACSAria III | BD Biosciences |
| WCI_FACS Canto | BD Biosciences |
| MACSQuant 10 | Miltenyi |
| VAMC Memphis LSR | BD Biosciences |
| VAMC Memphis S3 | Bio-Rad |
| ARIA INER | BD Biosciences |
| Uhura | BD Biosciences |
| Kirk | BD Biosciences |
| Data | Millipore |
| Spock | BD Biosciences |
| McCoy | BD Biosciences |

EXAMPLES

The present invention is further illustrated by reference to the following Examples. However, it should be noted that these Examples, like the embodiments described above, are illustrative and are not to be construed as restricting the scope of the invention in any way.

Example 1: Generation of Hydrogel Particles

Photomasks for UV lithography were sourced from CADart Services Inc. and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald J C, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker (N,N'-bisacrylamide, 0.05-1% w/v), an accelerator, and ammonium persulfate (1% w/v) was used. An accelerator, (N,N,N',N'tetramethylethylenediamine (2% vol %) was added to the oil-phase in order to trigger hydrogel particle polymerization after droplet formation.

Several co-monomers were added to the basic gel formulation to add functionality. Allyl-amine provided primary amine groups for secondary labeling after gel formation. We modulated forward scatter by adjusting the refractive index of the gel by adding co-monomers allyl acrylate and allyl methacrylate. Side scattering of the droplets was tuned by adding a colloidal suspension of silica nanoparticles and/or PMMA (poly(methyl methacrylate)) particles (~100 nm) to the central aqueous phase prior to polymerization.

Stoichiometric multiplexing of the hydrogel particles was achieved by utilizing co-monomers containing chemically orthogonal side groups (amine, carboxyl, maleimide, epoxide, alkyne, etc.) for secondary labeling.

Droplets were formed at an average rate of 5 kHz and were collected in the fluorocarbon oil phase. Polymerization was completed at 50° C. for 30 minutes, and the resulting hydrogel particles were washed from the oil into an aqueous solution.

Example 2: Generation and Visualization of 12 11 m Hydrogel Particles

Figure 3:
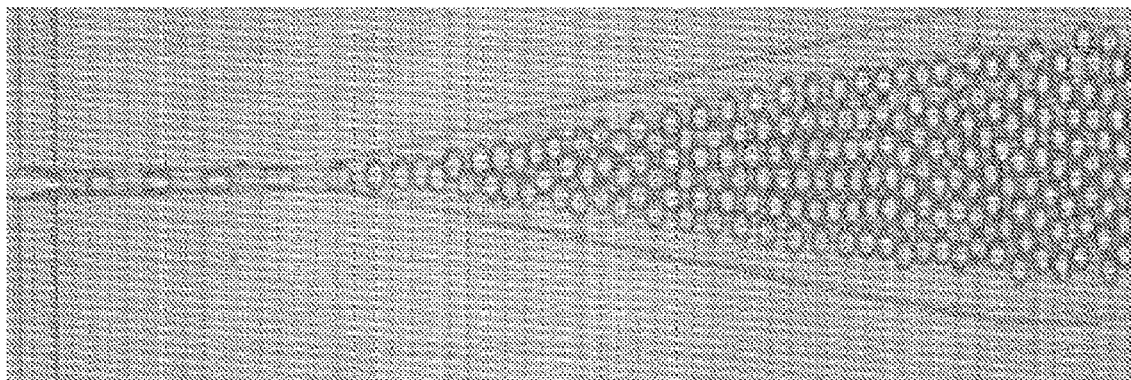
FIG. 3 provides brightfield and fluorescent images of labeled hydrogel particles of the disclosure.
Figure 3:
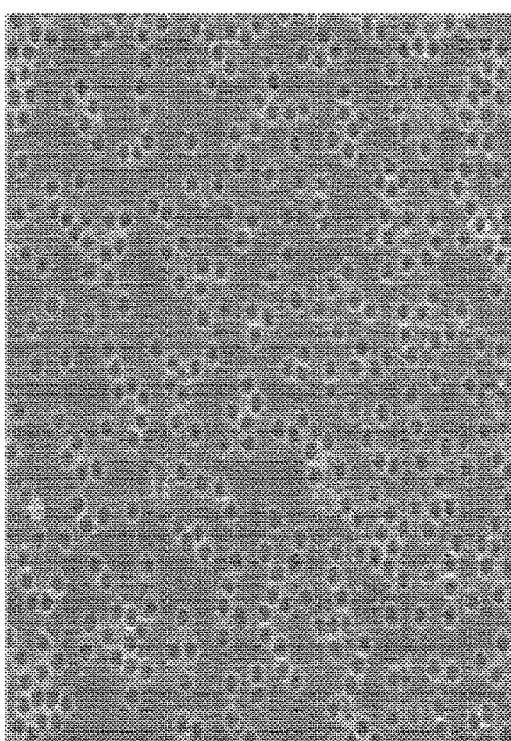
Figure 3:
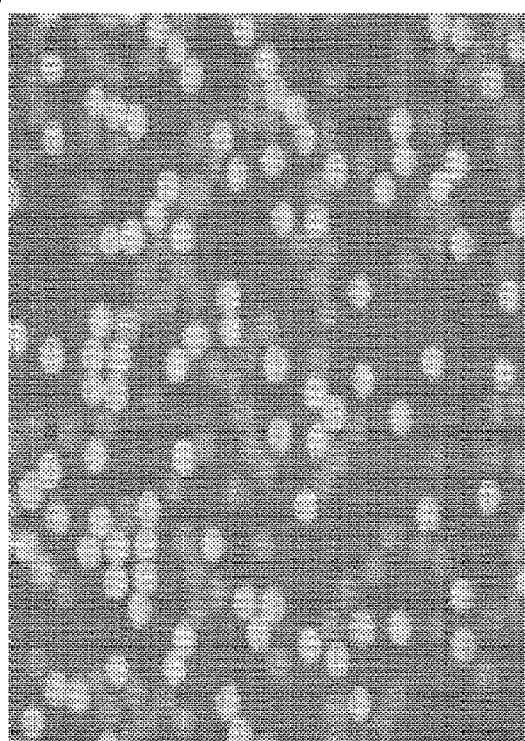

Water containing 5% acrylamide, 0.25% bisacrylamide, 0.05% allyl amine, and 0.1% ammonium persulfate was flowed through a center channel and focused by oil containing 0.1% TEMED through a 10 micron nozzle to produce 10 µm hydrogel particles, shown in FIG. 3A. Following polymerization, the particles were washed in water, shown in FIG. 3B, and conjugated to dyes of interest. The fluorescent hydrogel particles were visualized with fluorescence microscopy, shown in FIG. 3C.

Example 3: Multidimensional Tuning of Hydrogel Particle Optical Properties

Figure 4:
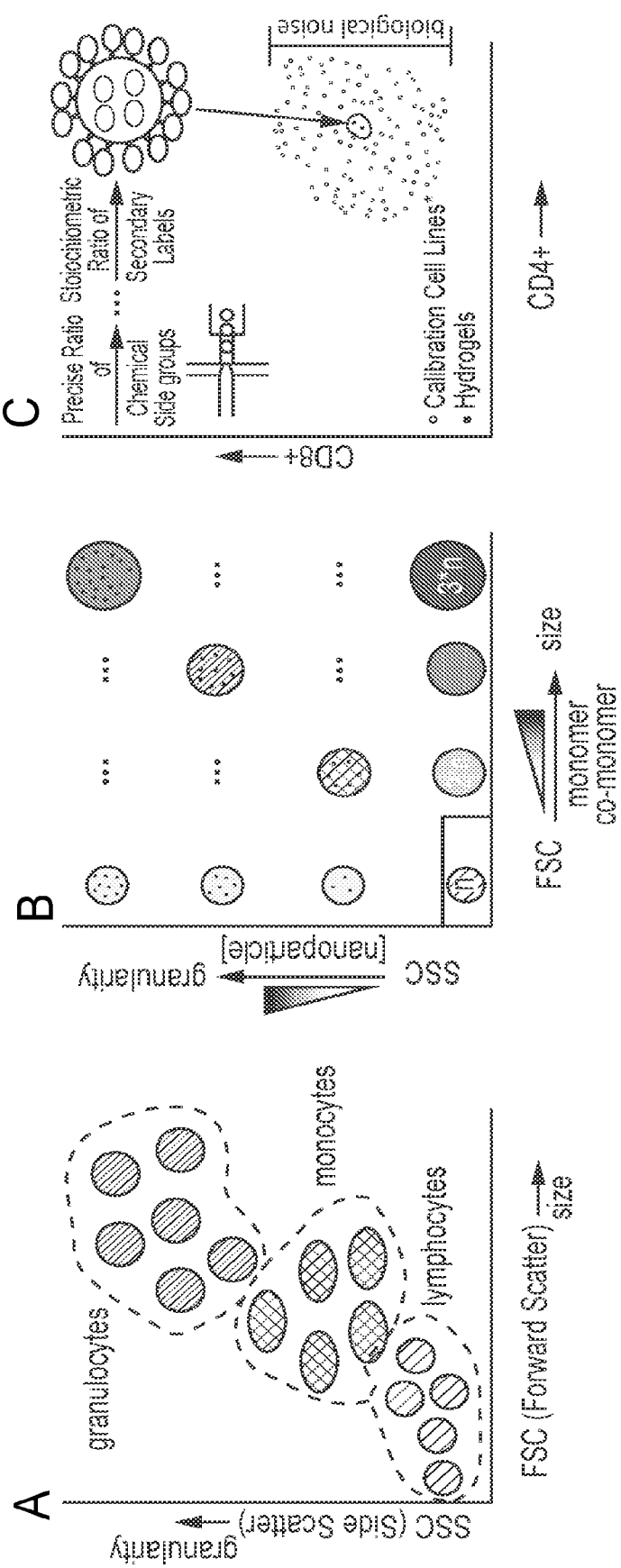
FIG. 4 illustrates the use of hydrogel particles of the disclosure as calibrants for cell types displaying a variety of optical scattering properties.

As depicted in FIG. 4, hydrogel particles are tuned in multiple dimensions to match specific cell types unlike polystyrene beads. Cells are deconvolved using combinations of optical parameters such as FSC and SSC (FIG. 4A) or secondary markers. Hydrogel particles are tuned to match the SSC and FSC of specific cell types unlike polystyrene beads (brown) which are limited in size (FSC) and side scattering (FIG. 4B). Hydrogel particles are further functionalized with stoichiometrically tuned ratios of specific chemical side-groups and secondary labels allowing the cell type to be precisely matched without suffering from biological noise as fixed cell lines do (FIG. 4C).

Figure 5:
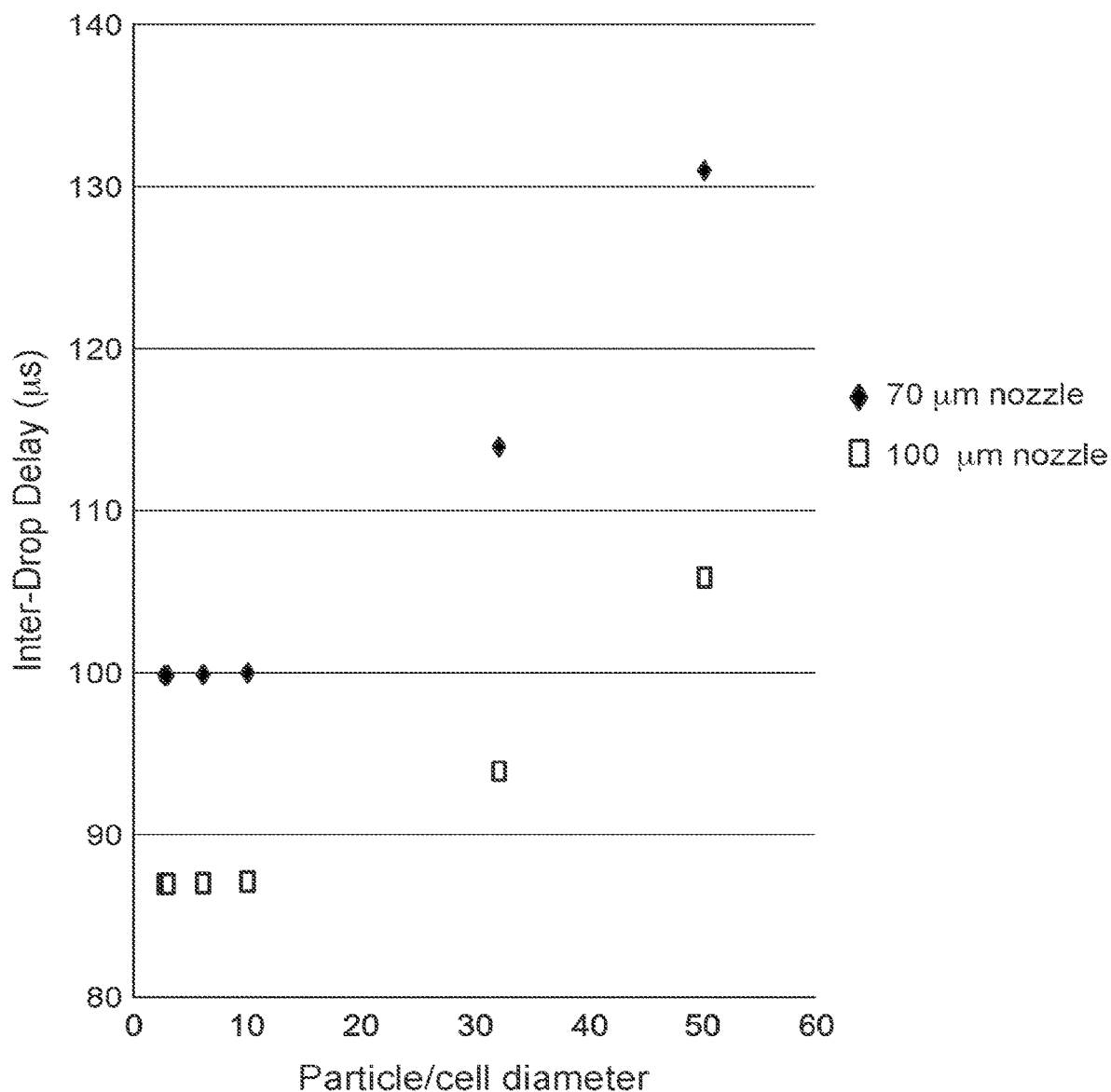
FIG. 5 provides dating showing correlation of inter-drop delay for a flow cytometer with hydrogel particle diameter.

Example 4: Flow Cytometer Delay Time as a Function of Hydrogel Particle Diameter As shown in FIG. 5, the inter-drop delay for a flow cytometer can be precisely correlated to hydrogel particle diameter. Data are shown for hydrogel particles of 3, 6, 10, 32, and 50 µm diameters using flow cytometer nozzle sizes of 70 and 100 µm.

Example 5: Comparison of Hydrogel Particles with Encapsulated DNA to Cells

Figure 6:
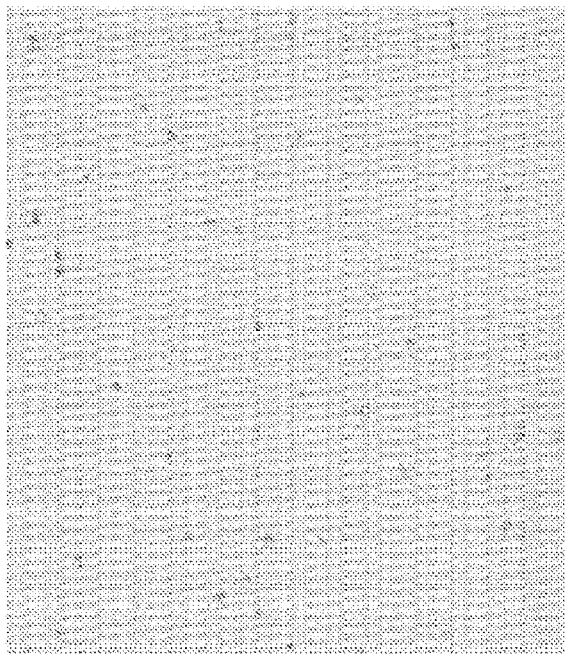
FIG. 6 provides brightfield (6A and 6C) and fluorescent (6B and 6D) images of Chinese Hamster Ovary cells (6A and 6B) and hydrogel particles of the disclosure (6C and 6D).
Figure 6:
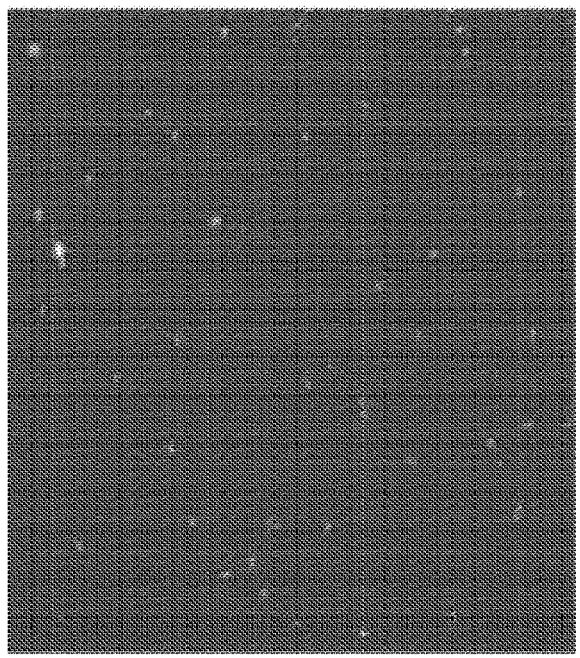
Figure 6:
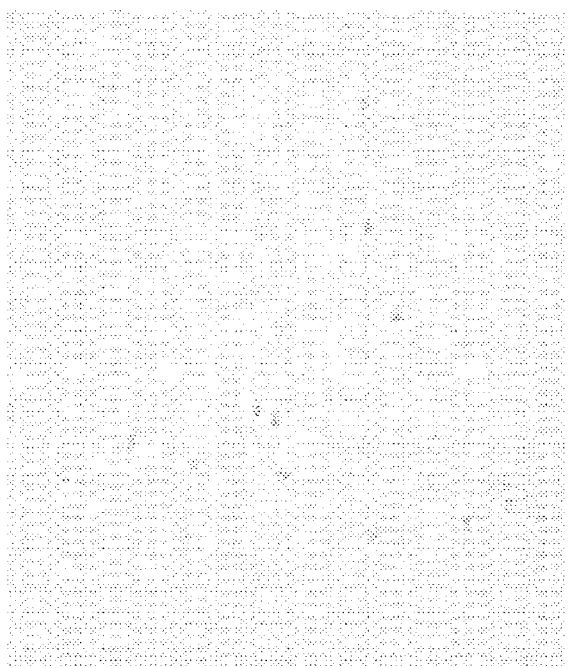
Figure 6:
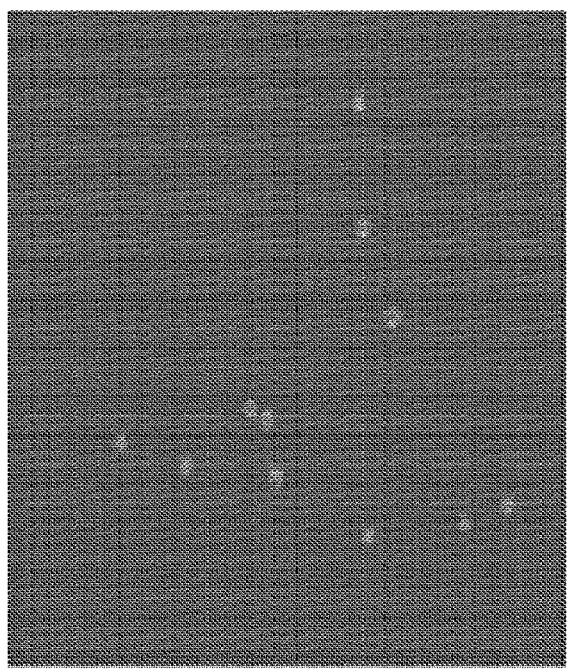

To form hydrogel particles with encapsulated DNA, 40 µg/mL-1000) µg/mL of reconstituted calf thymus DNA was added to a polymer mix containing 20% 19:1(acrylamide:bis-acrylamide) and 0.1% allyl amine in water. 0.4% ammoniumpersulfate was added to the mix prior to droplet formation. Hydrogel particles were formed as described in Example 1. Hydrogel particles with 200 µg/mL of encapsulated calf thymus DNA displayed cell-like staining using propidium iodide as visualized using a commercial imaging cytometer and compared to Chinese Hamster Ovary cells stained using the same procedure. Images were obtained using a Nexcelom Cellometer™ (FIG. 6).

Figure 7:
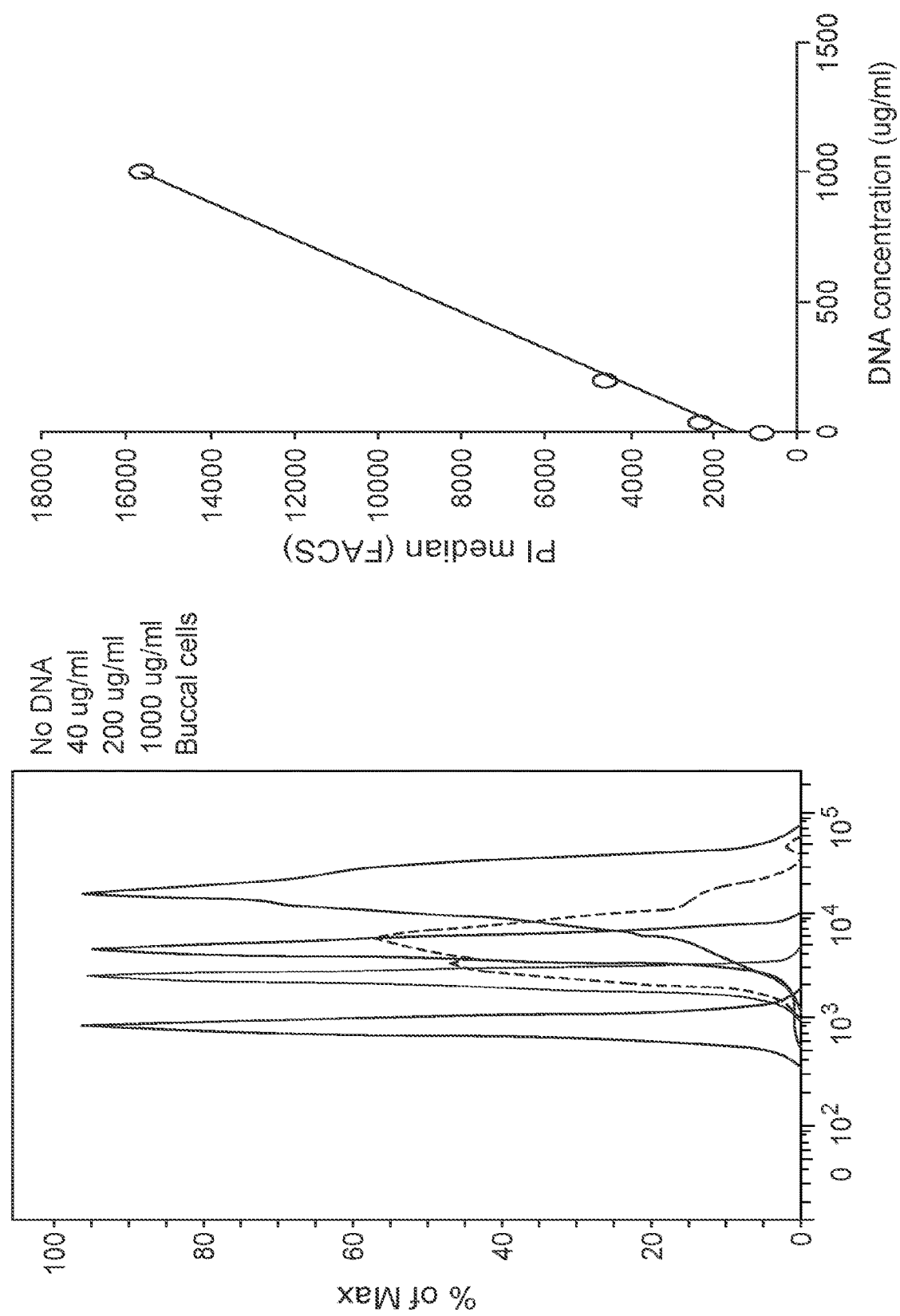
FIG. 7 provides data showing comparison of human buccal cells to hydrogel particles encapsulating different amounts of DNA, as measured by fluorescence-activated cell sorting (FACS).

Cells obtained from a buccal swab were washed in PBS and stained with propidium iodide. In parallel, populations of hydrogel particles containing a range of DNA concentrations were also stained in the same manner. Both the cell and particle suspensions were analyzed on a flow cytometer (488/590 nm excitation/emission). Flow cytometry analysis of cheek cells and the same range of encapsulated DNA particles showed that the particles display a range of cell-like fluorescent properties (FIG. 7, left panel). The intensity of staining shows a linear correlation with the median intensity as measured by flow cytometry (FIG. 7, right panel).

Example 6: Tuning of Hydrogel Particle Side Scattering

Figure 8:
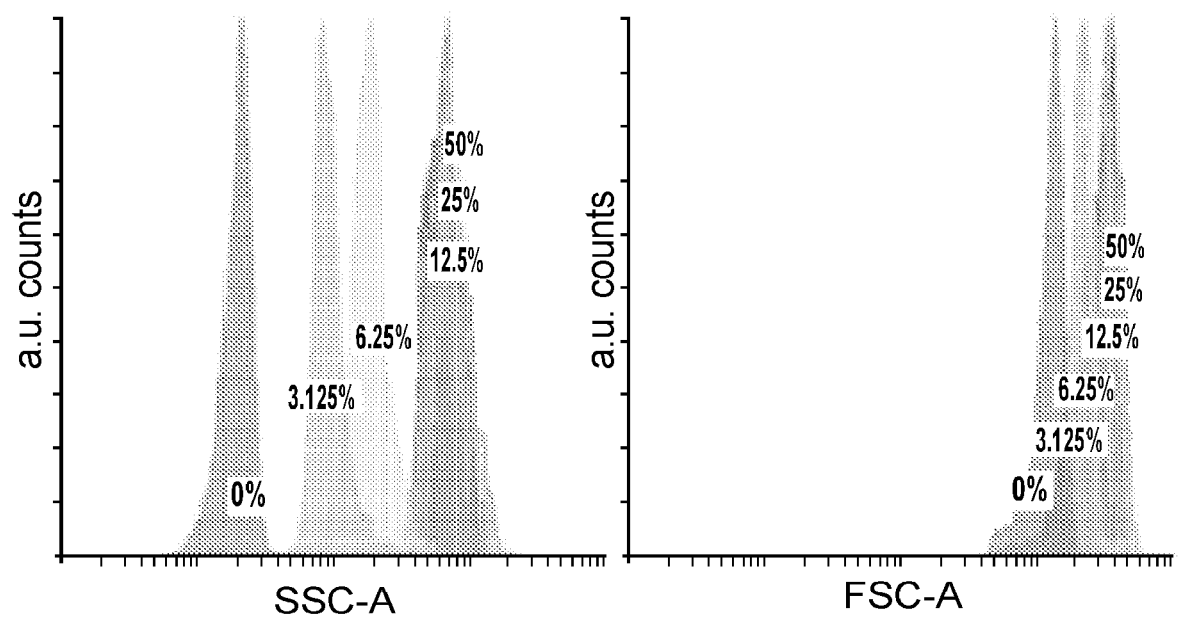
FIG. 8 provides data for hydrogel particles encapsulating nanoparticles at different concentrations, demonstrating tuning of side scattering independent of forward scattering.

Colloidal silica was added at 12.5%, 6.25%, 3.125% and 0% to the aqueous fraction of the polymer mix and hydrogel particles were formed as described in Example 1. Forward and side scattering data were obtained using a flow cytometer. The results showed that side scatter signal (FIG. 8, left panel) increased with higher percentages of encapsulated nanoparticles while forward scatter (FIG. 8, right panel) remained generally unchanged, demonstrating the independent tuning of side scatter and forward scatter.

Example 7: Tuning of Hydrogel Particle Forward Scattering

Figure 9:
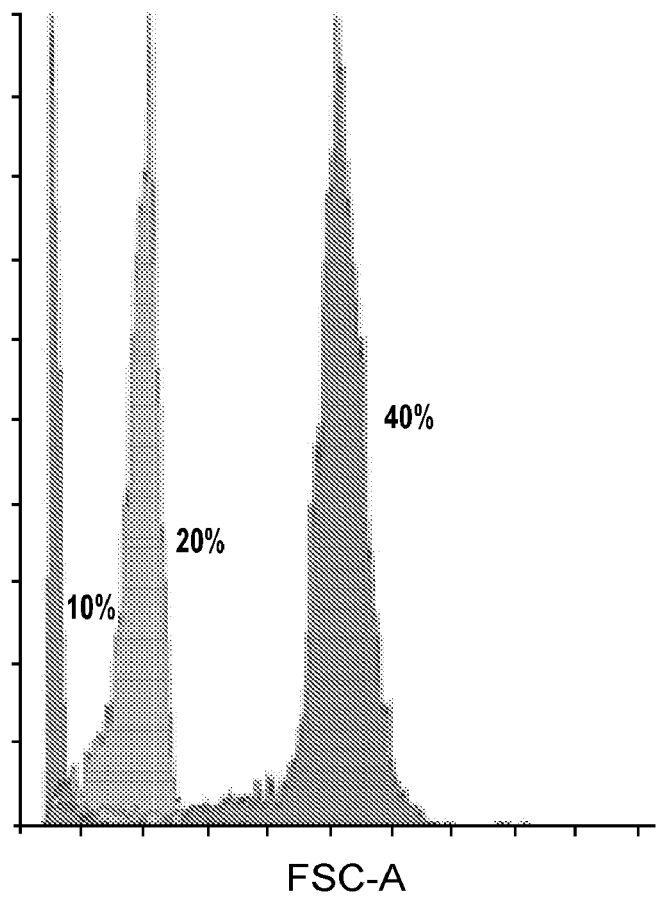
FIG. 9 provides data for hydrogel particles produced with different percentages of polymer, demonstrating tuning of refractive index measured by forward scattering.

In this experiment, the percentage of acrylamide:bisacrylamide in the hydrogel composition was varied from between 10 and 40% to tune the refractive index of the hydrogel particles as measured by forward scattering in a flow cytometer. As shown in FIG. 9, the forward scattering increased with increasing percentages of acrylamide:bisacrylamide as a fraction of water.

Example 8: Tuning of Hydrogel Particle Optical Properties

An example of tuning hydrogel particles to match optical properties of a desired cell subtype. Co/monomers can be combined with nanoparticles to tune both forward and side scatter properties of the hydrogels using passive optical measurements in a flow cytometer. By combining these properties with chemically labile co-monomers (e.g. allyl amine, acrylic acid), additional fluorophores/proteins/biological side groups can be added and labeled (if desired) in order to match cell subpopulation staining in addition to scattering properties. These are the three primary metric by which cells are identified using flow cytometry. Additional side groups, such as those containing heavy metals, can be used for Cy-TOF (cytometry, time of flight mass spectrometry) calibration for example. Finally, biocompatible material can be encapsulated to mimic subcellular organelle staining.

Example 9: Tuning of Hydrogel Particle Optical Properties

A 50 nm nanoparticle colloidal suspension was incorporated into the hydrogel matrix to mimic the optical properties of lymphocytes and monocytes (FIGS. 13A and 13B). The percent composition of the suspension was altered to match the blood cell subpopulations from the blood sample control (Streck) (FIG. 13C).

Figure 13:
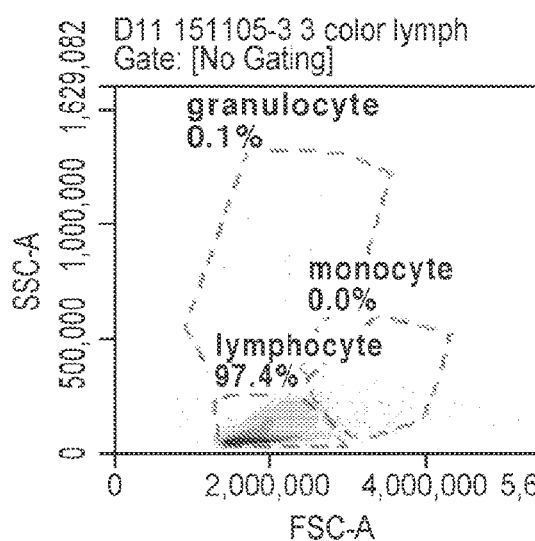
FIG. 13 are scatter plots for various hydrogel particles (A) and (B) and a commercial blood sample (C).
Figure 13:
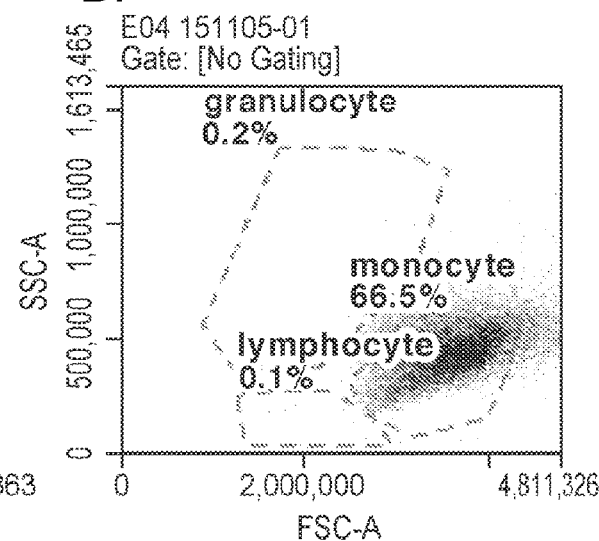
Figure 13:
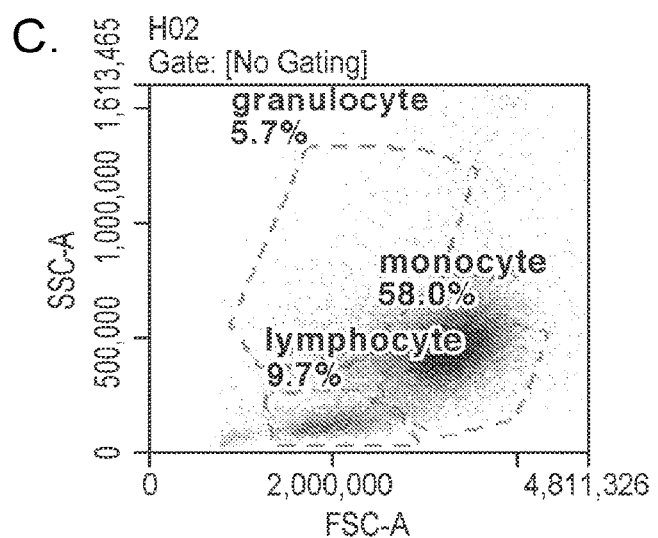

Specifically, the concentration of the acrylamide monomer (0.7-0.8M) of the hydrogel particle was adjusted to increase the forward scatter of the particles to match blood cell subpopulations. The percentage of bisacrylamide cross linker can also be changed to affect forward scatter (1-5%). Silica nanoparticles were used at 5% or 10% in the compositions to adjust side scatter. The results of this experiment are shown in FIG. 13.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A population of hydrogel particles, each hydrogel particle comprising:
   (i) a polymer comprising a polymerized monomer and a co-monomer;
   (ii) one or more biomolecules; and
   (iii) a nanoparticle encapsulated within the hydrogel,
   wherein the population hydrogel particles has an optical property that is substantially similar to a corresponding property of a target cell, the optical property provided by the co-monomer, a ratio of monomer to co-monomer, or the encapsulated nanoparticle.

2. The population of hydrogel particles of claim 1, wherein the polymerized monomer is actic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methaciylate, methacrylic acid, sodium methacrylate, glycerol methacrylate, hydroxypropyl methacrylate, hydroxybutyl methacrylate, phenyl acylate, phenyl methacrylate, benzyl acylate, benzyl methacrylate, 2-phenylethyl acrylate, 2-phenylethyl methaciylate, 2-phenoxyethyl acrylate, 2-phenoxyethyl methaciylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridinemethacrylamide, N-alkylacrylamide, N-alkylmethacrylamide, N,N-dialkylacrylamide, N-[(dialkylamino)alkyl]acrylamide, N-[(dialkylamino)alkyl]methacrylamide, (dialkylamino)alkyl acrylate, or (dialkylamino)alkyl methacrylate.

3. The population of hydrogel particles of claim 1, wherein the polymerized monomer is acrylamide.

4. The population of hydrogel particles of claim 1, wherein the co-monomer comprises one or more chemical side groups that are capable of reacting with a dye molecule.

5. The population of hydrogel particles of claim 1, wherein the co-monomer is allyl amine, allyl acrylate, allyl methacrylate, allyl alcohol, allyl isothiocyanate, allyl chloride, allyl maleimide, or bis-acrylamide.

6. The population of hydrogel particles of claim 5, wherein the bis-acrylamide is N,N'-methylenebisacrylamide, N,N'-methylenebismethacrylamide, N,N'-ethylenebisacrylamide, N,N'-ethylenebis-methacrylamide, N,N'propylenebisacryl amide, or N,N'-(1,2-dihydroxyethylene) bisacrylamide.

7. The population of hydrogel particles of claim 1, wherein the polymer comprises polymerized acrylamide and bis-acrylamide.

8. The population of hydrogel particles of claim 7, wherein the optical property is provided by a ratio of acrylamide to bis-acrylamide.

9. The population of hydrogel particles of claim 1, wherein the encapsulated nanoparticle is polymethyl methacrylate (PMMA), polystyrene (PS), or silica.

10. The population of hydrogel particles of claim 1, wherein the encapsulated material is PMMA.

11. The population of hydrogel particles of claim 1, wherein the encapsulated material is PS.

12. The population of hydrogel particles of claim 1, wherein the encapsulated material is silica.

13. The population of hydrogel particles of claim 7, wherein the encapsulated material is silica.

14. The population of hydrogel particles of claim 1, comprising a single species of biomolecule.

15. The population of hydrogel particles of claim 1, comprising a plurality of different species of biomolecules.

16. The population of hydrogel particles of claim 1, wherein each hydrogel particle comprises a surface, and the surface is functionalized with one or more biomolecules.

17. The population of hydrogel particles of claim 16, wherein the surface is functionalized with a single species of biomolecule.

18. The population of hydrogel particles of claim 16, wherein the surface is functionalized with a plurality of different species of biomolecules.

19. The population of hydrogel particles of claim 1, wherein each hydrogel particle in the population of hydrogel particles comprises a known concentration of the one or more biomolecules.

20. The population of hydrogel particles of claim 16, wherein the surface is functionalized with one or more: (a) cell surface marker, (b) nucleic acid sequence, (c) polypeptide, (d) antibody or epitope binding region thereof, or (e) combinations thereof.

21. The population of hydrogel particles of claim 20, wherein the surface is functionalized with one more cell surface marker.

22. The population of hydrogel particles of claim 20, wherein the surface is functionalized with one or more antibody or epitope binding region thereof.

23. The population of hydrogel particles of claim 1, wherein the one or more biomolecules are encapsulated within the hydrogel particles.

24. The population of hydrogel particles of claim 23, wherein the one or more encapsulated biomolecules is a nucleic acid or peptide.

25. The population of hydrogel particles of claim 24, wherein the one or more encapsulated biomolecules is a nucleic acid.

26. The population of hydrogel particles of claim 1, wherein one more biomolecules are encapsulated within the hydrogel particles, and a surface of the hydrogel particles is functionalized with one or more biomolecules.

27. The population of hydrogel particles of claim 26, wherein the one or more biomolecules encapsulated within the hydrogel particles and the one or more biomolecules on the surface of the hydrogel particles are different species of biomolecules.

28. The population of hydrogel particles of claim 1, wherein the one or more biomolecules is selected from Table 8.

29. The population of hydrogel particles of claim 21, wherein the cell surface marker is IL15, IL21, CD137, or a combination thereof.

30. The population of hydrogel particles of claim 21, wherein the one or more cell surface markers is CD4, CD8, CD16, CD56, CD19, or combinations thereof.

31. The population of hydrogel particles of claim 30, wherein the target cell is a T cell, Natural Killer cell, or B cell.

32. The population of hydrogel particles of claim 21, wherein the one or more cell surface markers is hemoglobin.

33. The population of hydrogel particles of claim 32, wherein the hemoglobin is human hemoglobin.

34. The population of hydrogel particles of claim 32, wherein the target cell is an erythrocyte or monocyte.

35. The population of hydrogel particles of claim 1, having an average particle volume, average particle diameter, or both that is substantially similar to the target cell.

36. The population of hydrogel particles of claim 33, having an average particle volume, average particle diameter, or both that is substantially similar to the target cell.

37. The population of hydrogel particles of claim 1, wherein each hydrogel particle in the population of hydrogel particles has substantially the same concentration of the one or more biomolecules.

38. The population of hydrogel particles of claim 1, wherein the hydrogel particle has an elasticity that is substantially similar to the elasticity of a target cell.

39. An aqueous suspension comprising the population of hydrogel particles of claim 1 suspended therein.

40. A population of hydrogel particles, each hydrogel particle comprising:
- (i) a polymer comprising a polymerized monomer and a co-monomer;
- (ii) one or more biomolecules comprising CD4, CD8, CD16, CD56, CD19, IL15, IL21, CD137, hemoglobin, or combinations thereof; and
- (iii) a nanoparticle encapsulated within the hydrogel,
- wherein each hydrogel comprises a diameter ranging from 1-100 μm, and no more than about 10% of the hydrogel particles in the population of hydrogel particles have an average diameter greater than about 10% of the average diameter.

41. The population of hydrogel particles of claim 40, wherein the nanoparticles encapsulated within the hydrogel have a diameter of about 100 nm.

* * * * *

UNITED STATES PATENT AND TRADEMARK OFFICE
CERTIFICATE OF CORRECTION

PATENT NO. : 11,747,261 B2
APPLICATION NO. : 16/933028
DATED : September 5, 2023
INVENTOR(S) : Jeffrey Kim et al.

It is certified that error appears in the above-identified patent and that said Letters Patent is hereby corrected as shown below:

In the Claims

Column 114, Claim 1, Line 34, the text "the population hydrogel particles" should read --the population of hydrogel particles--.

Column 114, Claim 2, Line 40, the text "actic acid" should be --lactic acid--.

Column 114, Claim 2, Lines 50-51, the text "methoxy-poly(ethylene glycol) methaciylate" should read --methoxy-poly(ethylene glycol) methacrylate--.

Column 114, Claim 2, Line 53, the text "phenyl acylate" should read --phenyl acrylate--.

Column 114, Claim 2, Line 54, the text "benzyl acylate" should read --benzyl acrylate--.

Column 114, Claim 2, Line 55, the text "2-phenylethyl methaciylate" should read --2-phenylethyl methacrylate--.

Column 114, Claim 2, Line 56, the text "2-phenoxyethyl methaciylate" should read --2-phenoxyethyl methacrylate--.

Column 115, Claim 2, Lines 1-2, the text "N-benzyl methaciylamide" should read --N-benzyl methacrylamide--.

Column 115, Claim 2, Line 3, please insert a comma after the text "N-diphenylmethyl acrylamide."

Column 115, Claim 2, Lines 14-15, the text "2-vinylpyridinemethacrylamide" should read --2-vinylpyridine--.

Column 115, Claim 6, Lines 32-33, the text "N,N'propylenebisacryl" should read --N,N'-propylenebisacryl--.

Signed and Sealed this
Twenty-first Day of November, 2023

*Katherine Kelly Vidal*

Katherine Kelly Vidal
*Director of the United States Patent and Trademark Office*

Column 116, Claim 21, Line 11, the text "one more" should read --one or more--.

Column 116, Claim 26, Line 27, the text "one more" should read --the one or more--.